United States Patent
Chuu et al.

(10) Patent No.: US 10,718,020 B2
(45) Date of Patent: *Jul. 21, 2020

(54) METHODS OF FETAL ABNORMALITY DETECTION

(71) Applicant: Verinata Health, Inc., Redwood City, CA (US)

(72) Inventors: Yue-Jen Chuu, Cupertino, CA (US); Richard P. Rava, Redwood City, CA (US)

(73) Assignee: Verinata Health, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/279,066

(22) Filed: Sep. 28, 2016

(65) Prior Publication Data

US 2017/0073757 A1    Mar. 16, 2017

Related U.S. Application Data

(63) Continuation of application No. 14/677,854, filed on Apr. 2, 2015, now Pat. No. 9,493,831, which is a continuation of application No. 13/792,661, filed on Mar. 11, 2013, now abandoned, which is a continuation of application No. 13/012,222, filed on Jan. 24, 2011, now abandoned.

(60) Provisional application No. 61/297,755, filed on Jan. 23, 2010.

(51) Int. Cl.
*C12Q 1/6883* (2018.01)
*C12Q 1/6869* (2018.01)
*C12Q 1/6809* (2018.01)
*C12Q 1/68* (2018.01)

(52) U.S. Cl.
CPC ......... *C12Q 1/6883* (2013.01); *C12Q 1/6869* (2013.01); *C12Q 2600/112* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | |
|---|---|---|
| 5,270,184 A | 12/1993 | Walker et al. |
| 5,302,509 A | 4/1994 | Cheeseman |
| 5,399,491 A | 3/1995 | Kacian et al. |
| 5,422,252 A | 6/1995 | Walker et al. |
| 5,427,663 A | 6/1995 | Austin et al. |
| 5,437,975 A | 8/1995 | Mcclelland et al. |
| 5,556,773 A | 9/1996 | Youmo |
| 5,639,669 A | 6/1997 | Ledley |
| 5,641,628 A | 6/1997 | Bianchi |
| 5,676,849 A | 10/1997 | Sammons et al. |
| 5,695,934 A | 12/1997 | Brenner |
| 5,879,883 A | 3/1999 | Benson et al. |
| 5,962,234 A | 10/1999 | Golbus |
| 5,994,057 A | 11/1999 | Mansfield |
| 6,027,923 A | 2/2000 | Wallace |
| 6,100,029 A | 8/2000 | Lapidus et al. |
| 6,124,120 A | 9/2000 | Lizardi |
| 6,154,707 A | 11/2000 | Livak et al. |
| 6,190,870 B1 | 2/2001 | Schmitz et al. |
| 6,210,891 B1 | 4/2001 | Nyren et al. |
| 6,258,540 B1 | 7/2001 | Lo et al. |
| 6,329,150 B1 | 12/2001 | Lizardi et al. |
| 6,440,706 B1 | 8/2002 | Vogelstein et al. |
| 6,618,679 B2 | 9/2003 | Loehriein et al. |
| 6,632,655 B1 | 10/2003 | Mehta et al. |
| 6,927,028 B2 | 8/2005 | Dennis et al. |
| 7,252,946 B2 | 8/2007 | Szasz |
| 7,332,277 B2 | 2/2008 | Dhallan |
| 7,442,506 B2 | 10/2008 | Dhallan |
| 7,582,420 B2 | 9/2009 | Oliphant et al. |
| 7,645,576 B2 | 1/2010 | Lo et al. |
| 7,727,720 B2 | 6/2010 | Dhallan et al. |
| 7,838,647 B2 | 11/2010 | Hahn et al. |
| 7,888,017 B2 | 2/2011 | Quake et al. |
| 7,955,794 B2 | 6/2011 | Shen et al. |
| 8,003,354 B2 | 8/2011 | Shen et al. |
| 8,008,018 B2 | 8/2011 | Quake et al. |
| 8,137,912 B2 | 3/2012 | Stoughton et al. |
| 8,168,389 B2 | 5/2012 | Shoemaker et al. |
| 8,195,415 B2 | 6/2012 | Fan et al. |
| 8,293,470 B2 | 10/2012 | Quake et al. |
| 8,296,076 B2 | 10/2012 | Fan et al. |
| 8,318,430 B2 | 11/2012 | Chuu |
| 8,372,584 B2 | 2/2013 | Shoemaker et al. |
| 8,682,594 B2 | 3/2014 | Fan et al. |

(Continued)

FOREIGN PATENT DOCUMENTS

| | | |
|---|---|---|
| CA | 2737643 A1 | 3/2010 |
| EP | 0994963 B1 | 5/2003 |

(Continued)

OTHER PUBLICATIONS

U.S. Appl. No. 61/296,358, filed Jan. 19, 2010, Chuu et al.
U.S. Appl. No. 61/296,464, filed Jan. 19, 2010, Burke et al.
A pyrosequencing-tailored nucleotide barcode design unveils opportunities for large-scale sample multiplexing, Parameswaran, et al., Nucleic Acids Research, 35(19):e130 (2007) ("Parameswaran").
A Wolters Kluwer Company. Stedman'S Medical Dictionary, 28th Edition. 351 West Camden Street, Baltimore, Maryland 21201-2436. 2006; 1079.
Adinolfi, et al. Rapid detection of aneuploidies by microsatellite and the quantitative fluorescent polymerase chain reaction. Prenat. Diagn. 1997; 17(13):1299-311.

(Continued)

*Primary Examiner* — Channing S Mahatan
(74) *Attorney, Agent, or Firm* — Fish & Richardson P.C.

(57) ABSTRACT

Methods and kits for selectively enriching non-random polynucleotide sequences are provided. Methods and kits for generating libraries of sequences are provided. Methods of using selectively enriched non-random polynucleotide sequences for detection of fetal aneuploidy are provided.

23 Claims, 41 Drawing Sheets

Specification includes a Sequence Listing.

(56) References Cited

U.S. PATENT DOCUMENTS

| | | | |
|---|---|---|---|
| 9,017,942 B2 | 4/2015 | Shoemaker et al. | |
| 9,493,831 B2 * | 11/2016 | Chuu | C12Q 1/6869 |
| 2001/0051341 A1 | 12/2001 | Lo et al. | |
| 2002/0016450 A1 | 2/2002 | Laugharn et al. | |
| 2002/0142324 A1 | 10/2002 | Wang et al. | |
| 2002/0164816 A1 | 11/2002 | Quake | |
| 2003/0022207 A1 | 1/2003 | Balasubramanian | |
| 2003/0044388 A1 | 3/2003 | Dennis et al. | |
| 2003/0082566 A1 | 5/2003 | Sylvan | |
| 2003/0100102 A1 | 5/2003 | Rothberg et al. | |
| 2003/0165852 A1 | 9/2003 | Schueler et al. | |
| 2003/0186255 A1 | 10/2003 | Williams et al. | |
| 2003/0194704 A1 | 10/2003 | Penn et al. | |
| 2003/0231791 A1 | 12/2003 | Torre-Bueno et al. | |
| 2004/0137470 A1 | 7/2004 | Dhallan | |
| 2004/0142463 A1 | 7/2004 | Walker et al. | |
| 2004/0144651 A1 | 7/2004 | Huang et al. | |
| 2004/0157243 A1 | 8/2004 | Huang et al. | |
| 2004/0197797 A1 | 10/2004 | Inoko et al. | |
| 2004/0209299 A1 | 10/2004 | Pinter et al. | |
| 2005/0037388 A1 | 2/2005 | Antonarakis et al. | |
| 2005/0042623 A1 | 2/2005 | Ault-Riche et al. | |
| 2005/0049793 A1 | 3/2005 | Paterlini-Brechot | |
| 2005/0061962 A1 | 3/2005 | Mueth et al. | |
| 2005/0064476 A1 | 3/2005 | Huang et al. | |
| 2005/0130217 A1 | 6/2005 | Huang et al. | |
| 2005/0158754 A1 | 7/2005 | Puffenberger et al. | |
| 2005/0196785 A1 | 9/2005 | Quake et al. | |
| 2005/0221341 A1 | 10/2005 | Shimkets et al. | |
| 2005/0244843 A1 | 11/2005 | Chen et al. | |
| 2005/0252773 A1 | 11/2005 | McBride et al. | |
| 2005/0287611 A1 | 12/2005 | Nugent et al. | |
| 2006/0008807 A1 | 1/2006 | O'Hara et al. | |
| 2006/0046258 A1 | 3/2006 | Lapidus et al. | |
| 2006/0051265 A1 | 3/2006 | Mohamed et al. | |
| 2006/0051775 A1 | 3/2006 | Bianchi et al. | |
| 2006/0060767 A1 | 3/2006 | Wang et al. | |
| 2006/0073125 A1 | 4/2006 | Clarke et al. | |
| 2006/0121452 A1 | 6/2006 | Dhallan | |
| 2006/0223178 A1 | 10/2006 | Barber et al. | |
| 2006/0228721 A1 | 10/2006 | Leamon et al. | |
| 2006/0257895 A1 | 11/2006 | Pinkel et al. | |
| 2006/0286558 A1 | 12/2006 | Novoradovskaya et al. | |
| 2007/0059710 A1 | 3/2007 | Luke et al. | |
| 2007/0134658 A1 | 6/2007 | Bohmer et al. | |
| 2007/0178478 A1 | 8/2007 | Dhallan et al. | |
| 2007/0202525 A1 | 8/2007 | Quake et al. | |
| 2007/0207466 A1 | 9/2007 | Cantor et al. | |
| 2007/0212689 A1 | 9/2007 | Bianchi et al. | |
| 2007/0224613 A1 | 9/2007 | Strathmann | |
| 2007/0238105 A1 | 10/2007 | Barrett et al. | |
| 2007/0275402 A1 | 11/2007 | Lo et al. | |
| 2008/0020390 A1 | 1/2008 | Mitchell et al. | |
| 2008/0050739 A1 | 2/2008 | Stoughton et al. | |
| 2008/0064098 A1 | 3/2008 | Allickson | |
| 2008/0070792 A1 | 3/2008 | Stoughton et al. | |
| 2008/0071076 A1 | 3/2008 | Hahn et al. | |
| 2008/0090239 A1 | 4/2008 | Shoemaker et al. | |
| 2008/0096216 A1 | 4/2008 | Quake | |
| 2008/0124721 A1 | 5/2008 | Fuchs | |
| 2008/0138809 A1 | 6/2008 | Kapur et al. | |
| 2008/0193927 A1 | 8/2008 | Mann et al. | |
| 2008/0213775 A1 | 9/2008 | Brody et al. | |
| 2008/0220422 A1 | 9/2008 | Shoemaker et al. | |
| 2008/0299562 A1 | 12/2008 | Oeth et al. | |
| 2009/0026082 A1 | 1/2009 | Rothberg et al. | |
| 2009/0029377 A1 | 1/2009 | Lo et al. | |
| 2009/0053719 A1 | 2/2009 | Lo et al. | |
| 2009/0087847 A1 | 4/2009 | Lo et al. | |
| 2009/0117538 A1 | 5/2009 | Hashimoto et al. | |
| 2009/0170113 A1 | 7/2009 | Quake et al. | |
| 2009/0170114 A1 | 7/2009 | Quake et al. | |
| 2009/0215042 A1 | 8/2009 | Sella-Tavor et al. | |
| 2009/0270601 A1 | 10/2009 | Benner et al. | |
| 2009/0280492 A1 | 11/2009 | Stoughton et al. | |
| 2009/0291443 A1 | 11/2009 | Stoughton et al. | |
| 2009/0299645 A1 | 12/2009 | Colby et al. | |
| 2009/0307181 A1 | 12/2009 | Colby et al. | |
| 2009/0317798 A1 | 12/2009 | Heid et al. | |
| 2009/0317817 A1 | 12/2009 | Oeth et al. | |
| 2009/0317818 A1 | 12/2009 | Ehrich et al. | |
| 2010/0068711 A1 | 3/2010 | Umansky et al. | |
| 2010/0093550 A1 | 4/2010 | Stuelpnagel et al. | |
| 2010/0093835 A1 | 4/2010 | McSwiggen et al. | |
| 2010/0112575 A1 | 5/2010 | Fan et al. | |
| 2010/0112590 A1 | 5/2010 | Lo et al. | |
| 2010/0120038 A1 | 5/2010 | Mir et al. | |
| 2010/0124751 A1 | 5/2010 | Quake et al. | |
| 2010/0124752 A1 | 5/2010 | Quake et al. | |
| 2010/0136529 A1 | 6/2010 | Shoemaker et al. | |
| 2010/0138165 A1 | 6/2010 | Fan et al. | |
| 2010/0167954 A1 | 7/2010 | Earnshaw et al. | |
| 2010/0184075 A1 | 7/2010 | Cantor et al. | |
| 2010/0216151 A1 | 8/2010 | Lapidus et al. | |
| 2010/0216153 A1 | 8/2010 | Lapidus et al. | |
| 2010/0255492 A1 | 10/2010 | Quake et al. | |
| 2010/0255493 A1 | 10/2010 | Quake et al. | |
| 2010/0256013 A1 | 10/2010 | Quake et al. | |
| 2010/0291571 A1 | 11/2010 | Stoughton et al. | |
| 2010/0291572 A1 | 11/2010 | Stoughton et al. | |
| 2010/0304978 A1 | 12/2010 | Deng et al. | |
| 2010/0311064 A1 | 12/2010 | Oliphant et al. | |
| 2011/0003293 A1 | 1/2011 | Stoughton et al. | |
| 2011/0027771 A1 | 2/2011 | Deng et al. | |
| 2011/0105353 A1 | 5/2011 | Lo et al. | |
| 2011/0117548 A1 | 5/2011 | Mitchell et al. | |
| 2011/0171638 A1 | 7/2011 | Stoughton et al. | |
| 2011/0177517 A1 | 7/2011 | Rava et al. | |
| 2011/0201507 A1 | 8/2011 | Rava et al. | |
| 2011/0224087 A1 | 9/2011 | Quake et al. | |
| 2011/0230358 A1 | 9/2011 | Rava | |
| 2011/0245085 A1 | 10/2011 | Rava et al. | |
| 2011/0246083 A1 | 10/2011 | Fan et al. | |
| 2011/0312503 A1 | 12/2011 | Chuu et al. | |
| 2011/0319272 A1 | 12/2011 | Fan et al. | |
| 2012/0003635 A1 | 1/2012 | Lo et al. | |
| 2012/0010085 A1 | 1/2012 | Rava et al. | |
| 2012/0034603 A1 | 2/2012 | Oliphant et al. | |
| 2012/0034685 A1 | 2/2012 | Sparks et al. | |
| 2012/0094849 A1 | 4/2012 | Rava et al. | |
| 2012/0100548 A1 | 4/2012 | Rava et al. | |
| 2012/0135872 A1 | 5/2012 | Chun et al. | |
| 2012/0149582 A1 | 6/2012 | Rava et al. | |
| 2012/0149583 A1 | 6/2012 | Rava et al. | |
| 2012/0165203 A1 | 6/2012 | Quake et al. | |
| 2012/0171666 A1 | 7/2012 | Shoemaker et al. | |
| 2012/0171667 A1 | 7/2012 | Shoemaker et al. | |
| 2012/0183963 A1 | 7/2012 | Stoughton et al. | |
| 2012/0190018 A1 | 7/2012 | Struble et al. | |
| 2012/0208186 A1 | 8/2012 | Kapur et al. | |
| 2012/0208710 A1 | 8/2012 | Fan et al. | |
| 2012/0270739 A1 | 10/2012 | Rava et al. | |
| 2013/0189688 A1 | 7/2013 | Shoemaker et al. | |
| 2013/0210644 A1 | 8/2013 | Stoughton et al. | |
| 2013/0280709 A1 | 10/2013 | Stoughton et al. | |
| 2013/0288242 A1 | 10/2013 | Stoughton et al. | |
| 2013/0288903 A1 | 10/2013 | Kapur et al. | |
| 2013/0295565 A1 | 11/2013 | Shoemaker et al. | |
| 2013/0324418 A1 | 12/2013 | Fuchs et al. | |
| 2014/0051583 A1 | 2/2014 | Fan et al. | |
| 2014/0094373 A1 | 4/2014 | Zimmerman et al. | |
| 2014/0106975 A1 | 4/2014 | Stoughton et al. | |
| 2014/0199691 A1 | 7/2014 | Chuu et al. | |
| 2014/0256560 A1 * | 9/2014 | Lo | G06F 19/18 506/2 |
| 2014/0329691 A1 | 11/2014 | Fan et al. | |
| 2015/0104793 A1 | 4/2015 | Quake et al. | |
| 2015/0218631 A1 | 8/2015 | Chuu et al. | |

FOREIGN PATENT DOCUMENTS

| | | |
|---|---|---|
| EP | 2029778 A2 | 9/2004 |
| EP | 2024512 A2 | 2/2009 |
| EP | 2024513 A2 | 2/2009 |

(56) References Cited

FOREIGN PATENT DOCUMENTS

| | | |
|---|---|---|
| EP | 2029779 A2 | 3/2009 |
| EP | 2334812 A2 | 6/2011 |
| EP | 2366801 A1 | 9/2011 |
| EP | 2385143 A2 | 11/2011 |
| EP | 2423334 A2 | 2/2012 |
| EP | 2548972 A1 | 1/2013 |
| EP | 2562268 A1 | 2/2013 |
| EP | 2589668 A1 | 5/2013 |
| EP | 1981995 B1 | 7/2013 |
| WO | WO 98/44151 A1 | 10/1998 |
| WO | WO 99/22868 A1 | 5/1999 |
| WO | WO 00/18957 A1 | 4/2000 |
| WO | WO 00/40750 A1 | 7/2000 |
| WO | WO 2000/58507 A1 | 10/2000 |
| WO | WO 03/020986 A1 | 3/2003 |
| WO | WO 2003/020974 A2 | 3/2003 |
| WO | WO 2003/020974 A3 | 9/2003 |
| WO | WO 2004/029221 A2 | 4/2004 |
| WO | WO 2004/065629 A1 | 8/2004 |
| WO | WO 2004/113877 A1 | 12/2004 |
| WO | WO 2005/035725 A2 | 4/2005 |
| WO | WO 2005/039389 A1 | 5/2005 |
| WO | WO 2005/047532 A1 | 5/2005 |
| WO | WO 2005/118852 A2 | 12/2005 |
| WO | WO 2006/010610 A2 | 2/2006 |
| WO | WO 2005/118852 A3 | 3/2006 |
| WO | WO 2006/010610 A3 | 6/2006 |
| WO | WO 2006/097049 A1 | 9/2006 |
| WO | WO 2007/044091 A2 | 4/2007 |
| WO | WO 2007/075836 A2 | 7/2007 |
| WO | WO 2007/092473 A2 | 8/2007 |
| WO | WO 2007/100911 A2 | 9/2007 |
| WO | WO 2007/044091 A3 | 11/2007 |
| WO | WO 2007/100911 A3 | 11/2007 |
| WO | WO 2007/132166 A2 | 11/2007 |
| WO | WO 2007/132167 A2 | 11/2007 |
| WO | WO 2007/147018 A1 | 12/2007 |
| WO | WO 2007/147073 A2 | 12/2007 |
| WO | WO 2007/147074 A2 | 12/2007 |
| WO | WO 2007/147076 A2 | 12/2007 |
| WO | WO 2007/147079 A2 | 12/2007 |
| WO | WO 2007/075836 A3 | 2/2008 |
| WO | WO 2007/132166 A3 | 2/2008 |
| WO | WO 2007/147079 A3 | 3/2008 |
| WO | WO 2007/147076 A3 | 4/2008 |
| WO | WO 2008/045158 A1 | 4/2008 |
| WO | WO 2007/132167 A3 | 5/2008 |
| WO | WO 2007/147073 A3 | 5/2008 |
| WO | WO 2007/147074 A3 | 5/2008 |
| WO | WO 2008/111990 A1 | 9/2008 |
| WO | WO 2007/092473 A3 | 11/2008 |
| WO | WO 2009/013492 A1 | 1/2009 |
| WO | WO 2009/013496 A1 | 1/2009 |
| WO | WO 2009/019455 A2 | 2/2009 |
| WO | WO 2009/032781 | 3/2009 |
| WO | WO 2009/019455 A3 | 4/2009 |
| WO | WO 2010/033578 A2 | 3/2010 |
| WO | WO 2010/045617 A2 | 4/2010 |
| WO | WO 2010/033578 A3 | 5/2010 |
| WO | WO 2010/085815 A1 | 7/2010 |
| WO | WO 2011/014741 A1 | 2/2011 |
| WO | WO 2011/051283 A1 | 5/2011 |
| WO | WO 2011/090556 A1 | 7/2011 |
| WO | WO 2011/090557 A1 | 7/2011 |
| WO | WO 2011/090558 A1 | 7/2011 |
| WO | WO 2011/090559 A1 | 7/2011 |
| WO | WO 2011/091046 A1 | 7/2011 |
| WO | WO 2011/091063 A1 | 7/2011 |
| WO | WO 2011/094646 A1 | 8/2011 |
| WO | WO 2011/102998 A2 | 8/2011 |
| WO | WO 2012/019187 A2 | 2/2012 |
| WO | WO 2012/019193 A2 | 2/2012 |
| WO | WO 2012/019198 A2 | 2/2012 |
| WO | WO 2012/019200 A2 | 2/2012 |

OTHER PUBLICATIONS

Advisory action dated Dec. 16, 2013 for U.S. Appl. No. 12/751,940.
Allard, et al. Tumor cells circulate in the peripheral blood of all major carcinomas but not in healthy subjects or patients with nonmalignant diseases. Clin Cancer Res. Oct. 15, 2004;10(20):6897-904.
Amended Joint Claim Construction Chart and Statement dated May 13, 2010, in *Life Technologies Corporation, et al.* v. *Illumina, et al.*, 1:09-cv-00706-RK, United States District of Delaware, May 13, 2010.
Amended Joint Claim Construction Chart and Statement dated May 13, 2010, in *Life Technologies Corporation, et al.* v. *Illumina, et al.*, 1:09-cv-00706-RK, United States District of Delaware.
Amended Scheduling Order. *Ariosa Diagnostics* v. *Verinata Health*. Case IPR2013-00276 and IPR2013-00277. U.S. Pat. No. 8,318,430 B2. Nov. 19, 2013. 6pages.
Amendment and response to final office action. Methods of fetal abnormality, dated Aug. 31, 2012. 18pages.
Appeal No. 2015-1073: *Schott Gemtron Corp.* v. *SSW Holding Company Inc.*—Corrected Brief for Intervenor—Director of the United States Patent and Trademark Office; filed Apr. 9, 2015.
Appendix A. Atul J Butte. Dec. 16, 2013. 22pages.
Applicant's Amendment and Response filed for Non-Final Office Action re U.S. Appl. No. 11/701,686 dated Jun. 17, 2009.
Ariosa Diagnostics and Sonic Germany Laboratories. Ariosa Diagnostics and Sonic Germany Laboratories announce new partnership to offer pregnant women the harmony prenatal test in Germany. Berlin. Dec. 5, 2013. 2pages.
Ariosa Diagnostics Exhibit List. *Ariosa Diagnostics* v. *Verinata Health*. Case IPR2013-00277. U.S. Pat. No. 8,318,430. Apr. 3, 2014. 6pages.
Ariosa Diagnostics Exhibit List. *Ariosa Diagnostics* v. *Verinata Health*. Case IPR2013-00277. U.S. Pat. No. 8,318,430. May 27, 2014. 6pages.
Ariosa Diagnostics exhibit list. *Ariosa Diagnostics* v. *Verinata Health*. IPR2013-00276. U.S. Pat. No. 8,318,430. Apr. 3, 2014. 6pages.
Ariosa Diagnostics exhibit list. *Ariosa Diagnostics* v. *Verinata Health*. IPR2013-00276. U.S. Pat. No. 8,318,430. May 27, 2014. 6pages.
Ariosa Diagnostics Notice of Deposition of Atul J. Butte. *Ariosa Diagnostics* v. *Verinata Health*. Case IPR2013-00276 IPR2013-00277. U.S. Pat. No. 6,258,540. Feb. 20, 2014. 3pages.
Ariosa Diagnostics Submission of Substitute Exhibits. *Ariosa Diagnostics* v. *Verinata Health*. Case IPR2013-00277. U.S. Pat. No. 8,318,430. Mar. 31, 2014. 3pages.
Ariosa Diagnostics' submission of substitute exhibits. *Ariosa Diagnostics* v. *Verinata Health*. IPR2013-00276. U.S. Pat. No. 8,318,430. Mar. 31, 2014. 3 pages.
Ariosa Diagnostics updated exhibit list. *Ariosa Diagnostics* v. *Verinata Health*. Case IPR2013-00277. U.S. Pat. No. 8,318,430. Jul. 14, 2014. 6pages.
Ariosa diagnostics updated exhitbit list. *Ariosa Diagnostics* v. *Verinata Health*. IPR2013-00276. U.S. Pat. No. 8,318,430. Jul. 14, 2014. 6pages. Jul. 14, 2014.
Ariosa Diagnostics, Inc. and Laboratory Corporation of America Holdings' Responsive Claim Construction Brief for U.S. Pat. No. 8,296,076 and U.S. Pat. No. 8,318,430 dated Jul. 3, 2013.
Ariosa Diagnostics, Inc. Ariosa Diagnostics provides harmony prenatal test to over 40,000 women and expands into more than 50 countries in the third quarter of 2013. San Jose, Calif. Nov. 13, 2013. 2pages.
Ariosa Diagnostics, Inc. Ariosa Diagnostics selected as NIPT service provider in majority of california comprehensive prenatal diagnosis centers throughout the state. San Jose, Calif. Nov. 1, 2013. 1page.
Ariosa Diagnostics. Ariosa Diagnostics Announces Nationwide Launch of the Harmony Prenatal Test Through LabCorp. San Jose, Calif., May 7, 2012. 2pages.
Ariosa exhibit list. IPR2013-00276. 5pages. Mar. 31, 2014.
Ariosa Exhibit List. IPR2013-00277. Mar. 31, 2014. 4pages.

(56) References Cited

OTHER PUBLICATIONS

Ariosa. About the science. http://www.ariosadx.com/about-the-science/ accessed on Jan. 14, 2014. 2pages.
Ariosa. Brochure Harmony Prenatal Test. 2013. 4pages.
Ashoor et al. Trisomy 13 detection in the first trimester of pregnancy using a chromosome-selective cell-free DNA analysis method. Ultrasound Obstet Gynecol. Jan. 2013;41(1):21-5. doi: 10.1002/uog.12299. Epub Nov. 23, 2012.
Bennett, et al. Toward the 1,000 dollars human genome. Pharmacogenomics. 2005; 6(4):373-82.
Bentley, et al. Accurate whole human genome sequencing using reversible terminator chemistry. Nature. Nov. 6, 2008;456(7218):53-9.
Binladen, et al. The use of coded PCR primers enables high-throughput sequencing of multiple homolog amplification products by 454 parallel sequencing. PLoS One. Feb. 14, 2007;2(2):e197.
Bode, et al. Mutations in the tyrosine kinase domain of the EGFR gene are rare in synovial sarcoma. Mod Pathol. Apr. 2006;19(4):541-7.
Bookout, et al. High-throughput real-time quantitative reverse transcription PCR. Curr. Prot. Mol. Biol. 2005; 15.8.1-15.8.21.
Botezatu, et al. Genetic analysis of DNA excreted in urine: a new approach for detecting specific genomic DNA sequences from cells dying in an organism. Clin Chem. Aug. 2000;46(8 Pt 1):1078-84.
Bustamante-Aragones, et al. Detection of a Paternally Inherited Fetal Mutation in Maternal Plasma by the Use of Automated Sequencing. Ann. N.Y. Acad. Sci. 1075: 108-117 (2006), pp. 108-117, XP-002652985.
Butler, et al. The development of reduced size STR amplicons as tools for analysis of degraded DNA. J Forensic Sci. Sep. 2003;48(5):1054-64.
Butler. Short tandem repeat typing technologies used in human identity testing. Biotechniques. Oct. 2007;43(4):ii-v.
Bybee, et al. Targeted amplicon sequencing (TAS): a scalable next-gen approach to multilocus, multitaxa phylogenetics. Genome Biol Evol. 2011;3:1312-23. doi: 10.1093/gbe/evr106. Epub Oct. 13, 2011.
Cappuzzo, et al. Epidermal growth factor receptor gene and protein and gefitinib sensitivity in non-small-cell lung cancer. J Natl Cancer Inst. May 4, 2005;97(9):643-55.
Chamberlain, et al. Deletion screening of the Duchenne muscular dystrophy locus via multiplex DNA amplification. Nucleic Acids Res. Dec. 9, 1988;16(23):11141-56.
Chan, et al. Size distributions of maternal and fetal DNA in maternal plasma. Clin Chem. Jan. 2004;50(1):88-92.
Chen, et al. Microsatellite alterations in plasma DNA of small cell lung cancer patients. Nat Med. Sep. 1996;2(9):1033-5.
Chetverin et al. Oligonucleotide arrays: new concepts and possibilities. Biotechnology (N Y). Nov. 1994;12(11):1093-9.
Chiu, et al. Maternal plasma DNA analysis with massively parallel sequencing by ligation for noninvasive prenatal diagnosis of trisomy 21. Clin Chem. Mar. 2010;56(3):459-63.
Chiu, et al. Non-invasive prenatal assessment of trisomy 21 by multiplexed maternal plasma DNA sequencing: large scale validity study. BMJ. Jan. 11, 2011;342:c7401.
Chiu, et al. Non-invasive prenatal diagnosis by single molecule counting technologies. Trends Genet. Jul. 2009;25(7):324-31.
Chiu, et al. Noninvasive prenatal diagnosis of fetal chromosomal aneuploidy by massively parallel genomic sequencing of DNA in maternal plasma. Proc Natl Acad Sci U S A. Dec. 23, 2008;105(51):20458-63.
Choesmel, et al. Enrichment methods to detect bone marrow micrometastases in breast carcinoma patients: clinical relevance. Breast Cancer Res. 2004;6(5):R556-569.
Chu, et al. Statistical model for whole genome sequencing and its application to minimally invasive diagnosis of fetal genetic disease. Bioinformatics. May 15, 2009;25(10):1244-50.
Claim Chart for the First Ground of Rejection: *Dhallan II* v. *Craig and Illumina Brochure* in Reexamination No. 90/013,678, filed Jan. 8, 2016.
Claim Chart for the Second Ground of Rejection: *Dhallan II* v. *Parameswaran and Hamady* in Reexamination No. 90/013,678, filed Jan. 8, 2016.
Claim Chart for the Third Ground of Rejection: *Dhallan I* v. *Binladen* in Reexamination No. 90/013,678, filed Jan. 8, 2016.
Claim Construction Order dated Oct. 16, 2013 for Case Nos. C 11-06391 SI, C 12-00132 SI, C 12-00865 SI, C 12-05501 SI.
Coble, et al. Characterization of new miniSTR loci to aid analysis of degraded DNA. J Forensic Sci. Jan. 2005;50(1):43-53.
Collins, et al. A vision for the future of genomics research. Nature. Apr. 24, 2003;422(6934):835-47. Epub Apr. 14, 2003.
Craig, et al. Identification of genetic variants using bar-coded multiplexed sequencing. Nat Methods. Oct. 2008;5(10):887-93. doi: 10.1038/nmeth.1251. Epub Sep. 14, 2008.
Cristofanilli, et al. Circulating tumor cells revisited. JAMA. 2010; 303(11):1092-1093.
Cristofanilli, et al. Circulating tumor cells, disease progression, and survival in metastatic breast cancer. N Engl J Med. Aug. 19, 2004;351(8):781-91.
Curriculum Vitae of Cynthia Casson Morton. IPR2013-200276. Jan. 2013. 68pages.
Curriculum Vitae of Cynthia Casson Morton. IPR2013-200277. Jan. 2013. 68pages.
Curriculum Vitae of Robert Luke Nussbaum. IPR2013-200276. Mar. 31, 2014. 43pages.
Curriculum Vitae of Robert Luke Nussbaum. IPR2013-200277. Mar. 31, 2014. 43pages.
Daines, et al. High-throughput multiplex sequencing to discover copy number variants in *Drosophila*. Genetics. Aug. 2009;182(4):935-41. doi: 10.1534/genetics.109.103218. Epub Jun. 15, 2009.
De Luca, et al. Detection of circulating tumor cells in carcinoma patients by a novel epidermal growth factor receptor reverse transcription-PCR assay. Clin Cancer Res. Apr. 2000;6(4):1439-44.
Decision Denying Institution of Inter Partes Review: IPR2015-00873—U.S. Pat. No. 7,879,828 (*Apotex* v. *Wyeth*), entered Sep. 16, 2015.
Decision: Institution of inter partes review. *Ariosa Diagnostics* v. *Verinata Health*. IPR2013-00276. U.S. Pat. No. 8,318,430 B2.Oct. 25, 2013. 23pages.
Decision: Institution of Inter Partes Review. *Ariosa Diagnostics* v. *Verinata Health*. IPR2013-00277. U.S. Pat. No. 8,318,430 B2.Oct. 25, 2013. 23pages.
Declaration of Atul J. Butte in support of patent owners response to inter partes review. IPR2013-00276. Jan. 16, 2014. 90pages.
Declaration of Atul J. Butte in support of patent owners response to inter partes review. IPR2013-00277. Jan. 16, 2014. 90pages.
Declaration of Cynthia Casson Morton in re: Chuu, et al. (replacement), Methods of Fetal Abnormality Detection. Mar. 10, 2014. 98pages.
Declaration of Cynthia Casson Morton in re: Chuu, et al., U.S. Pat. No. 8,318,430. Methods of Fetal Abnormality Detection. Part 1. May 10, 2013. 292pages.
Declaration of Cynthia Casson Morton in re: Chuu, et al., U.S. Pat. No. 8,318,430. Methods of Fetal Abnormality Detection. Part 3. May 10, 2013. 153pages.
Declaration of Cynthia Casson Morton. In re: Chuu, et al, U.S. Pat. No. 8,318,430. Mar. 31, 2014. 89pages. Replacement.
Declaration of Cynthia Casson Morton. In re: Chuu, et al, U.S. Pat. No. 8,318,430. May 10, 2013. 138pages. Part 2.
Declaration of Cynthia Casson Morton. In re: Chuu, et al, U.S. Pat. No. 8,318,430. IPR2013-00277. May 10, 2013. 283pages. Part 1.
Declaration of Dr. Steven Rosenberg dated Jan. 7, 2016.
Declaration of Robert Nussbaum in re Parent of: Fan et al. Methods of Fetal Abnormality Detection. Mar. 31, 2014. 67pages.
Declaration of Robert Nussbaum in re Parent of: Fan et al. Methods of Fetal Abnormality Detection. May 10, 2013. 128pages.
Declaration of Robert Nussbaum. Dated Apr. 16, 2013. In re Patent of: Fan, et al. U.S. Pat. No. 8,318,430, claims 1-18.
Declaration of Robert Nussbaum. In re patent of: Chuu et al. Mar. 31, 2014. 60pages.
Declaration of Robert Nussbaum. In re patent of: Chuu et al. May 8, 2013. 139pages.

(56) References Cited

OTHER PUBLICATIONS

Deposition of Cynthia Casson Morton transcript. *Ariosa Diagnostics* v. *The board of thrustees of the Leland Sanford Junior University*. IPR2013-00308. U.S. Pat. No. 8,296,076. Jan. 17, 2014. 100pages.
Deposition of Cynthia Casson Morton transcript. *Ariosa Diagnostics* v. *Verinata Health*. IPR2013-00277 IPR2013-00276. Dec. 10, 2013. 115pages.
Deposition of Robert Nussbaum transcript. *Ariosa Diagnostics* v. *Verinata Health*. IPR2013-00277 IPR2013-00276. Dec. 11, 2013. 115pages.
Dhallan, et al. A non-invasive test for prenatal diagnosis based on fetal DNA present in maternal blood: a preliminary study. Lancet. Feb. 10, 2007;369(9560):474-81.
Dixon, et al. Analysis of artificially degraded DNA using STRs and SNPs—results of a collaborative European (EDNAP) exercise. Forensic Sci Int. Dec. 1, 2006;164(1):33-44.
Dohm, et al. Substantial biases in ultra-short read data sets from high-throughput DNA sequencing. Nucleic Acids Res. Sep. 2008;36(16):e105. doi: 10.1093/nar/gkn425. Epub Jul. 26, 2008.
Dragovich, et al. Anti-EGFR-targeted therapy for exophageal and gastric cancers: an evolving concept. Journal of Oncology. 2009; vol. 2009, Article ID 804108.
Dressman, et al. "Transforming single DNA molecules into fluorescent magnetic particles for detection and enumeration of genetic variations." PNAS, Jul. 2003, vol. 100. No. 15, 8817-8822.
Edwards, et al. Multiplex PCR: advantages, development, and applications. PCR Methods Appl. Feb. 1994;3(4):S65-75.
Ehrich, et al. Noninvasive detection of fetal trisomy 21 by sequencing of DNA in maternal blood: a study in a clinical setting. Am J Obstet Gynecol. Mar. 2011;204(3):205.e1-11.
Email: RE: deposition in IPR2013-00276/277. Email from Greg Gardella to Michael Rosato. Apr. 11, 2014. 4pages.
Erlich, et al. Recent advances in the polymerase chain reaction. Science. Jun. 21, 1991;252(5013):1643-51.
Errata. *Ariosa Diagnostics* v. *Verinata Health*. Case IPR2013-00276. U.S. Pat. No. 8,318,430 B2. Oct. 28, 2013. 2pages.
Errata. *Ariosa Diagnostics* v. *Verinata Health*. Case IPR2013-00277. U.S. Pat. No. 8,318,430 B2. Oct. 28, 2013. 2pages.
Error-correcting barcoded primers allow hundreds of samples to be pyrosequenced in multiplex, Hamady, et al., Nat. Methods, 5(3):235-37 (2008) ("Hamady").
European office action dated Mar. 3, 2009 for EP07763674.4.
European office action dated Jun. 26, 2012 for EP Application No. 11159371.1.
European office action dated Aug. 22, 2013 for EP Application No. 07798579.4.
European office action dated Oct. 8, 2012 for EP Application No. 11175845.
European office action dated Dec. 13, 2013 for EP Application No. 11159371.1.
European office action dated Dec. 16, 2013 for EP Application No. 12175907.
European office action dated Dec. 18, 2012 for EP Application No. 11159371.1.
European office action dated Dec. 21, 2010 for EP07763674.4.
European Patent Office Communication dated Mar. 16, 2012 in EP App. No. 10830938.6 (EP Publication No. 2366031) with pending claims, 9 pages.
European Patent Office Communication dated Mar. 16, 2012 in EP App. No. 10830939.4 (EP Publication No. 2376661) with pending claims, 9 pages.
European Patent Office Communication dated Mar. 19, 2012 in EP App. No. 10825822.9 (EP Publication No. 2370599) with pending claims, 10 pages.
European search report and search opinion dated Jan. 2, 2013 for EP Application No. 12175907.0.
European search report and search opinion dated Jan. 25, 2013 for EP Application No. 09815105.3.
European search report and search opinion dated Mar. 16, 2012 for EP Application No. 11182181.
European search report and search opinion dated Apr. 9, 2013 for EP Application No. 12180149.2.
European search report and search opinion dated Jul. 31, 2009 for EP07763674.4.
European search report and search opinion dated Nov. 17, 2011 for EP Application No. 11175845.
European search report and search opinion dated Nov. 9, 2009 for Application No. 7784442.1.
European search report and search opinion dated Dec. 21, 2009 for Application No. 07798579.4.
European search report and search opinion dated Dec. 22, 2009 for Application No. 07798580.2.
European search report and search opinion dated Dec. 22, 2009 for Application No. 07784444.7.
European search report dated Jan. 25, 2013 for EP Application No. 12183946.8.
European Supplementary Search Report for EP App. No. 10825822.9 (EP Publication No. 2370599), dated Feb. 22, 2012, 4 pages.
European Supplementary Search Report for EP App. No. 10830938.6 (EP Publication No. 2366031), dated Feb. 22, 2012, 4 pages.
European Supplementary Search Report for EP App. No. 10830939.4 (EP Publication No. 2376661), dated Feb. 22, 2012, 4 pages.
Exhibit C: Ariosa's proposed constructions and intrinsic and extrinsic evidence. Filed Jul. 3, 2013.
Exhibit E to joint claim construction chart for '540 patent. Filed Jul. 3, 2013.
Exhibit Q, Printout of http://www.nature.com/nmeth/journal/v5/n10/full/nmeth.1251.html displaying Abstract of Craig et al., Identification of genetic variants using bar-coded multiplexed sequencing 5 Nature Methods 887-893 (2008), accessed Dec. 30, 2015, 3 pages.
Exhibit R, Printout of http://www.nature.com/nmeth/journal/v5/n3/full/nmeth.1184.html displaying Abstract of Hamady et al., Error-correcting barcoded primers for pyrosequencing hundreds of samples in multiplex 5 Nature Methods 235-237 (2008), accessed Dec. 30, 2015, 3 pages.
Exhibit S, Printout of http://www.nar.oxfordjournals.org/content/35/19/e130.full displaying Parameswaran et al., A pyrosequencing-tailored nucleotide barcode design unveils opportunities for large-scale sample multiplexing 35(19) Nucleic Acids Research e130 (2007), accessed Dec. 30, 2015, 17 pages.
Extended European Search Report for Application No. 11159371 dated Aug. 10, 2011, 10 pages.
Fan, et al. Analysis of the size distributions of fetal and maternal cell-free DNA by paired-end sequencing. Clin Chem. Aug. 2010;56(8):1279-86.
Fan, et al. Detection of aneuploidy with digital polymerase chain reaction. Anal Chem. Oct. 1, 2007;79(19):7576-9.
Fan, et al. Highly parallel genomic assays. Nat Rev Genet. Aug. 2006;7(8):632-44.
Fan, et al. In principle method for noninvasive determination of the fetal genome. Nature Precedings: Nature Precedings 10.1038/npre.2010.5373.1 . 2010.
Fan, et al. Microfluidic digital PCR enables rapid prenatal diagnosis of fetal aneuploidy. Am J Obstet Gynecol. May 2009;200(5):543.e1-7.
Fan, et al. Noninvasive diagnosis of fetal aneuploidy by shotgun sequencing DNA from maternal blood. Proc Natl Acad Sci U S A. Oct. 21, 2008;105(42):16266-71.
Fan, et al. Sensitivity of noninvasive prenatal detection of fetal aneuploidy from maternal plasma using shotgun sequencing is limited only by counting statistics. PLoS One. May 3, 2010;5(5):e10439.
Fan, et al. Single cell degenerate oligonucleotide primer-PCR and comparative genomic hybridization with modified control reference. Journal of Ahejian University—Science A. 2001; 2(3):318-321.
Fan, et al. Whole Genome Molecular Haplotyping of Single Cells. Nat Biotechnol. Jan. 2011;29(1):51-7.
Federal Circuit Judgment and Order Vacating the Final Written Decisions in IPR2013-00276 and IPR2013-00277; Opinion filed and Judgment entered Nov. 16, 2015.

(56) References Cited

OTHER PUBLICATIONS

Federal Circuit Mandate Entering the Judgment and Order in Case No. 15/1215, entered Nov. 16, 2015 and filed Dec. 23, 2015.
Feinberg, et al. A technique for radiolabeling DNA restriction endonuclease fragments to high specific activity. Anal Biochem. Jul. 1, 1983;132(1):6-13.
File History for Inter Partes Review of claims 1-18 of the '430 patent (IPR2013-00276), Opinion filed and Judgement entered Nov. 16, 2015.
File History for Inter Partes Review of claims 19-30 of the '430 patent (IPR2013-00277), Opinion filed and Judgement entered Nov. 16, 2015.
First Amended Complaint for Patent Infringement dated Nov. 29, 2012 for Case No. 3:12-cv-05501-SI.
First petition for inter partes review. *Ariosa Diagnostics* v. *Verinata Health*. U.S. Pat. No. 8,318,430. Claims 1-18. May 10, 2013. 61pages.
Gardella, et al. Second Petition for Inter Partes Review Under 35 U.S.C. §§ 311319 and 37 C.F.R. § 42.100 ET SEQ.(Claims 19-30). Dated May 10, 2013, for U.S. Pat. No. 8,318,430.
Gardella, G. First Petition for Inter Partes Review Under 35 U.S.C. §§ 311-319 and 37 C.F.R. § 42.100 ET SEQ. (Claims 1-18). Dated May 10, 2013. U.S. Pat. No. 8,318,430.
Genomeweb. Launch of PacBio RS Platform Drives Pacific Biosciences Q2 Revenues to $10.6M. http://www.genomeweb.com/sequencing/launch-pacbio-rs-platform-drives-pacific-biosciences-q2-revenues-106m. Aug. 5, 2011. Accessed Jan. 14, 2014. 4pages.
Ghanta, et al. Non-invasive prenatal detection of trisomy 21 using tandem single nucleotide polymorphisms. PLoS One. Oct. 8, 2010;5(10):e13184.
Grubweiser, et al. A new miniSTR-mulitplex displaying reduced amplicon lengths for the analysis of degraded DNA. Int J Legal Med. Mar. 2006;120(2):115-20.
Guatelli, et al. Isothermal, in vitro amplification of nucleic acids by a multienzyme reaction modeled after retroviral replication. Proc Natl Acad Sci U S A. Mar. 1990;87(5):1874-8.
Hahn, et al. Microsystem for isolation of fetal DNA from maternal plasma by preparative size separation. Clin Chem. Dec. 2009;55(12):2144-52. doi: 10.1373/clinchem.2009.127480. Epub Oct. 1, 2009.
Hamabe, et al. Molecular study of the Prader-Willi syndrome: deletion, RFLP, and phenotype analyses of 50 patients. Am J Med Genet. Oct. 1, 1991;41(1):54-63.
Hanson, et al. Whole genome amplification strategy for forensic genetic analysis using single or few cell equivalents of genomic DNA. Anal Biochem. Nov. 15, 2005;346(2):246-57.
Harris, et al. Single-molecule DNA sequencing of a viral genome. Science. Apr. 4, 2008;320(5872):106-9.
Harrison, et al. Polymer-stimulated ligation: enhanced ligation of oligo- and polynucleotides by T4 RNA ligase in polymer solutios. Nucleic Acids Res. Nov. 12, 1984;12(21):8235-51.
Hayashi, et al. Regulation of inter- and intramolecular ligation with T4 DNA ligase in the presence of polyethylene glycol. Nucleic Acids Res. Oct. 10, 1986;14(19):7617-31.
Hill, et al. "Characterization of 26 new miniSTR loci" Poster #44—17th International Symposium on Human Identification, Nashville, TN, Oct. 10-12, 2006.
Hong, et al. A nanoliter-scale nucleic acid processor with parallel architecture. Nat. Biotechnol. 2004; 22(4):435-9.
Hosono, et al. Unbiased whole-genome amplification directly from clinical samples. Genome Res. May 2003;13(5):954-64.
Houghton Mifflin Company. The American Heritage Dictionary of the English Language, Fifth Edition. 222 Berkeley Street, Boston MA 02116. Word being defined: Select. 2011; 1588.
Houghton Mifflin Company. The American Heritage Dictionary of the English Language, Fourth Edition. 222 Berkeley Street, Boston, MA 02116. 2006; 1588.
Houghton Mifflin Company. The American Heritage Dictionary of the English Language, Fourth Edition. 222 Berkeley Street, Boston, MA 02116. 2006; 734.

Huang, et al. Isolation of cell-free DNA from maternal plasma using manual and automated systems. Methods Mol Biol. 2008;203-8.
Hung, et al. Detection of circulating fetal nucleic acids: a review of methods and applications. J Clin Pathol. Apr. 2009;62(4):308-13.
Huse, et al. Accuracy and quality of massively parallel DNA pyrosequencing. Genome Biol. 2007;8(7):R143.
Hviid, T. In-cell polymerase chain reaction: strategy and diagnostic applications. Methods Mol Biol. 2006;336:45-58.
Identification of Genetic Variants Using Barcoded Multiplexed Sequencing, Nat. Methods, Craig et al., Nat. Methods, 5(10):887-93 (2008) ("Craig").
Illumina Brochure "Multiplexed Sequencing with the Illumina Genome Analyzer System", Copyright 2008 ("Illumina Brochure").
Illumina, Inc. Multiplexed Sequencing with Illumina Genome Analyzer System. 2008. Pub. No. 770-2008-011. Dec. 2, 2008. 4pages.
Illumina. Preparing samples for CHIP sequencing of DNA. Epub at grcf.jhmi.edu/hts/protocols/11257047_ChIP_Sample_Prep.pdf. 2007.
Infringement Contentions. Verinata and Stanford's patent L.R. 3-1 disclosure of asserted claims and preliminary infringement contentions for U.S. Pat. No. 8,296,076, and U.S. Pat. No. 8,318,430; patent local rule 3-2 document production. Jury trial demanded. *Verinata Health and The Board of trustees of the Leland Stanford junior university* v. *Ariosa Diagnostics and Laboratory Corporation of America Holdings*. Case No. 3:12-cv-05501-SI. Jan. 2, 2013.
International preliminary report on patentability dated Oct. 29, 2008 for PCT/US2007/003209.
International Preliminary Report on Patentability dated Dec. 16, 2008 for PCT Application No. US2007/071247.
International Preliminary Report on Patentability dated Dec. 16, 2008 for PCT Application No. US2007/071248.
International Preliminary Report on Patentability dated Dec. 16, 2008 for PCT Application No. US2007/071256.
International search report dated Feb. 25, 2008 for PCT Application No. US2007/71248.
International search report and written opinion dated Feb. 28, 2011 for PCT Application No. US10/58606.
International search report and written opinion dated Mar. 1, 2011 for PCT Application No. US10/58614.
International search report and written opinion dated Apr. 4, 2011 for PCT Application No. US10/58609.
International search report and written opinion dated Apr. 11, 2011 for PCT Application No. US11/21729.
International search report and written opinion dated Mar. 16, 2010 for PCT Application No. US2009/57136.
International Search Report and Written Opinion dated Sep. 18, 2008 for PCT/US2007/003209.
International search report dated Jan. 16, 2008 for PCT Application No. US2007/71247.
International search report dated Jan. 25, 2008 for PCT Application No. US2007/71250.
International search report dated Feb. 25, 2008 for PCT Application No. US2007/71148.
International search report dated May 19, 2011 for PCT/US2010/058612.
International search report dated Nov. 15, 2007 for PCT Application No. US2007/71149.
International search report dated Nov. 26, 2007 for PCT Application No. US2007/71256.
International. The International HapMap Project. Nature. 2003; 426:789-96.
Ishikawa, et al. Allelic dosage analysis with genotyping microarrays. Biochem Biophys Res Commun. Aug. 12, 2005;333(4):1309-14.
Jama, et al. Quantification of Cell-Free Fetal DNA Levels in Maternal Plasma by STR Analysis. ACMG Annual Clinical Genetics Meeting Poster 398; Mar. 24-28, 2010. Available online at http://acmg.omnibooksonline.com/2010/data/papers/398.pdf and http://acmg.omnibooksonline.com/2010/index.html.
Jiang, et al. Old can be new again: HAPPY whole genome sequencing, mapping and assembly. Int J Biol Sci. 2009;5(4):298-303. Epub Apr. 15, 2009.
Joint Claim Construction and Prehearing Statement dated May 3, 2013 for Case No. 3:12-cv-05501-SI.

(56) References Cited

OTHER PUBLICATIONS

Joint stipulation regarding due dates 1 and 2. *Ariosa Diagnostics* v. *Verinata Health*. Case IPR2013-00276. U.S. Pat. No. 8,318,430. Jan. 6, 2014. 5pages.
Joint stipulation regarding due dates 1 and 2. *Ariosa Diagnostics* v. *Verinata Health*. Case IPR2013-00277. U.S. Pat. No. 8,318,430. Jan. 6, 2014. 5pages.
Joint Stipulation regarding due dates. *Ariosa Diagnostics* v. *Verinata Health*. Case IPR2013-00276. U.S. Pat. No. 8,318,430. Apr. 1, 2014. 3pages.
Joint Stipulation regarding due dates. *Ariosa Diagnostics* v. *Verinata Health*. Case IPR2013-00277. U.S. Pat. No. 8,318,430. Apr. 1, 2014. 3pages.
Jorgez, et al. Improving enrichment of circulating fetal DNA for genetic testing: size fractionation followed by whole gene amplification. Fetal Diagn Ther. 2009;25(3):314-9.
Ju, et al. Four-color DNA sequencing by synthesis using cleavable fluorescent nucleotide reversible terminators. Proc Natl Acad Sci USA. 2006; 103(52):19635-19640.
Kartalov et al.: "Microfluidic device reads up to four consecutive base pairs in DNA sequencing-by-synthesis.", Nucleic Acids Research, 2004, vol. 32, No. 9, 2004, pp. 2873-2879, XP-002652987.
Kazakov, et al. Extracellular DNA in the blood of pregnant women. Tsitologiia. 1995;37(3):232-6.
Kidd, et al. Developing a SNP panel for forensic identification of individuals. Forensic Sci Int. Dec. 1, 2006;164(1):20-32.
Kimura, et al. Deletional mutant EGFR detected in circulating tumor-derived DNA from lung cancer patients treated with gefitinib. American Association for Cancer Research 96th Annual Meeting. Apr. 16-20, 2005. Abstract 479.
Kircher, et al. High-throughput DNA sequencing—concepts and limitations. Bioessays. Ju. 2010;32(6):524-36. doi: 10.1002/bies.200900181.
Klein, et al. Comparative genomic hybridization, loss of heterozygosity, and DNA sequence analysis of single cells. Proc Natl Acad Sci U S A. 1999; 96(8):4494-9.
Kobayashi, et al. EGFR mutation and resistance of non-small-cell lung cancer to gefitinib. N Engl J Med. Feb. 24, 2005;352(8):786-92.
Koide, et al. Fragmentation of cell-free fetal DNA in plasma and urine of pregnant women. Prenat Diagn. Jul. 2005;25(7):604-7.
Korenberg, et al. Down syndrome phenotypes: the consequences of chromosomal imbalance. PNAS 1994; 91:4997-5001.
Kozarewa, et al. Amplification-free Illumina sequencing-library preparation facilitates improved mapping and assembly of GB-biased genomes. Nat Methods. Apr. 2009;6(4):291-5.
Krivacic, et al. A rare-cell detector for cancer. PNAS. 2004;101:10501-10504.
Lander, et al. Initial sequencing and analysis of the human genome. Nature. Feb. 15, 2001;409(6822):860-921.
Lazinski, et al. Modified protocol for Illumina paired-end library construction. Available online at http://genomics.med.tufts.edu/documents/htseq_protocol_for_illumina_paired.pdf Accessed Jun. 21, 2011.
Leon, et al. Free DNA in the serum of cancer patients and the effect of therapy. Cancer Res. Mar. 1977;37(3):646-50.
Leutwyler, K. Mapping Chromosome 21. Available at http://www.scientificamerican.com/article.cfm?id=mapping-chromosome-21. Accessed Feb. 3, 2010.
Levy, et al. The Diploid Genome Sequence of an Individual Human PLoS Biol. Sep. 4, 2007;5(10):e254.
Li, et al. Size separation of circulatory DNA in maternal plasma permits ready detection of fetal DNA polymorphisms. Clin Chem. Jun. 2004;50(6):1002-11.
Liao, et al. Targeted massively parallel sequencing of maternal plasma. DNA permits efficient and unbiased detection of fetal alleles. Clin Chem. Jan. 2011;57(1):92-101.
Lieberfarb, et al. Genome-wide loss of heterozygosity analysis from laser capture microdissected prostate cancer using single nucleotide polymorphic allele (SNP) arrays and a novel bioinformatics platform dChipSNP. Cancer Res. Aug. 15, 2003;63(16):4781-5.
Life Technologies Corporation. Life Technologies Launches Ion PGM Sequencer. Carlsbad, Calif. Dec. 14, 2010. 2pages.
Liu, et al. Feasibility study of using fetal DNA in maternal plasma for non-invasive prenatal diagnosis. Acta Obstet Gynecol Scand. 2007;86(5):535-41.
Lizardi, et al. Mutation detection and single-molecule counting using isothermal rolling-circle amplification. Nat Genet. Jul. 1998;19(3):225-32.
Lo, et al. Digital PCR for the molecular detection of fetal chromosomal aneuploidy. Proc Natl Acad Sci U S A. Aug. 7, 2007;104(32):13116-21.
Lo, et al. Increased fetal DNA concentrations in the plasma of pregnant women carrying fetuses with trisomy 21. Clin Chem. Oct. 1999;45(10):1747-51.
Lo, et al. Maternal plasma. DNA sequencing reveals the genome-wide genetic and mutational profile of the fetus. Sci Transl Med. Dec. 8, 2010;2(61):61ra91.
Lo, et al. Non-invasive prenatal diagnosis of fetal chromosomal aneuploidies by maternal plasma nucleic acid analysis. Clinical Chemistry. 2008; 54 (3):461-466.
Lo, et al. Prenatal diagnosis of fetal RhD status by molecular analysis of maternal plasma. N Engl J Med. Dec. 10, 1998;339(24):1734-8.
Lo, et al. Presence of fetal DNA in maternal plasma .Lancet. Aug. 16, 1997;350(9076):485-7.
Lo, et al. Quantitative analysis of fetal DNA in maternal plasma and serum: implications for noninvasive prenatal diagnosis. Am J Hum Genet. Apr. 1998;62(4):768-75.
Lo, et al. Rapid clearance of fetal DNA from maternal plasma. Am J Hum Genet. Jan. 1999;64(1):218-24.
Lo, Y. M. Noninvasive prenatal detection of fetal chromosomal aneuploidies by maternal plasma nucleic acid analysis: a review of the current state of the art. BJOG, 2009, vol. 116, 152-157.
Lun, et al. Microfluidics Digital PCR Reveals a Higher than Expected Fraction of Fetal DNA in Maternal Plasma. Clinical Chemistry, 2008, vol. 54, No. 10, 1664-1672.
Maloney et al. "Microchimerism of maternal origin persists into adult life," J. Clin. Invest. 104:41-47 (1999).
Mardis, E. Next-generation DNA sequencing methods. Annu Rev Genomics Hum Genet. 2008;9:387-402. doi: 10.1146/annurev.genom.9.081307.164359.
Margulies, et al. Genome sequencing in microfabricated high-density picolitre reactors. Nature. Sep. 15, 2005;437(7057):376-80. Epub Jul. 31, 2005.
Marks, et al. Epidermal growth factor receptor (EGFR) expression in prostatic adenocarcinoma after hormonal therapy: a fluorescence in situ hybridization and immunohistochemical analysis. The Prostate. 2008; 68:919-923.
McCarley, et al. Patterning of surface-capture architectures in polymer-based microanalytical devices. In Kutter, et al. Eds. Royal Society of Chemistry Special Publication. 2005;130-132. (Abstract only).
McKernan, et al. Sequence and structural variation in a human genome uncovered by short-read, massively parallel ligation sequencing using two-base encoding. Genome Res. Sep. 2009;19(9):1527-41.
McPherson et al. An introduction to PCR. in PCR, second edition. 2006; 1-8.
Meng, et al.: "Design and Synthesis of a Photocleavable Fluorescent Nucleotide 3'-O-Allyl-dGTPPC-Bodipy-FL-510 as a Reversible Terminator for DNA Sequencing by Synthesis", J. Org. Chem. 2006, 71, pp. 3248-3252, XP-002652986.
Metzker. Sequencing technologies—the next generation. Nat Rev Genet. Jan. 2010;11(1):31-46.
Micale, et al. Double trisomy revisited—a multicenter experience. Prenat Diagn. Feb. 2010;30(2):173-6. doi: 10.1002/pd.2429.
Moore, et al. Prenatal diagnosis of aneuploidy and deletion 22q11.2 in fetuses with ultrasound detection of cardiac defects. Am J Obstet Gynecol. Dec. 2004;191(6):2068-73.

(56) References Cited

OTHER PUBLICATIONS

Mullis, et al. Specific enzymatic amplification of DNA in vitro: the polymerase chain reaction. Cold Spring Harb Symp Quant Biol. 1986;51 Pt 1:263-73.
Mullis, et al. Specific Synthesis of DNA in Vitro via a Polymerase-Catalyzed Chain Reaction. Methods in Enzymology, vol. 155, Recmbinant DNA, part F, 1987, 18 pages.
Mullis, K.B. et al., "Specific Synthesis of DNA in Vitro via a Polymerase-Catalyzed Chain Reaction", Methods in Enzymology, Vol. 155, Recmbinant DNA, part F, 1987, 19 pages.
Nakamoto, et al. Detection of microsatellite alterations in plasma DNA of malignant mucosal melanoma using whole genome amplification. Bull Tokyo Dent Coll. May 2008;49(2):77-87.
Nannya, et al. A robust algorithm for copy number detection using high-density oligonucleotide single nucleotide polymorphism genotyping arrays. Cancer Res. Jul. 15, 2005;65(14):6071-9.
Nassbaum et al. Principles of Clinical Cytogenetics. In Genetics in Medicine, seventh edition, chapter 5. 2007; 59-83.
Natera. Natera launches non-invasive prenatal test panorama with best-in-class sensitivity, specificity for detection of fetal chromosomal abnormalities. San Carlos, Calif. Feb. 20, 2013. 3pages.
Nelson, et al. Genotyping Fetal DNA by Non-Invasive Means: Extraction From Maternal Plasma. Vox Sang. 2001;80:112-116.
Nicklas, et al. A real-time multiplex SNP melting assay to discriminate individuals. J Forensic Sci. Nov. 2008;53(6):1316-24.
No. C 11-06391 SI—Preliminary Injunction Order. *Aria Diagnostics, Inc.* v *Sequenom, Inc.* Filed Jul. 3, 2013.
Notice of Allowance and Issue Fee Due Dec. 9, 2010 issued in U.S. Appl. No. 11/701,686.
Notice of allowance dated Jan. 26, 2015 for U.S. Appl. No. 13/835,926.
Notice of allowance dated Mar. 1, 2012 for U.S. Appl. No. 12/696,509.
Notice of allowance dated Jun. 21, 2012 for U.S. Appl. No. 12/815,647.
Notice of allowance dated Jul. 12, 2012 for U.S. Appl. No. 13/452,083.
Notice of allowance dated Jul. 15, 2016 for U.S. Appl. No. 14/677,854.
Notice of allowance dated Sep. 4, 2013 for U.S. Appl. No. 13/102,717.
Notice of allowance dated Sep. 28, 2012 for U.S. Appl. No. 13/368,035.
Notice of allowance dated Oct. 5, 2012 for U.S. Appl. No. 11/763,421.
Notice of allowance dated Dec. 23, 2011 for U.S. Appl. No. 12/230,628.
Notice of allowance dated Dec. 29, 2011 for U.S. Appl. No. 11/763,245.
Notice of allowance dated Jul. 12, 2011 with allowed claims for U.S. Appl. No. 12/393,803.
Notice of Deposition of Cynthia Casson Morton. *Ariosa Diagnostics* v. *Verinata Health*. Case IPR2013-00276. U.S. Pat. No. 8,318,430. Nov. 25, 2013. 3pages.
Notice of Deposition of Cynthia Casson Morton. *Ariosa Diagnostics* v. *Verinata Health*. Case IPR2013-00277. U.S. Pat. No. 8,318,430. Nov. 25, 2013. 3pages.
Notice of Deposition of Robert Nussbaum. *Ariosa Diagnostics* v. *Verinata Health*. Case IPR2013-00276. U.S. Pat. No. 8,318,430. Nov. 25, 2013. 3pages.
Notice of Deposition of Robert Nussbaum. *Ariosa Diagnostics* v. *Verinata Health*. Case IPR2013-00277. U.S. Pat. No. 8,318,430. Nov. 25, 2013. 3pages.
Notice of filing date accorded to petition and time for filing patent owner preliminary response. *Ariosa Diagnostics* v. *Verinata Health*. Case IPR2013-00276. U.S. Pat. No. 8,318,430. May 15, 2013. 3pages.
Notice of filing date accorded to petition and time for filing patent owner preliminary response. *Ariosa Diagnostics* v. *Verinata Health*. IPR2013-00277. U.S. Pat. No. 8,318,430. May 15, 2013. 3pages.
Notice of reexamination request filing date from Reexam. No. 90/013,678 dated Jan. 15, 2016.
Office action (Ex parte Quayle) dated May 13, 2011 for U.S. Appl. No. 11/763,421.
Office Action dated Jan. 12, 2009 for U.S. Appl. No. 11/763,133.
Office Action dated Jan. 27, 2010 for U.S. Appl. No. 11/701,686.
Office action dated Jan. 28, 2009 for U.S. Appl. No. 11/701,686.
Office action dated Jan. 28, 2014 for U.S. Appl. No. 13/835,926.
Office action dated Feb. 5, 2014 for U.S. Appl. No. 12/689,517.
Office action dated Feb. 15, 2011 for U.S. Appl. No. 11/763,426.
Office action dated Feb. 19, 2015 for EP Application No. 12183946.8.
Office action dated Feb. 20, 2013 for EP Application No. 12183946.8.
Office action dated Feb. 23, 2015 for U.S. Appl. No. 12/689,517.
Office action dated Mar. 6, 2012 for U.S. Appl. No. 13/102,717.
Office action dated Mar. 7, 2012 for U.S. Appl. No. 12/816,043.
Office action dated Mar. 7, 2013 for European Application No. 11182181.
Office action dated Mar. 11, 2010 for U.S. Appl. No. 11/763,245.
Office action dated Mar. 11, 2015 for U.S. Appl. No. 13/737,730.
Office action dated Mar. 13, 2012 for U.S. Appl. No. 13/368,035.
Office action dated Mar. 20, 2013 for U.S. Appl. No. 12/815,674.
Office action dated Mar. 20, 2014 for U.S. Appl. No. 12/816,043.
Office action dated Mar. 21, 2014 for U.S. Appl. No. 12/815,674.
Office action dated Mar. 29, 2011 for U.S. Appl. No. 11/763,245.
Office action dated Apr. 4, 2012 for EP Application No. 07784444.7.
Office action dated Apr. 4, 2013 for U.S. Appl. No. 12/689,517.
Office action dated Apr. 5, 2012 for U.S. Appl. No. 12/751,931.
Office action dated Apr. 6, 2015 for U.S. Appl. No. 13/921,881.
Office action dated Apr. 6, 2015 for U.S. Appl. No. 14/168,714.
Office action dated Apr. 7, 2015 for U.S. Appl. No. 13/829,971.
Office action dated Apr. 9, 2013 for U.S. Appl. No. 13/306,520.
Office action dated Apr. 12, 2012 for U.S. Appl. No. 12/815,647.
Office action dated Apr. 23, 2015 for U.S. Appl. No. 12/751,940.
Office action dated Apr. 24, 2012 for EP Application No. 07784442.1.
Office action dated Apr. 25, 2011 for U.S. Appl. No. 12/393,803 with pending claims.
Office action dated Apr. 28, 2014 for U.S. Appl. No. 12/689,548.
Office action dated Apr. 29, 2015 for U.S. Appl. No. 13/794,503.
Office action dated May 6, 2011 for U.S. Appl. No. 11/763,133.
Office action dated May 7, 2014 for EP Application No. 12183946.8.
Office action dated May 8, 2014 for EP Application No. 09815105.3.
Office action dated May 8, 2015 for U.S. Appl. No. 12/816,043.
Office action dated May 10, 2012 for U.S. Appl. No. 12/560,708.
Office action dated May 11, 2015 for U.S. Appl. No. 13/863,992.
Office action dated May 12, 2011 for U.S. Appl. No. 12/230,628.
Office action dated May 12, 2014 for U.S. Appl. No. 13/012,222.
Office action dated May 18, 2011 for U.S. Appl. No. 12/413,467.
Office action dated May 26, 2011 for U.S. Appl. No. 11/762,750.
Office action dated May 31, 2013 for U.S. Appl. No. 13/835,926.
Office action dated Jun. 3, 2013 for U.S. Appl. No. 13/306,640.
Office action dated Jun. 3, 2013 for U.S. Appl. No. 13/837,974.
Office action dated Jun. 4, 2012 for U.S. Appl. No. 11/762,747.
Office action dated Jun. 5, 2012 for U.S. Appl. No. 12/393,833.
Office action dated Jun. 5, 2013 for U.S. Appl. No. 12/751,940.
Office action dated Jun. 8, 2015 for U.S. Appl. No. 14/677,854.
Office action dated Jun. 10, 2015 for U.S. Appl. No. 13/830,871.
Office action dated Jun. 14, 2010 for U.S. Appl. No. 11/763,426.
Office action dated Jun. 18, 2012 for U.S. Appl. No. 12/751,908.
Office action dated Jun. 18, 2012 for U.S. Appl. No. 12/751,940.
Office action dated Jul. 2, 2010 for EP Application No. 07784442.1.
Office action dated Jul. 7, 2011 for U.S. Appl. No. 12/696,509.
Office action dated Jul. 9, 2012 for U.S. Appl. No. 11/762,750.
Office action dated Jul. 10, 2009 for U.S. Appl. No. 11/763,421.
Office action dated Jul. 10, 2012 for U.S. Appl. No. 13/433,232.
Office action dated Jul. 16, 2015 for U.S. Appl. No. 13/837,974.
Office action dated Jul. 17, 2012 for U.S. Appl. No. 13/102,717.
Office action dated Jul. 17, 2014 for U.S. Appl. No. 13/921,881.
Office action dated Jul. 21, 2015 for U.S. Appl. No. 12/689,548.
Office action dated Jul. 26, 2011 for U.S. Appl. No. 11/763,245.
Office action dated Jul. 29, 2014 for U.S. Appl. No. 13/835,926.
Office action dated Jul. 30, 2012 for U.S. Appl. No. 13/368,035.
Office action dated Aug. 1, 2012 for U.S. Appl. No. 12/815,674.
Office action dated Aug. 1, 2014 for U.S. Appl. No. 12/816,043.

(56) References Cited

OTHER PUBLICATIONS

Office action dated Aug. 2, 2010 for EP Application No. 07784444.7.
Office action dated Aug. 7, 2013 for U.S. Appl. No. 13/863,992.
Office action dated Aug. 18, 2015 for U.S. Appl. No. 14/581,225.
Office action dated Aug. 19, 2015 for U.S. Appl. No. 12/689,517.
Office action dated Aug. 27, 2010 for U.S. Appl. No. 11/762,747.
Office action dated Aug. 29, 2014 for U.S. Appl. No. 13/837,974.
Office Action dated Sep. 8, 2010 for U.S. Appl. No. 11/701,686.
Office action dated Sep. 10, 2010 for U.S. Appl. No. 11/762,750.
Office Action dated Sep. 11, 2009 for U.S. Appl. No. 11/701,686.
Office action dated Sep. 14, 2012 for U.S. Appl. No. 12/393,833.
Office action dated Sep. 17, 2014 for U.S. Appl. No. 13/863,992.
Office action dated Sep. 18, 2015 for U.S. Appl. No. 12/816,043.
Office action dated Sep. 22, 2011 for U.S. Appl. No. 12/815,647.
Office action dated Sep. 23, 2009 for EP Application No. EP07763674.4.
Office action dated Sep. 27, 2010 for U.S. Appl. No. 12/413,485.
Office action dated Sep. 27, 2013 for U.S. Appl. No. 12/816,043.
Office action dated Oct. 3, 2014 for U.S. Appl. No. 13/792,661.
Office action dated Oct. 24, 2011 for U.S. Appl. No. 11/762,747.
Office action dated Oct. 25, 2012 for U.S. Appl. No. 12/816,043.
Office action dated Oct. 29, 2010 for U.S. Appl. No. 12/230,628.
Office action dated Nov. 3, 2009 for U.S. Appl. No. 11/763,133.
Office action dated Nov. 24, 2014 for U.S. Appl. No. 12/689,548.
Office action dated Dec. 1, 2009 for U.S. Appl. No. 11/763,426.
Office action dated Dec. 2, 2008 for U.S. Appl. No. 11/762,747.
Office action dated Dec. 3, 2008 for U.S. Appl. No. 11/763,426.
Office action dated Dec. 5, 2014 for U.S. Appl. No. 14/168,714.
Office action dated Dec. 10, 2014 for U.S. Appl. No. 12/751,940.
Office action dated Dec. 12, 2013 for EP Application No. 12183946.8.
Office action dated Dec. 12, 2014 for U.S. Appl. No. 13/738,268.
Office action dated Dec. 13, 2013 for U.S. Appl. No. 13/306,698.
Office action dated Dec. 15, 2015 for U.S. Appl. No. 14/677,854.
Office action dated Dec. 19, 2012 for U.S. Appl. No. 13/218,317.
Office action dated Dec. 31, 2009 for U.S. Appl. No. 11/763,421.
Office action dated Dec. 31, 2011 for U.S. Appl. No. 11/763,421.
Oosterwijk, et al. Prenatal diagnosis of trisomy 13 on fetal cells obtained from maternal blood after minor enrichment. Prenat Diagn. 1998;18(10):1082-5.
Oral hearing transcript. *Ariosa Diagnostics* v. *Verinata Health*. Case IPR2013-00276 and IPR2013-00277. U.S. Pat. No. 8,318,430. U.S. Appl. No. 13/368,035. Technology Center 1600. Held on Jul. 16, 2014. 79pages.
Order: Conduct of the Proceeding. *Ariosa Diagnostics* v. *Verinata Health*. Case IPR2013-00276 and IPR2013-00277. U.S. Pat. No. 8,318,430 B2. Nov. 19, 2013. 4pages.
Order: Conduct of the Proceedings. *Ariosa Diagnostics* v. *Verinata Health*. Case IPR2013-00276 and IPR2013-00277(LMG). U.S. Pat. No. 8,318,430. Jun. 19, 2013. 4pages.
Order: Conduct of the Proceedings. *Ariosa Diagnostics* v. *Verinata Health*. Case IPR2013-00276 and IPR2013-00277. U.S. Pat. No. 8,318,430. Mar. 31, 2014. 3pages.
Order: Conduct of the Proceedings. *Ariosa Diagnostics* v. *Verinata Health*. Case IPR2013-00276 and IPR2013-00277. U.S. Pat. No. 8,318,430. Apr. 22, 2014. 4pages.
Order: Trial Hearing. *Ariosa Diagnostics* v. *Verinata Health*. Case IPR2013-00276 and IPR2013-00277. U.S. Pat. No. 8,318,430. May 21, 2014. 3pages.
Paez, et al. Genome coverage and sequence fidelity of phi29 polymerase-based multiple strand displacement whole genome amplification. Nucleic Acids Res. May 18, 2004;32(9):e71.
Pakstis, et al. Candidate SNPs for a universal individual identification panel. Hum Genet. May 2007;121(3-4):305-17.
Pakstis, et al. SNPs for a universal individual identification panel. Hum Genet. Mar. 2010; 127(3):315-24.
Patent owner reply to petitioner's opposition to patent owner's motion to exclude. *Ariosa Diagnostics* v. *Verinata Health* U.S. Pat. No. 8,318,430. Jun. 3, 2014. 8pages. Case IPR2013-00276.
Patent owner reply to petitioner's opposition to patent owner's motion to exclude. *Ariosa Diagnostics* v. *Verinata Health* U.S. Pat. No. 8,318,430. Jun. 3, 2014. 8pages. Case IPR2013-00277.
Patent owner submission of mandatory notice information. *Ariosa Diagnostics* v. *Verinata Health*. Case IPR2013-00276. U.S. Pat. No. 8,318,430. May 31, 2013. 4pages.
Patent owner submission of mandatory notice information. *Ariosa Diagnostics* v. *Verinata Health*. Case IPR2013-00277. U.S. Pat. No. 8,318,430. May 31, 2013. 4pages.
Patent owner Verinata Health List of Proposed Motions. *Ariosa Diagnostics* v. *Verinata Health*. Case IPR2013-00277. U.S. Pat. No. 8,318,430. Nov. 12, 2013. 3pages.
Patent owner Verinata Health list of proposed motions. *Ariosa Diagnostics* v. *Verinata Health*. IPR2013-00276. U.S. Pat. No. 8,318,430. Nov. 12, 2013. 3pages.
Patent owner Verinata Health motion to exclude evidence. *Ariosa Diagnostics* v. *Verinata Health*. Case IPR2013-00277. U.S. Pat. No. 8,318,430. May 13, 2014. 16pages.
Patent owner Verinata Health motion to exclude evidence. *Ariosa Diagnostics* v. *Verinata Health*. IPR2013-00276. U.S. Pat. No. 8,318,430. May 13, 2014. 16pages.
Patent owner Verinata Health Notice of objection to evidence. *Ariosa Diagnostics* v. *Verinata Health*. IPR 2013-00276. U.S. Pat. No. 8,318,430. Apr. 7, 2014. 4pages.
Patent owner Verinata Health Notice of objection to evidence. *Ariosa Diagnostics* v. *Verinata Health*. IPR 2013-00277. U.S. Pat. No. 8,318,430. Apr. 7, 2014. 4pages.
Patent owner Verinata Health Notice of objection to evidence. *Ariosa Diagnostics* v. *Verinata Health*. IPR2013-00276. U.S. Pat. No. 8,318,430. Apr. 10, 2014. 8pages.
Patent owner Verinata Health Notice of objection to evidence. *Ariosa Diagnostics* v. *Verinata Health*. IPR2013-00277. U.S. Pat. No. 8,318,430. Apr. 10, 2014. 8pages.
Patent owner Verinata Health Oral Argument. *Ariosa Diagnostics* v. *Verinata Health*. Cases IPR 2013-00276 and IPR 2013-00277. Jul. 16, 2014. 37pages.
Patent owner Verinata Health Power of Attorney. *Ariosa Diagnostics* v. *Verinata Health*. IPR2013-00276. U.S. Pat. No. 8,318,430. May 31, 2013. 3pages.
Patent owner Verinata Health Power of Attorney. *Ariosa Diagnostics* v. *Verinata Health*. IPR2013-00277. U.S. Pat. No. 8,318,430. May 31, 2013. 3pages.
Patent owner Verinata Health request for oral argument. *Ariosa Diagnostics* v. *Verinata Health*. Case IPR2013-00276. U.S. Pat. No. 8,318,430. May 13, 2014. 3pages.
Patent owner Verinata Health request for oral argument. *Ariosa Diagnostics* v. *Verinata Health*. Case IPR2013-00277. U.S. Pat. No. 8,318,430. May 13, 2014. 3pages.
Patent owner Verinata Health revised mandatory notices. *Ariosa Diagnostics* v. *Verinata Health*. Case IPR2013-00276. U.S. Pat. No. 8,318,430. Jul. 11, 2014. 4pages.
Patent owner Verinata Health revised mandatory notices. *Ariosa Diagnostics* v. *Verinata Health*. Case IPR2013-00277. U.S. Pat. No. 8,318,430. Jul. 11, 2014. 4pages.
Patent owner Verinata Health submission of Demonstrative exhibits for oral argument. *Ariosa Diagnostics* v. *Verinata Health*. Case IPR2013-00276. U.S. Pat. No. 8,318,430. Jul. 11, 2014. 3pages.
Patent owner Verinata Health submission of Demonstrative exhibits for oral argument. *Ariosa Diagnostics* v. *Verinata Health*. Case IPR2013-00277. U.S. Pat. No. 8,318,430. Jul. 11, 2014. 3pages.
Patent owner Verinata Health Supplemental notice of objection to evidence. *Ariosa Diagnostics* v. *Verinata Health*. IPR2013-00276. U.S. Pat. No. 8,318,430. Apr. 10, 2014. 8pages.
Patent owner Verinata Health Supplemental notice of objection to evidence. *Ariosa Diagnostics* v. *Verinata Health*. IPR2013-00277. U.S. Pat. No. 8,318,430. Apr. 10, 2014. 8pages.
Patent owner Verinata Health updated exhibit list. *Ariosa Diagnostics* v. *Verinata Health*. Case IPR2013-00276. U.S. Pat. No. 8,318,430. May 13, 2014. 4pages.
Patent owner Verinata Health updated exhibit list. *Ariosa Diagnostics* v. *Verinata Health*. Case IPR2013-00277. U.S. Pat. No. 8,318,430. May 13, 2014. 4pages.

(56) References Cited

OTHER PUBLICATIONS

Patent owner Verinata Health's updated exhibit list. *Ariosa Diagnostics* v. *Verinata Health*. Case IPR2013-00276. U.S. Pat. No. 8,318,430. Jul. 11, 2014. 4pages.
Patent owner Verinata Health's updated exhibit list. *Ariosa Diagnostics* v. *Verinata Health*. Case IPR2013-00277. U.S. Pat. No. 8,318,430. Jul. 11, 2014. 4pages.
Patent owner's reply to petitioner's opposition to patent owner's motion to exclude. *Ariosa Diagnostics* v. *Verinata Health*. Case IPR2013-00276. U.S. Pat. No. 8,318,430. Jun. 3, 2014. 8pages.
Patent owner's reply to petitioner's opposition to patent owner's motion to exclude. *Ariosa Diagnostics* v. *Verinata Health*. Case IPR2013-00277. U.S. Pat. No. 8,318,430. Jun. 3, 2014. 8pages.
Pathak, et al. Circulating cell-free DNA in plasma/serum of lung cancer patients as a potential screening and prognostic tool. Clin Chem. Oct. 2006;52(10):1833-42.
Pertl, et al. Detection of male and female DNA in maternal plasma by multiplex fluorescent polymerase chain reaction amplification of short tandem repeats. Hum Genet. Jan. 2000;106(1):45-9.
Petitioner Ariosa's Updated Mandatory Notices. *Ariosa Diagnostics* v. *Verinata Health*. Case IPR2013-00276. U.S. Pat. No. 8,318,430. Jun. 11, 2013. 3pages.
Petitioner Ariosa's Updated Mandatory Notices. *Ariosa Diagnostics* v. *Verinata Health*. Case IPR2013-00277. U.S. Pat. No. 8,318,430. Jun. 11, 2013. 3pages.
Petitioner Ariosa's updated Power of Attorney. *Ariosa Diagnostics* v. *Verinata Health*. Case IPR2013-00276. U.S. Pat. No. 8,318,430. Jun. 11, 2013. 3pages.
Petitioner Ariosa's updated Power of Attorney. *Ariosa Diagnostics* v. *Verinata Health*. Case IPR2013-00277. U.S. Pat. No. 8,318,430. Jun. 11, 2013. 3pages.
Petitioner reply in support of the petition. *Ariosa Diagnostics* v. *Verinata Health*. Case IPR2013-00277. U.S. Pat. No. 8,318,430. Apr. 3, 2014. 18pages.
Petitioner's opposition to patent owner's motion to exclude. *Ariosa Diagnostics* v. *Verinata Health*. Case IPR2013-00276. U.S. Pat. No. 8,318,430. May 27, 2014. 14pages.
Petitioner's opposition to patent owner's motion to exclude. *Ariosa Diagnostics* v. *Verinata Health*. Case IPR2013-00277. U.S. Pat. No. 8,318,430. May 27, 2014. 14pages.
Petitioner's reply in support of the petition. *Ariosa Diagnostics* v. *Verinata Health*. IPR2013-00276. U.S. Pat. No. 8,318,430. Apr. 3, 2014. 18pages.
Petitioner's request for oral argument. *Ariosa Diagnostics* v. *Verinata Health*. Case IPR2003-00276. U.S. Pat. No. 8,318,430. May 13, 2014. 3pages.
Petitioner's request for oral argument. *Ariosa Diagnostics* v. *Verinata Health*. Case IPR2013-00277. U.S. Pat. No. 8,318,430. May 13, 2014. 3pages.
Pfaffl, et al. Relative expression software tool (REST) for groupwise comparison and statistical analysis of relative expression results in real-time PCR. Nucleic Acids Res. May 1, 2002;30(9):e36.
Pheiffer, et al. Polymer-stimulated liagtion: enhanced blunt- or cohesive-end liagtion of DNA or deoxyribooligonucleotides by T4 DNA ligase in polymer solutions. Nucleic Acids Res. Nov. 25, 1983;11(22):7853-71.
Pohl et al. Principle and applications of digital PCR. Expert Rev Mol Diagn. Jan. 2004;4(1):41-7.
Power of Attorney *Ariosa Diagnostics* v. *ISIS Innovation Limited*. IPR2013-00276. U.S. Pat. No. 8,318,430. May 7, 2013. 2pages.
Power of Attorney *Ariosa Diagnostics* v. *ISIS Innovation Limited*. IPR2013-00277. U.S. Pat. No. 8,318,430. May 7, 2013. 2pages.
PowerPoint Slides: Ariosa Diagnostics Petitioner. Case IPR2013-00276. Jul. 14, 2014. 23pages.
PowerPoint Slides: Ariosa Diagnostics Petitioner. Case IPR2013-00277. Jul. 14, 2014. 23pages.
Prosecution history of U.S. Pat. No. 8,318,430 (U.S. Appl. No. 13/368,035), issued Nov. 27, 2012.
Pushkarev, et al. Single-molecule sequencing of an individual human genome. Nat Biotechnol. Sep. 2009;27(9):847-50.
Quail, et al. A large genome center's improvements to the Illumina sequencing system. Nat Mathods. Dec. 2008;5(12):1005-10.
Quake, S. Sizing up cell-free DNA. Clin Chem. Mar. 2012;58(3):489-90. doi: 10.1373/clinchem.2011.174250. Epub Jan. 10, 2012.
Receipt of Orig. Ex Parte Request by Third Party from Reexam. No. 90/013,678 dated Jan. 8, 2016.
REPLI-g® Mini and Midi Kits pamphlet from Qiagen (Oct. 2005).
Rosato, M. Verinata Health, Inc.'s Preliminary Patent Owner Response Pursuant to 37 C.F.R. §42.107(a). Dated Jul. 29, 2013. For Case IPR2013-00276. U.S. Pat. No. 8,318,430.
Rosato, Verinata Health Inc.'s Preliminary Patent Owner Response Pursuant to 37 C.F.R. §42.107(a). Dated Jul. 29, 2013. For Case IPR2013-00277. U.S. Pat. No. 8,318,430.
Rossa, et al. Blunted increase of digital skin vasomotion following acetylcholine and sodium nitroprusside iontophoresis in systemic sclerosis patients. Rheumatology (Oxford). Jul. 2008;47(7):1012-7. doi: 10.1093/rheumatology/ken117. Epub Apr. 22, 2008.
Sambrook, et al., (2001) Molecular Cloning, Third Edition, Cold Spring Harbor Laboratory Press.
Saunders. Dorland'S Illustrated Medical Dictionary, 30th Edition. The Curtis Center, Independent Square West, Philadelphia, PA 19106. 2003; 764.
Scheduling order. *Ariosa Diagnostics* v. *Verinata Health*. Case IPR2013-00277. U.S. Pat. No. 8,318,430. Oct. 25, 2013. 6pages.
Scheduling order. *Ariosa Diagnostics* v. *Verinata Health*. IPR2013-00276. U.S. Pat. No. 8,318,430 B2. Oct. 25, 2013. 6pages.
Schwartzenbach, et al. Cell-free tumor DNA in blood plasma as a marker for circulating tumor cells in prostate cancer. Clin Cancer Res. Feb. 1, 2009;15(3):1032-8.
Schwartzenbach, et al. Comparative evaluation of cell-free tumor DNA in blood and disseminated tumor cells in bone marrow of patients with primary breast cancer. Breast Cancer Res. 2009;11(5):R71.
Second Amended Complaint for Patent Infringement dated Mar. 01, 2013 for Case No. 3:12-cv-05501-SI.
Second declaration of Cynthia Casson Morton, in re patent of: Chuu. Methods of Fetal Abnormality Detection. IPR2013-00276. Apr. 3, 2014. 31pages.
Second declaration of Cynthia Casson Morton, in re patent of: Chuu. Methods of Fetal Abnormality Detection. IPR2013-00277. Apr. 3, 2014. 31pages.
Second petition for inter partes review. *Ariosa Diagnostics* v. *Verinata Health*. U.S. Pat. No. 8,318,430. May 10, 2013. 59pages.
Sequenom, Inc. Sequenom Center for molecular medicine announces launch of materniT21 noninvasive prenatal test for down syndrome. San Diego. Oct. 17, 2011. 2pages.
Shendure, et al. Accurate multiplex polony sequencing of an evolved bacterial genome. Science. Sep. 9, 2005;309(5741):1728-32. Epub Aug. 4, 2005.
Shendure, et al. Next-generation DNA sequencing. Nature. 2008; 26(10):1135-1145.
Siegel et al. New insights into the troubles of aneuploidy. Annu Rev Cell Dev Biol. 2012;28:189-214. doi: 10.1146/annurev-cellbio-101011-155807. Epub Jul. 9, 2012.
Solexa Genome Analysis System. 2006; 1-2.
Solexa, Biotechniques, 2007, Protocol Guide, 1 page.
Soni, et al. Progress toward ultrafast DNA sequencing using solid-state nanopores. Clin Chem. Nov. 2007;53(11):1996-2001. Epub Sep. 21, 2007.
Sparks et al. Noninvasive prenatal detection and selective analysis of cell-free DNA obtained from maternal blood: evaluation for trisomy 21 and trisomy 18. Am J Obstet Gynecol. Apr. 2012;206(4):319.e1-9. doi: 10.1016/j.ajog.2012.01.030. Epub Jan. 26, 2012.
Sparks, et al. Selective analysis of cell-free DNA in maternal blood for evaluation of fetal trisomy. Prenat Diagn. Jan. 2012;32(1):3-9. doi: 10.1002/pd.2922. Epub Jan. 6, 2012.
Srivatsan, et al. High-precision, whole-genome sequencing of laboratory strains facilitates genetic studies. PLoS Genet. Aug. 1, 2008;4(8):e1000139. doi: 10.1371/journal.pgen.1000139.
Su, et al. Human urine contains small, 150 to 250 nucleotide-sized, soluble DNA derived from the circulation and may be useful in the detection of colorectal cancer. J Mol Diagn. May 2004;6(2):101-7.

(56) References Cited

OTHER PUBLICATIONS

Submission of petitioner's demonstratives exhibits for oral arguments. *Ariosa Diagnostics* v. *Verinata Health*. Case IPR2013-00277. U.S. Pat. No. 8,318,430. Jul. 14, 2014. 3pages.
Submission of petitioner's demonstratives exhibits for oral arguments. *Ariosa Diagnostics* v. *Verinata Health*. IPR2013-00276. U.S. Pat. No. 8,318,430. Jul. 14, 2014.
Supplementary Material referred to on p. 8 of Craig et al., Identification of Genetic Variants using Barcoded Multiplexed Sequencing, Nat Methods, 5(10):887-93 (2008).
Swarup et al. Circulating (cell-free) nucleic acids—a promising, non-invasive tool for early detection of several human diseases. FEBS Lett. Mar. 6, 2007;581(5):795-9. Epub Feb. 2, 2007.
Tettelin, et al. The nucleotide sequence of *Saccharomyces cerevisiae* chromosome VII. Nature. May 29, 1997;387(6632 Suppl):81-4.
The Use of Coded PCR Primers Enables High-Throughput Sequencing of Multiple Homolog Amplification Products by 454 Parallel Sequencing, Jonas Binladen et al., PLoS One. 2007; 2(2): e197 ("Binladen").
Tong, et al. Noninvasive prenatal detection of trisomy 21 by an epigenetic-genetic chromosome-dosage approach. Clin Chem. Jan. 2010;56(1):90-8.
Tufan, et al., Analysis of Cell-Free Fetal DNA from Maternal Plasma and Serum Using a Conventional Multiplex PCR: Factors Influencing Success. 2005. Turk. J. Med. Sci. 35:85-92.
Uitto, et al. Probing the fetal genome: progress in non-invasive prenatal diagnosis. Trends Mol Med. Aug. 2003;9(8):339-43.
U.S. Appl. No. 61/296,358, filed Jan. 19, 2010.
U.S. Appl. No. 61/296,464, filed Jan. 19, 2010.
Vallone, et al. Demonstration of rapid multiplex PCR amplification involving 16 genetic loci. Forensic Sci Int Genet. Dec. 2008;3(1):42-5.
Verinata and Stanford's Opening Claim Construction Brief for U.S. Pat. No. 8,296,076 and U.S. Pat. No. 8,318,430 dated Jun. 5, 2013 for Case No. 3:12-cv-05501-SI.
Verinata and Stanford's Reply Claim Construction Brief for U.S. Pat. No. 8,296,076 and U.S. Pat. No. 8,318,430 dated Jul. 17, 2013 for Case No. 3:12-cv-05501-SI.
Verinata Health patent owner response. *Ariosa Diagnostics* v. *Verinata Health*. Case IPR2013-00277. U.S. Pat. No. 8,318,430. Jan. 16, 2014. 63pages.
Verinata Health patent owner response. *Ariosa Diagnostics* v. *Verinata Health*. IPR2013-00276. U.S. Pat. No. 8,318,430. Jan. 16, 2014. 65pages.
Verinata Health preliminary patent owner response. *Ariosa Diagnostics* v. *Verinata Health*. Case IPR2013-00277. U.S. Pat. No. 8,318,430. Jul. 29, 2013. 30pages.
Verinata Health preliminary patent owner response. *Ariosa Diagnostics* v. *Verinata Health*. IPR2013-00276. U.S. Pat. No. 8,318,430. Jul. 29, 2013. 30pages.
Verinata Health. Verinata Announces Peer-Reviewed Manuscript in Obstetrics & Gynecology (The Green Journal), the Official Publication of the American College of Obstetricians and Gynecologists. Redwood City, Calif Feb. 23, 2012. 2pages.
Videotaped deposition of Atul J Butte. *Ariosa Diagnostics* v. *Verinata Health*. Mar. 14, 2014. 171pages.
Voelkerding, et al. Digital Fetal Aneuploidy Diagnosis by Next-Generation Sequencing. Clin Chem. Mar. 2010;56(3):336-8.
Voelkerding, et al. Next-generation sequencing: from basic research to diagnostics Clin Chem. Apr. 2009;55(4):641-58.
Vogelstein, et al. "Digital PCR." Proc Natl. Acad Sci. USA, Aug. 1999, vol. 96., 9236-9241.
Voldborg, et al. Epidermal growth factor receptor (EGFR) and EGFR mutations, function and possible role in clinical trials. Ann Oncol. Dec. 1997;8(12):1197-206.
Von Eggeling, et al. Determination of the origin of single nucleated cells in maternal circulation by means of random PCR and a set of length polymorphisms. Hum Genet. Feb. 1997;99(2):266-70.

Walker, et al. Strand displacement amplification—an isothermal, in vitro DNA amplification technique. Nucleic Acids Res. Apr. 11, 1992;20(7):1691-6.
Wheeler, et al. The complete genome of an individual by massively parallel DNA sequencing. Nature. Apr. 17, 2008;452(7189):872-6.
Wright, et al. The use of cell-free fetal nucleic acids in maternal blood for noninvasive prenatal diagnosis. Hum Reprod Update. Jan.-Feb. 2009;15(1):139-51.
Yang, et al. Rapid Prenatal Diagnosis of Trisomy 21 by Real-time Quantitative Polymerase Chain Reaction with Amplification of Small Tandem Repeats and S100B in Chromosome 21. Yonsei Medical Journal, 2005, vol. 46, No. 2, 193-197.
Yu, et al. Objective Aneuploidy Detection for Fetal and Neonatal Screening Using Comparative Genomic Hybridization (CGH). Cytometry. 1997; 28(3): 191-197. (Abstract).
Zavala, et al. Genomic GC content prediction in prokaryotes from a sample of genes. Gene. Sep. 12, 2005;357(2):137-43.
Zhang, et al. A novel method to calculate the G+C content of genomic DNA sequences. J Biomol Struct Dyn. Oct. 2001;19(2):333-41.
Zhang, et al. Whole genome amplification from a single cell: implications for genetic analysis. Proc Natl Acad Sci U S A. Jul. 1, 1992;89(13):5847-51.
Zhao, et al. An integrated view of copy number and allelic alterations in the cancer genome using single nucleotide polymorphism arrays. Cancer Res. May 1, 2004;64(9):3060-71.
Zimmerman et al. Qiagen News. 2003. e12. Available via uri: <b2b.qiagen.com/literature/qiagennews/weeklyarticle/apr03/e12/default.aspx>.
Zimmerman, et al. Macromolecular crowding allows blunt-end ligation by DNA ligase from rat liver or *Escheridia coli*. Proc Natl Acad Sci U S A. Oct. 1983;80(19):5852-6.
Zimmerman, et al. Novel real-time quantitative PCR test for trisomy 21. Jan. 1, 2002. Clinical Chemistry, American Association for Clinical Chemistry. 48:(2) 362-363.
Andersson et al., "Comparative analysis of human gut micro biota by barcoded pyrosequencing," PLoS ONE, vol. 3:e2836 (2008).
Brisco et al., Outcome prediction in childhood acute lymphoblastic leukaemia by molecular quantification of residual disease at the end of induction, Lancet, vol. 343:196-200 (1994).
Declaration of Sylvia Hall-Ellis. In re U.S. Pat. No. 9,493,831, dated Jun. 28, 2018, 133 pages.
Dethlefsen et al., The pervasive effects of an antibiotic on the human gut microbiota, as revealed by deep 16s rRNA sequencing, PLoS Biology, vol. 6:e280 (2008).
Droege & Hill, The Genome Sequencer FLXTM System-Longer reads, more applications, straight forward bioinformatics and more complete data sets, Journal of Biotechnology, vol. 136:3-10 (2008).
Ex. 1002, "Declaration of Michael L. Metzker, Ph.D.," Case No. IPR2018-01317, U.S. Pat. No. 9,493,831, dated Jun. 29, 2018, 118 pages.
Ex. 1014, "Multiplexed Sequencing with the Illumina Genome Analyzer System", Illumina, dated Dec. 2, 2008, 4 pages.
Ferre et al., Quantitative or semi-quantitative PCR: Reality versus myth, Genome Research, vol. 2:1-9 (1992).
Fierer et al., The influence of sex, handedness, and washing on the diversity of hand surface bacteria, Proc. Natl. Acad. Sci. USA, vol. 105:17994-17999 (2008).
Gibbs et al., Detection of single DNA base differences by competitive oligonucleotide priming, Nucleic Acids Research, vol. 17:2437-2448 (Apr. 11, 1989).
Gibbs et al., Multiplex DNA deletion detection and exon sequencing of the hypoxanthine phosphoribosyltransferase gene in Lesch-Nyhan families, Genomics, vol. 7:235-244 (1990).
Grompe et al., The rapid detection of unknown mutations in nucleic acids, Nature Genetics, vol. 5:111-117 (1993).
Hamady & Knight, Microbial community profiling for human microbiome projects: Tools, techniques, and challenges, Genome Research, vol. 19:1141-1152 (2009).
Hamady et al., Error-correcting barcoded primers for pyrosequencing hundreds of samples in multiplex, Nature Methods, vol. 5:235-237 (2008).

(56) References Cited

OTHER PUBLICATIONS

Harismendy, et al., Evaluation of next generation sequencing platforms for population targeted sequencing studies, Genome Biology, vol. 10:R32, dated Mar. 27, 2009, 13 pages.
Heid et al., Real time quantitative PCR, Genome Research, vol. 6:986-994 (1996).
Holland et al., Detection of specific polymerase chain reaction product by utilizing the 5 '—3' exonuclease activity of Thermus aquaticus DNA polymerase, Proc. Natl. Acad.Sci. USA, vol. 88:7276-7280 (1991).
Huber et al., Microbial population structures in the deep marine biosphere, Science, vol. 318:97-100 (2007).
*Illumina, Inc.* v. *Natera, Inc.*, "Natera, Inc.'s Answer and Affirmative Defenses [Demand for Jury Trial]" Case No. 3:18-CV-01662-SI, U.S. Pat. No. 9,493,831, dated Jul. 10, 2018, 9 pages.
*Illumina, Inc.* v. *Natera, Inc.*, "Order Denying Motion to Dismiss," Case No. 18-cv-01662-SI, U.S. Pat. No. 9,493,831, dated Jun. 26, 2018, 7 pages.
Illumina, Inc., Multiplexed Sequencing with the Illumina Genome Analyzer System, Illumina, 2008.
Illumina, Inc., Preparing Samples for Multiplexed Paired-End Sequencing (Dec. 2008).
International Human Genome Sequencing Consortium, Finishing the euchromatic sequence of the human genome. Nature vol. 431:931-945 (2004).
Jain et al., Improved data analysis for the Min/ON nanopore sequencer, Nature Methods, vol. 12:351-356 (2015).
Jury Verdict (D.I. 633) from *Verinata Health, Inc.* v. *Ariosa Diagnostics, Inc.*, Case No. 3:12-cv-5501-SI (N.D. Cal.), filed Jan. 25, 2018.
Lee et al., Quantitative assessment of HIV-1 DNA load by coamplification of HIV-1 gag and HLA-DQ-alpha genes, AIDS, vol. 5:683-691 (1991).
Lo & Rossa, Prenatal diagnosis: progress through plasma nucleic acids, Nature Reviews Genetics, vol. 8:71-77 (2007).
McKenna et al., The macaque gut microbiome in health, lentiviral infection, and chronic enterocolitis, PLOS Pathogens, vol. 4:e20 (2008).
Natera Assignment in U.S. Appl. No. 15/806,047, dated Nov. 7, 2017.
*Natera, Inc.* v. *Illumina, Inc.*, Patent Owner Illumina's Preliminary Response to Petition, Case No. IPR2018-01317, U.S. Pat. No. 9,493,831, dated Oct. 17, 2018, 75 pages.
*Natera, Inc.* v. *Illumina, Inc.*, "Petition for in Inter Partes Review," Case No. IPR2018-01317, U.S. Pat. No. 9,493,831, dated Jun. 29, 2018, 78 pages.
Natera's Jul. 2, 2018 Response filed in U.S. Appl. No. 15/806,047.
Natera's Oct. 9, 2018 Response filed in U.S. Appl. No. 15/806,047.
Newton et al., Analysis of any point mutation in DNA. The amplification refractory mutation system (ARMS), Nucleic Acids Research, vol. 17:2503-2516 (1989).
Poon et al., Presence of fetal RNA in maternal plasma, Clinical Chemistry, vol. 46:1832-1834 (2000).
Rothberg et al., An integrated semiconductor device enabling non-optical genome sequencing, Nature, vol. 475:348-352 (2011).
Saiki et al., Enzymatic amplification of /3-globin genomic sequences and restriction site analysis for diagnosis of sickle cell anemia, Science, vol. 230:1350-1354 (Dec. 20, 1985).
Saiki et al., Primer-directed enzymatic amplification of DNA with a thermostable DNA polymerase, Science, vol. 239:487-491 (Jan. 29, 1988).
Simmonds et al., Human immunodeficiency virus-infected individuals contain provirus in small numbers of peripheral mononuclear cells and at low copy numbers, Journal of Virology, vol. 64:864-872 (1990).
Sykes et al., Quantitation of target for PCR by use of limiting dilution, Biotechniques, vol. 13:444-449 (1992).
Tewhey et al., Microdroplet-based PCR enrichment for largescale targeted sequencing, Nature Biotechnology, vol. 27:1025-1031 (2009).
Zhang et al., Detection, quantification and sequencing of HIV-1 from the plasma of seropositive individuals and from factor VIII concentrates, AIDS, vol. 5:675-681 (1991).
Decision Denying Institution of Inter Partes Review: IPR2018-01317, U.S. Pat. No. 9,493,831 B2 (*Natera, Inc.* v. *Illumina, Inc.*), entered Jan. 15, 2019.

\* cited by examiner

Fig. 3

| Primer | cf Plasma DNA | | | | | | | | | Genomic DNA |
|---|---|---|---|---|---|---|---|---|---|---|
| | 24107 | 11215 | 11205 | 24101 | 24102 | 24103 | 24111 | 24106 | | Non-Pregnant |
| 1-150 | 12.48 | 13.87 | 15.27 | 9.49 | 11.47 | 15.13 | 10.94 | 16.44 | | 24.31 |
| 3_150 | 15.63 | 9.34 | 10.32 | No Data | 9.11 | 13.43 | 16.39 | 11.58 | | 22.97 |
| 4_150 | 14.33 | 7.78 | 8.55 | No Data | 7.18 | 10.17 | 12.18 | 10.12 | | 22.52 |
| 6_150 | 9.47 | 9.57 | 7.91 | 6.6 | 9.4 | 10.24 | 10.07 | No Data | | 20.57 |
| 5_150 | 4.83 | 3.08 | 3.39 | 3.82 | 4.2 | 3.74 | 9.46 | 8.31 | | 12.82 |
| 2_150 | 7.81 | 5.85 | 5.19 | No Data | 4.59 | 6.19 | 11.08 | 9.07 | | 8.81 |
| 7_150 | 2.27 | 3.75 | 3.91 | 2.63 | 4.71 | 4.01 | 4.59 | No Data | | 8.16 |

ND: Not Detectable
Conc. ng / ul

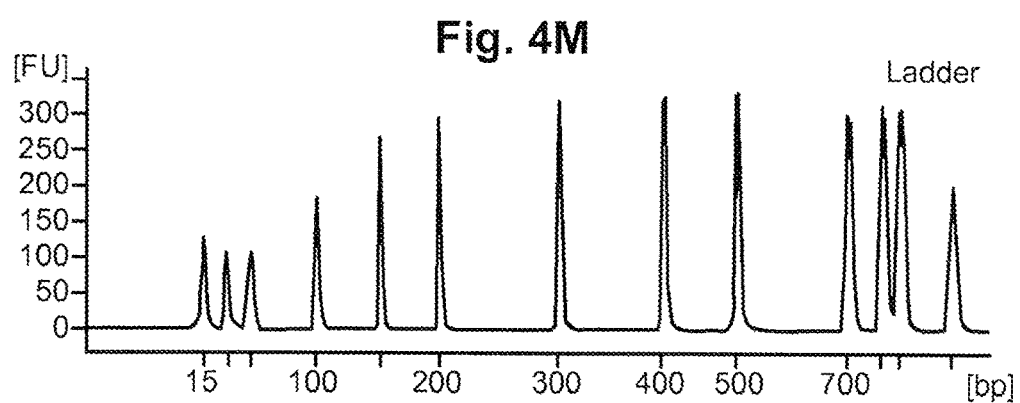

Fig. 5

| Sample ID | Ch21 Primer | Conc. ng / ul |
|---|---|---|
| 1 | 1_150 | 10.94 |
| 1 | 2_150 | 11.08 |
| 1 | 3_150 | 16.39 |
| 1 | 4_150 | 12.18 |
| 1 | 5_150 | 9.46 |
| 2 | 1_150 | 16.44 |
| 2 | 2_150 | 9.07 |
| 2 | 3_150 | 11.58 |
| 2 | 4_150 | 10.12 |
| 2 | 5_150 | 8.31 |
| 3 | 1_150 | 11.72 |
| 3 | 2_150 | 8.66 |
| 3 | 3_150 | 11.32 |
| 3 | 4_150 | 9.93 |
| 3 | 5_150 | 9.69 |

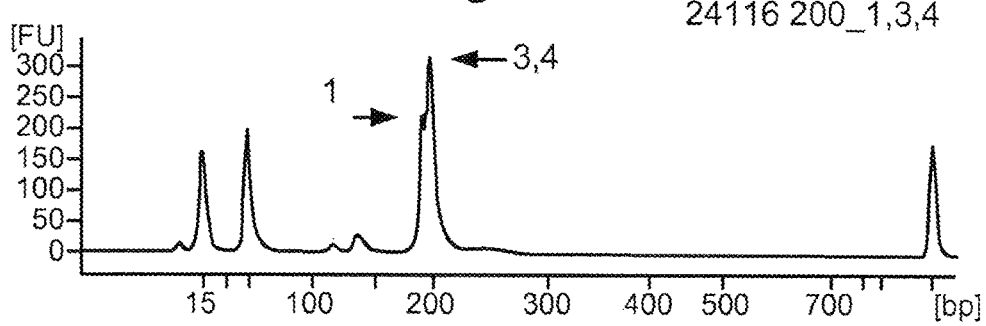
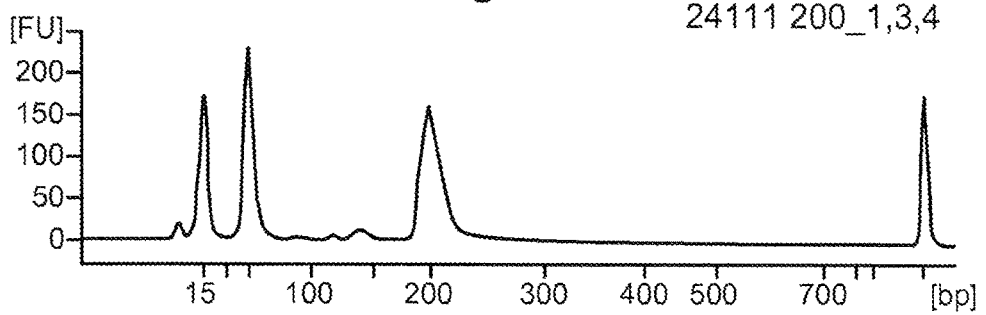
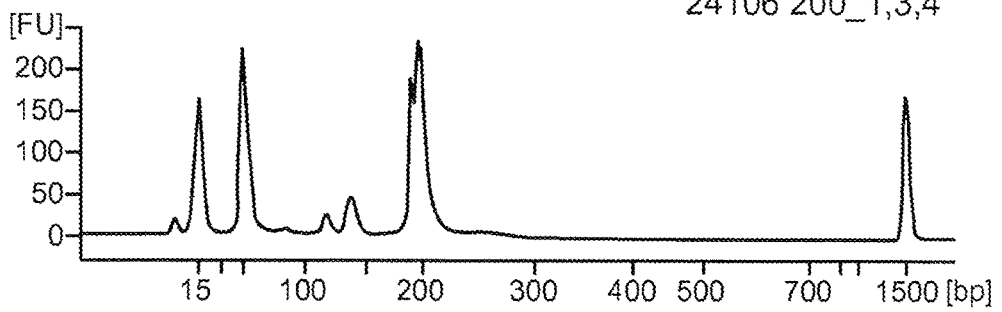
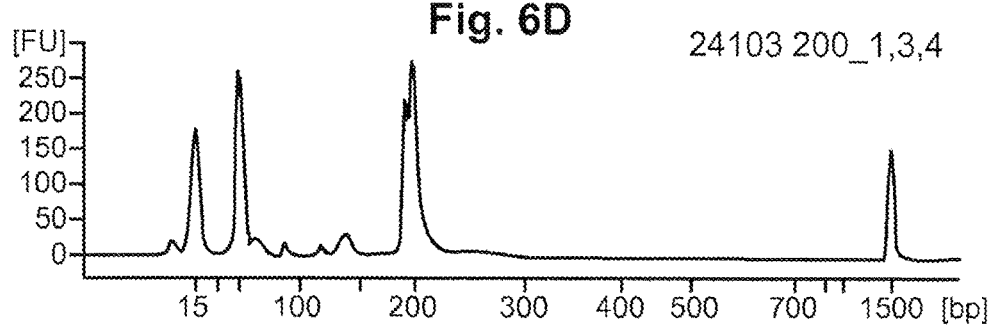

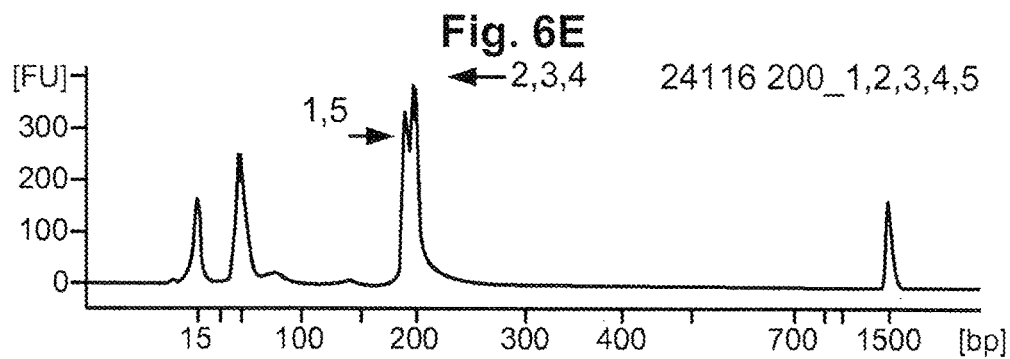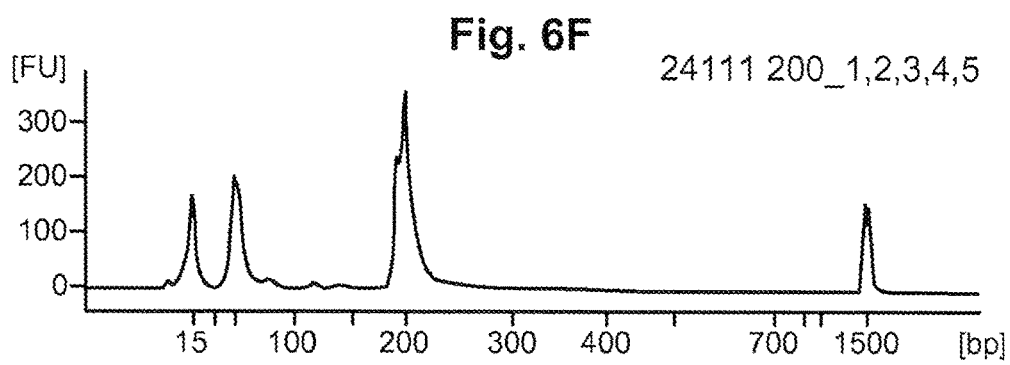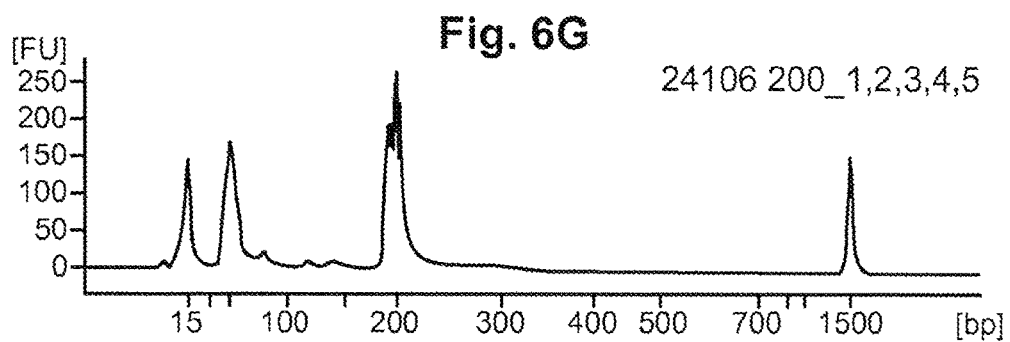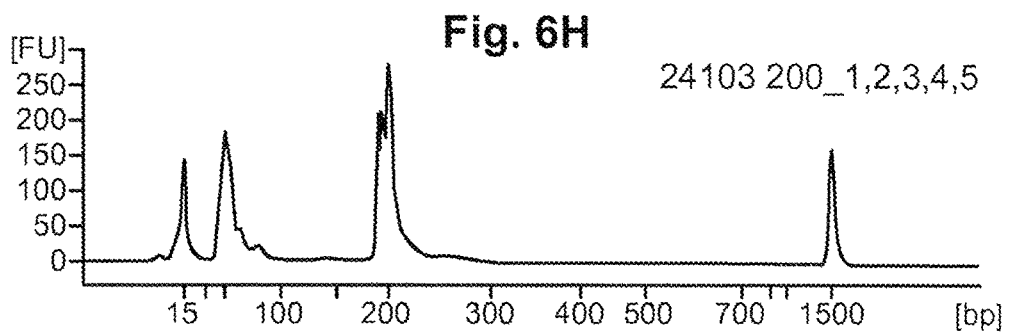

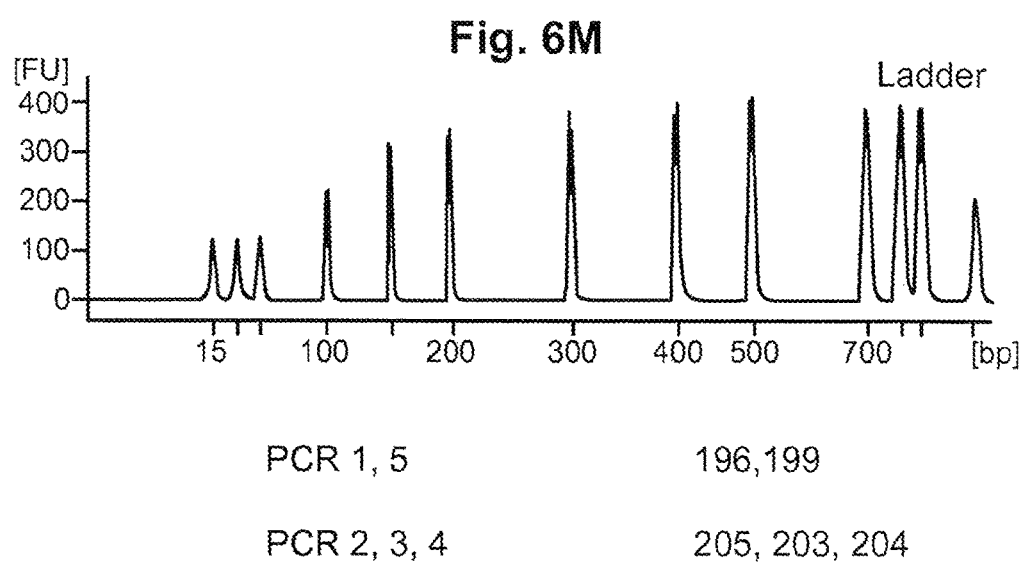

Fig. 8A

| A | | ch1 dPCR counts | ch21 dPCR counts | Ch21 / Ch1 Ratio |
|---|---|---|---|---|
| Ch21_1 / Ch1 | 24111; PCR Enrichment Ch1_1 Ch21_1 | 0 $21 \times 5 \times 10^5$ | $463 \times 5 \times 10^5$ $311 \times 5 \times 10^5$ | $463 \times 5 \times 10^5$ 14.81 |
| | 24111; cf plasma DNA Ch1_1 Ch21_1 | 235 | 383 | 1.63 |
| Ch21_2 / Ch1 | 24111; PCR Enrichment Ch1_1 Ch21_2 | 0 $10 \times 5 \times 10^5$ | $100 \times 5 \times 10^5$ $54 \times 5 \times 10^5$ | $100 \times 5 \times 10^5$ 5.4 |
| | 24111; cf plasma DNA Ch1_1 Ch21_2 | 177 | 236 | 1.33 |
| Ch21_5 / Ch1 | 24111; PCR Enrichment Ch1_1 Ch21_5 | 0 $10 \times 5 \times 10^5$ | $44 \times 5 \times 10^5$ $90 \times 5 \times 10^5$ | $44 \times 5 \times 10^5$ 9 |
| | 24111; cf plasma DNA Ch1_1 Ch21_5 | 212 | 332 | 1.57 |
| Ch21_7 / Ch1 | 24111; PCR Enrichment Ch1_1 Ch21_7 | 1 $24 \times 5 \times 10^5$ | $606 \times 10^3$ $8 \times 5 \times 10^5$ | $606 \times 10^3$ 0.33 |
| | 24111; cf plasma DNA Ch1_1 Ch21_7 | 207 | 131 | 0.63 |
| Ch1 | 24111; cf plasma DNA Ch1_1 | $7 \times 10^6$ | | |
| | | 199 | | |
| T21 Cellular DNA | T21 Cellular gDNA PCR Enrichment Ch21_7 / Ch1_1 | $2550 \times 10^3$ | $511 \times 10^3$ | 0.20 |
| | T21 Cellular gDNA Ch1_1 Ch21_7 | $46 \times 2 \times 10^3$ | $50 \times 2 \times 10^3$ | 1.09 |

Fig. 12

| Primer pair 18 | Sequence (5'->3') | Strand on template | Length | Start | Stop | Tm | GC% |
|---|---|---|---|---|---|---|---|
| Forward | TGAAGCCCGGGAGGTTCCCT | Plus | 20 | 22632815 | 22632834 | 59.16 | 65.00% |
| Reverse | TCCAGGCTGTGTGCCCTCCC | Minus | 20 | 22632954 | 22632935 | 60.47 | 70.00% |
| Internal oligo | | Plus | | | | | |
| Product length | 140 | | | | | | |

Fig. 15

| Ch21 Regions | Primer | ID cf Plasma DNA | | | | | | Genomic DNA |
|---|---|---|---|---|---|---|---|---|
| | | 24107 | 11215 | 11205 | 24101 | 24102 | | Non-Pregnant |
| Region A (7 Clusters) | A2 | ND | ND | ND | ND | ND | | ND |
| | A28 | ND | ND | ND | ND | ND | | ND |
| | A7 | 5.87 | 5.21 | 4.83 | 5.09 | 2.97 | | 10.54 |
| | A18 | 2.71 | 1.87 | 3.1 | 2.68 | 4.74 | | 9.31 |
| | A73 | 4.21 | 3.29 | 3.99 | 2.22 | 1.95 | | 7.96 |
| | A25 | 1.44 | ND | ND | 1.4 | ND | | 2.49 |
| | A72 | 1.94 | 1.47 | ND | 1.7 | 2.34 | | 1.86 |
| Region B (6 Clusters) | B19 | ND | ND | ND | ND | ND | | ND |
| | B54 | 15.15 | 6.02 | 15.6 | 11.39 | 10.87 | | 25.22 |
| | B16 | 3.83 | 2.57 | No Data | 1.9 | 2.59 | | 13.14 |
| | B7 | 4.77 | 2.57 | 3.47 | 17.29 | 3.93 | | 4.8 |
| | B32 | ND | ND | 1.47 | ND | ND | | 3.24 |
| | B34 | ND | ND | ND | ND | ND | | 2.09 |
| Region C (8 Clusters) | C55 | 12.36 | 8.59 | 15.27 | 6.82 | 10.06 | | 25.74 |
| | C72 | 8.57 | 5.87 | 10.97 | 7.38 | 8.41 | | 16.40 |
| | C74 | 9.09 | 5.61 | 6.74 | 5.52 | 5.69 | | 15.51 |
| | C19 | 8.34 | 4.97 | 7.27 | 6.27 | 6.98 | | 11.06 |
| | C29 | 11.14 | 4.67 | 6.47 | 6.69 | 6.6 | | 7.83 |
| | C1 | 3.87 | 2.17 | 3.59 | 3.62 | 4.48 | | 4.69 |
| | C6 | ND | 1.96 | 2.55 | ND | 2.12 | | 3.37 |
| | C58 | ND | ND | ND | ND | ND | | 0.97 |

ND: Not Detectable    Conc. ng / ul

Fig. 17

|  | ID of Plasma DNA | | | | | | | Genomic DNA |
|---|---|---|---|---|---|---|---|---|
| Primer | 24107 | 11215 | 11205 | 24101 | 24102 | 24103 | 24109 | Non-Pregnant |
| Ch1_1_150 | 15.54 | 14.93 | 14.13 | 10.99 | 18.28 | 17.15 | 13.75 | 30.28 |
| Ch1_2_150 | 15.15 | 9.94 | 12.6 | 7.69 | 6.98 | 9.69 | 8.65 | 19.44 |
| Ch2_1-150 | 5.84 | 5.92 | 5.51 | 3.94 | 5.86 | 6.4 | 3.79 | 12.66 |
| Ch2_2_150 | 3.45 | 2.84 | 2.96 | 2.63 | 2.94 | 3.24 | 2.04 | 7.63 |
| Ch3_1_150 | 6.12 | 4.18 | 6.91 | 4.1 | 5.73 | 5.14 | 4.22 | 11.44 |

Conc. ng / ul

Fig. 18

|  | Chromosome Walk | Sequencing Data |
|---|---|---|
| Ch21 Enrichment | 76% Amplification (16 / 21) | 100% Amplification (7 / 7) |
| Ref Ch1, 2, 3 Enrichment | | 100% Amplification (5 / 5) |

Chromosome 21 – 47 Mb

Combine Sequence Runs

Cover 37 Mb regions
79% of Ch21

Individual / lane
10M reads / lane X 36 base / read = 360 M base
3000 M base / Genome
Coverage = 0.1 x 21p11.2

21q22.3

9757475

46927127

|  | Start | End |
|---|---|---|
| Sorted 0 | 9757475 | 9999942 |
| Sorted 1 | 10000038 | 19999476 |
| Sorted 2 | 20000278 | 29999849 |
| sorted 3 | 30000379 | 40000015 |
| sorted 4 | 40000033 | 46927127 |

Fig. 21
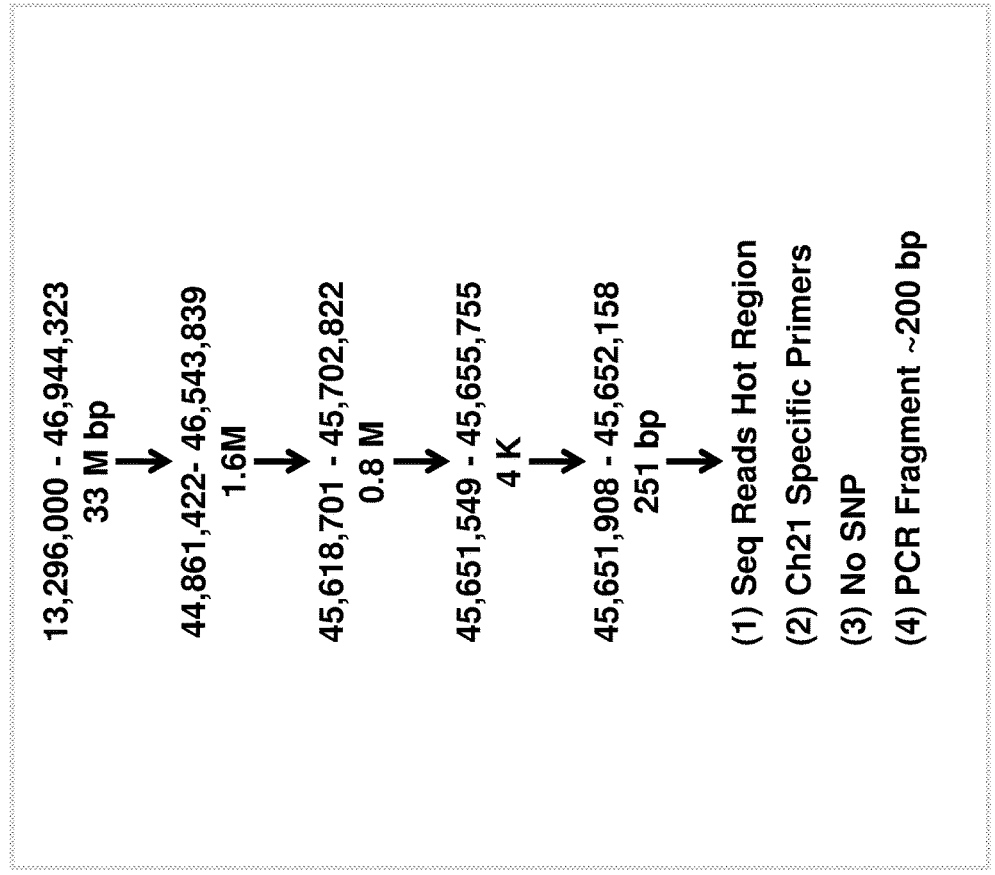
13,296,000 - 46,944,323
33 M bp
→
44,861,422 - 46,543,839
1.6M
→
45,618,701 - 45,702,822
0.8 M
→
45,651,549 - 45,655,755
4 K
→
45,651,908 - 45,652,158
251 bp
→
(1) Seq Reads Hot Region
(2) Ch21 Specific Primers
(3) No SNP
(4) PCR Fragment ~200 bp
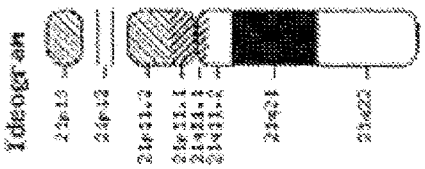

```
PRIMER PICKING RESULTS FOR chr21:45651908-45652152

No mispriming library specified
Using 1-based sequence positions
OLIGO            start  len   tm     gc%    any    3'    seq
LEFT PRIMER         49   21  59.72  57.14  4.00  0.00  GAGTCAAGTGAAGTGAAGCTGAGGA  (SEQ ID NO: 15)
RIGHT PRIMER       241   20  60.26  60.00  5.00  3.00  GGAGGTGCTAGTGGTGAAGCA    (SEQ ID NO: 16)
SEQUENCE SIZE: 251
INCLUDED REGION SIZE: 251

PRODUCT SIZE: 196, PAIR ANY COMPL: 4.00, PAIR 3' COMPL: 0.00

1 AACAGCCGTGACCCGAAGAGTGCTGTAGTCAGTCCTCAGAGTCAAGTGAAGTGAAGCTGA
 61 GGAAGAGGACTCTGTCACCGGGCAGTTGCTGATGCCCATGGCCAGGCCAGGAGGCTGGT      (SEQ ID NO: 133)
121 CTCATGAGTCTCCTTGTGTCTGAGCCCTCTTACACTCCACCATGGCATCAAGCTCTACC
181 CCTGCCTCCTTGCAGCCCCAGAGCCATGCATGTCTGCCCCTCCTCACCACTAGGACCTC
241 CTCCTGTCTGG
```

METHODS OF FETAL ABNORMALITY DETECTION

CROSS-REFERENCE

This application is a continuation of U.S. Utility application Ser. No. 14/677,854 filed Apr. 2, 2015 which is a continuation of U.S. Utility application Ser. No. 13/792,661 filed Mar. 11, 2013 which is a continuation of U.S. Utility application Ser. No. 13/012,222 filed Jan. 24, 2011 which claims priority to U.S. Provisional Application No. 61/297,755, filed Jan. 23, 2010, which applications are incorporated herein by reference.

SEQUENCE LISTING

The instant application contains a Sequence Listing which has been submitted in ASCII format via EFS-Web and is hereby incorporated by reference in its entirety. Said ASCII copy, created on Sep. 12, 2014, is named 32047-769.302_SL.txt and is 27,831 bytes in size. No new matter has been added.

BACKGROUND OF THE INVENTION

Massively parallel sequencing techniques are used for detection of fetal aneuploidy from samples that comprise fetal and maternal nucleic acids. Fetal DNA often constitutes less than 10% of the total DNA in a sample, for example, a maternal cell-free plasma sample. Sequencing a large number of polynucleotides to generate sufficient data for fetal aneuploidy detection can be expensive. Methods for randomly enriching fetal nucleic acids in cell-free maternal sample have been described, including enriching nucleic acids based on size, formaldehyde treatment, methylation status, or hybridization to oligonucleotide arrays. There is a need for a means of selectively enriching non-random fetal and maternal polynucleotide sequences in a way that facilitates aneuploidy detection by massively parallel sequencing techniques and increases the sensitivity of aneuploidy detection.

SUMMARY OF THE INVENTION

In one aspect, a method for determining the presence or absence of fetal aneuploidy is provided comprising a) selectively enriching non-random polynucleotide sequences of genomic DNA from a cell-free DNA sample; b) sequencing said enriched polynucleotide sequences; c) enumerating sequence reads from said sequencing step; and d) determining the presence or absence of fetal aneuploidy based on said enumerating. In one embodiment, said selectively enriching comprises performing PCR. In another embodiment, said selectively enriching comprises linear amplification. In another embodiment, said selectively enriching comprises enriching at least 1, 5, 10, 50, 100, or 1000 non-random polynucleotide sequences from a first chromosome. In another embodiment, said selectively enriching comprises enriching at least 1, 10, or 100 polynucleotide sequences from one or more regions of a first chromosome, wherein each region is up to 50 kb. In another embodiment, said non-random polynucleotide sequences comprise sequences that are sequenced at a rate of greater than 5-fold than other sequences on the same chromosome. In another embodiment, said non-random polynucleotide sequences each comprise about 50-1000 bases. In another embodiment, said cell-free DNA sample is a maternal sample. In another embodiment, said maternal sample is a maternal blood sample. In another embodiment, said maternal sample comprises fetal and maternal cell-free DNA. In another embodiment, said cell-free DNA is from a plurality of different individuals.

In another embodiment, said sequencing comprises Sanger sequencing, sequencing-by-synthesis, or massively parallel sequencing.

In another embodiment, said aneuploidy is trisomy 21, trisomy 18, or trisomy 13. In another embodiment, said aneuploidy is suspected or determined when the number of enumerated sequences is greater than a predetermined amount. In another embodiment, said predetermined amount is based on estimated amount of DNA in said cell-free DNA sample. In another embodiment, said predetermined amount is based on the amount of enumerated sequences from a control region.

In another aspect, a method is provided comprising: a) providing oligonucleotides that specifically hybridize to one or more polynucleotide sequences from a polynucleotide template, wherein said one or more polynucleotide sequences comprise sequences that are sequenced at rate greater than 5-fold than other sequences from the polynucleotide template; b) selectively enriching said one or more polynucleotide sequences; and c) optionally sequencing said enriched one or more polynucleotide sequences.

In another embodiment, each of said oligonucleotides has a substantially similar thermal profile. In another embodiment, said polynucleotide sequences each comprise about 50-1000 bases. In another embodiment, said polynucleotide sequences are from a cell-free DNA sample. In another embodiment, said polynucleotide sequences are from a maternal sample. In another embodiment, said maternal sample is a maternal blood sample. In another embodiment, said maternal sample comprises fetal and maternal cell-free DNA. In another embodiment, said polynucleotide template is a chromosome suspected of being aneuploid. In another embodiment, said polynucleotide template is chromosome 21. In another embodiment, the polynucleotide template is a chromosome not suspected of being aneuploid. In another embodiment, said polynucleotide template is chromosome 1, 2, 3, 4, 5, 6, 7, 8, 9, 10, 11, 12, 14, 15, 16, 17, 19, 20, or 22.

In another embodiment, said rate is at least 10 or 50-fold. In another embodiment, there are at least 7, 10, 17, or 27 sequence reads for the sequences that were sequenced at a higher frequency rate. In another embodiment, said selectively enriching comprises performing PCR. In another embodiment, said selectively enriching comprises linear amplification. In another embodiment, said selectively enriching comprises enriching at least 1, 5, 10, 50, 100, or 1000 non-random polynucleotide sequences from a first chromosome. In another embodiment, said selectively enriching comprises enriching at least 1, 10, or 100 polynucleotide sequences from one or more regions of a first chromosome, wherein each region is up to 50 kb. In another embodiment, said sequencing comprises Sanger sequencing, sequencing-by-synthesis, or massively parallel sequencing.

In another embodiment, the method further comprises a step of determining the presence of absence of fetal aneuploidy based on said sequencing In another aspect, a method for identifying polynucleotide sequences for enrichment in a polynucleotide template is provided comprising: a) sequencing a plurality of polynucleotide sequences from the polynucleotide template; b) enumerating sequenced polynucleotide sequences; and c) identifying one or more sequenced polynucleotide sequences that are sequenced or that have a coverage rate at least 5-fold greater than a second set of polynucleotide sequences.

In one embodiment, said polynucleotide sequences are from a cell-free DNA sample. In another embodiment, said polynucleotide sequences are from a maternal sample. In another embodiment, said sequencing coverage rate is at least 10- or 50-fold. In another embodiment, there are at least 7, 10, 17, or 27 reads for the polynucleotide sequences that were sequenced at a higher frequency rate.

In another embodiment, said identified polynucleotide sequences are used to determine the presence or absence of fetal aneuploidy.

In another aspect, a kit comprising a set of oligonucleotides that selectively amplify one or more regions of a chromosome is provided, wherein each of said regions is sequenced at a rate of greater than 5-fold than other regions of the chromosome.

In one embodiment, each of said oligonucleotides in the kit is part of an oligonucleotide pair. In another embodiment, said set of oligonucleotides comprises at least 100 oligonucleotides. In another embodiment, an oligonucleotide in each oligonucleotide pair comprises sequence identical to sequence in an oligonucleotide in the other pairs and sequence unique to that individual oligonucleotide.

In another aspect, a method for sequencing cell-free DNA from a maternal sample is provided comprising: a) obtaining a maternal sample comprising cell-free DNA, b) enriching sequences that are representative of a plurality of up to 50 kb regions of a chromosome, or enriching sequences that are sequenced at a rate of at least 5-fold greater than other sequences using an Illumina Genome Analyzer sequencer, and c) sequencing said enriched sequences of cell-free DNA.

In one embodiment, said sequencing comprises sequencing-by-synthesis. In another embodiment, said method further comprises bridge amplification. In another embodiment, said sequencing comprises Sanger sequencing. In another embodiment, said sequencing comprises single molecule sequencing. In another embodiment, said sequencing comprises pyrosequencing. In another embodiment, said sequencing comprises a four-color sequencing-by-ligation scheme. In another embodiment, said sequenced enriched sequences are used to determine the presence or absence of fetal aneuploidy. In another aspect, one or more unique isolated genomic DNA sequences are provided, wherein said genomic DNA sequences comprise regions that are sequenced at a rate greater than 500% than other regions of genomic DNA. In another embodiment, the isolated genomic DNA are sequenced by a method comprising bridge amplification, Sanger sequencing, single molecule sequencing, pyrosequencing, or a four-color sequencing by ligation scheme. In another embodiment, the isolated genomic regions comprise at least 100, 1000, or 10,000 different sequences. In another embodiment, the regions are present at a rate greater than 50-fold, 100-fold, 20-fold. In another embodiment, the sequence is a single amplicon.

In another aspect, a set of one or more oligonucleotides are provided that selectively hybridize to one or more unique genomic DNA sequences, wherein said genomic DNA sequences comprise regions that are sequenced at a rate greater than 500% than other regions of genomic DNA. In one embodiment, the oligonucleotides hybridize to the sequences under mild hybridization conditions. In another embodiment, the oligonucleotides have similar thermal profiles.

In another aspect, a method is provided comprising: a) amplifying one or more polynucleotide sequences with a first set of oligonucleotide pairs; b) amplifying the product of a) with a second set of oligonucleotides pairs; and c) amplifying the product of b) with a third set of oligonucleotide pairs. In one embodiment, the first set of oligonucleotide pairs comprises sequence that distinguishes polynucleotides in one sample from polynucleotides in another sample. In another embodiment, said first set of oligonucleotide pairs comprises sequence that distinguishes polynucleotides in one sample from polynucleotides in another sample and sequence that extends the length of the product. In another embodiment, said polynucleotide sequences are enriched sequences.

In another aspect, a method for labeling enriched polynucleotides in two or more samples that allows identification of which sample the polynucleotide originated is provided, comprising: a) amplifying one or more polynucleotide sequences in two or more samples with a first set of oligonucleotide pairs, wherein the first set of oligonucleotide pairs comprises sequence that distinguishes polynucleotides from one sample from polynucleotides in another sample; b) amplifying the product of a) with a second set of oligonucleotides pairs; and c) amplifying the product of b) with a third set of oligonucleotide pairs.

In another aspect, a kit is provided comprising a) a first set of oligonucleotide primer pairs comprising: sequence that selectively hybridizes to a first set of genomic DNA sequences and sequence in-common amongst each of the first set of oligonucleotide primer pairs, b) a second set of oligonucleotide primer pairs with sequence that selectively hybridizes to the common sequence of the first set of oligonucleotide primer pairs and sequence common to the second set of oligonucleotide pairs, and c) a third set of oligonucleotide primer pairs with sequence that selectively hybridizes to the common sequence of the second set of oligonucleotide pairs. In one embodiment, the common region in the first set of primers comprises sequence that distinguishes polynucleotides in one sample from polynucleotides in another sample. In another embodiment, the common region in the first set of primers comprises sequence that distinguishes polynucleotides in one sample from polynucleotides in another sample and sequence that extends the length of the product.

In another aspect, a kit is provided comprising: a first set of primer pairs that selectively amplifies a set of genomic sequences to create a first set of amplification products, a second set of primer pair that selectively amplifies the first set of amplification products, and a third set of primer pairs that selectively amplifies the second set of amplification products.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 illustrates results of amplification of chromosome 21 with different primer pairs.

FIGS. 4A-M illustrate simplex PCR amplification Bioanalyzer results.

FIG. 5 illustrates simplex PCR amplification Bioanalyzer results.

FIGS. 6A-M illustrate multiplex PCR amplification Bioanalyzer results.

FIG. 10 discloses SEQ ID NOS 9-10 and 96-98, respectively, in order of appearance.

FIG. 12 illustrates a primer pair (SEQ ID NOS 42-43, respectively, in order of appearance) designed for use in PCR amplification.

FIG. 15 illustrates enrichment of regions of chromosome 21 using the "chromosome walk" sequence selection method.

FIG. 17 illustrates enrichment of sequences from reference chromosomes 1, 2, and 3.

FIG. 18 illustrates chromosome amplification rates of sequences selected using the "chromosome walk" method or based on "hot spots."

FIG. 21 illustrates criteria used to select and amplify a "hot spot" region of chromosome 21.

FIG. 25 illustrates primers (SEQ ID NOS 15-16, respectively, in order of appearance) designed for amplifying sequence from a 251 bp segment of chromosome 21(SEQ ID NO: 133).

DETAILED DESCRIPTION OF THE INVENTION

Overview

Figure 1:
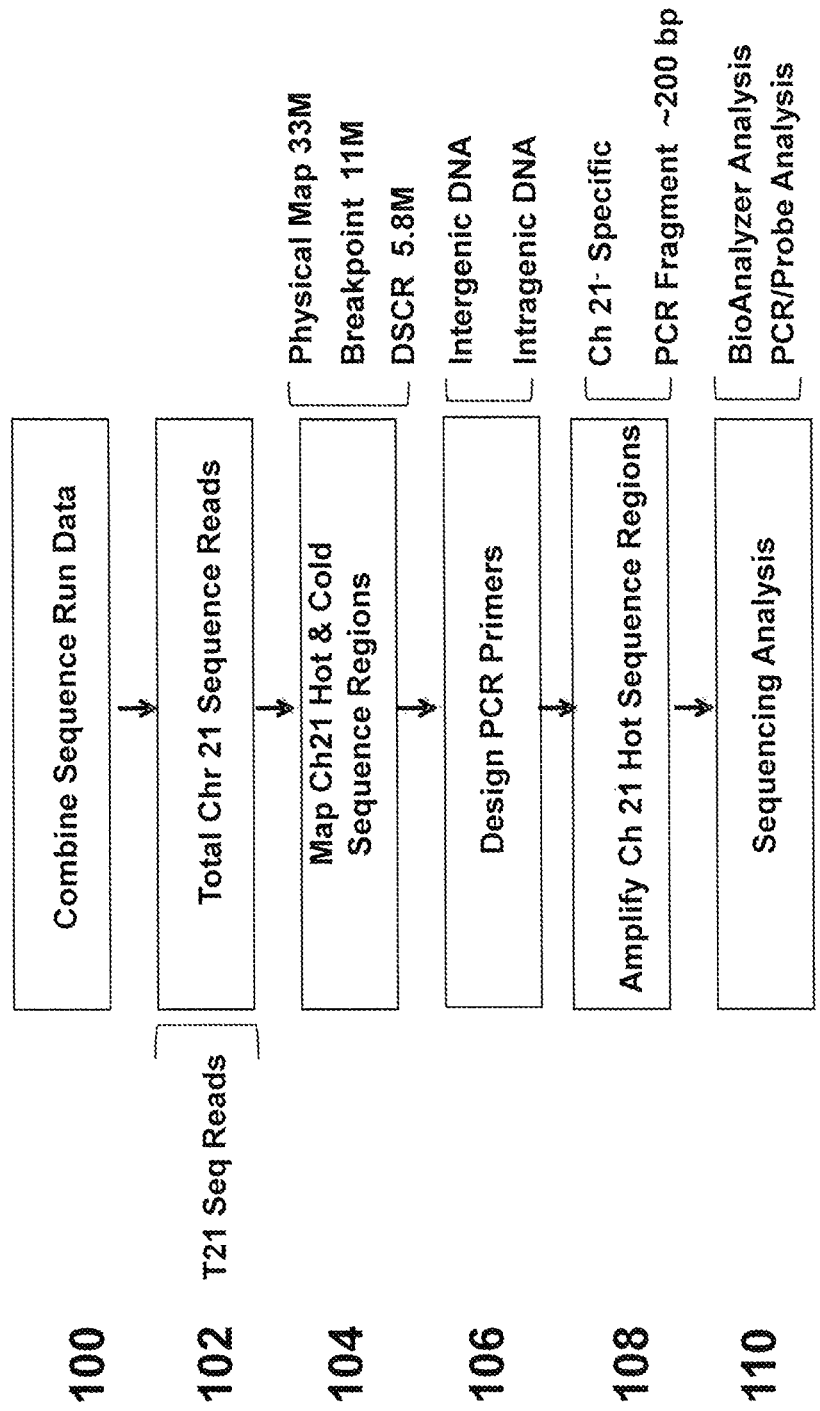
FIG. 1 illustrates a strategy for selecting sequences for enrichment based on "hot spots."

In one aspect, the provided invention includes methods for selecting non-random polynucleotide sequences for enrichment. The non-random sequences can be enriched from a maternal sample for use in detecting a fetal abnormality, for example, fetal aneuploidy. In one embodiment, the selection of non-random polynucleotide sequences for enrichment can be based on the frequency of sequence reads in a database of sequenced samples from one or more subjects. In another embodiment, the selection of polynucleotide sequences for enrichment can be based on the identification in a sample of sequences that can be amplified in one or more regions of a chromosome. The selection of polynucleotide sequences to enrich can be based on knowledge of regions of chromosomes that have a role in aneuploidy. The selective enrichment of sequences can comprise enriching both fetal and maternal polynucleotide sequences.

In another aspect, the provided invention includes methods for determining the presence or absence of a fetal abnormality comprising a step of enriching non-random polynucleotide sequences from a maternal sample. The non-random polynucleotide sequences can be both fetal and maternal polynucleotide sequences.

In another aspect, the provided invention comprises a kit comprising oligonucleotides for use in selectively enriching non-random polynucleotide sequences.

In another aspect, the provided invention includes methods for generating a library of enriched polynucleotide sequences. A library can be generated by the use of one or more amplification steps, which can introduce functional sequences in polynucleotide sequences that have been selectively enriched. For example, the amplification steps can introduce sequences that serve as hybridization sites for oligonucleotides for sequencing, sequences that identify that sample from which the library was generated, and/or sequences that serve to extend the length of the enriched polynucleotide sequences, for example, to facilitate sequencing analysis.

In one aspect, a method for determining the presence or absence of fetal aneuploidy is provided comprising selectively enriching non-random polynucleotide sequences (e.g., genomic DNA) from a cell-free nucleic acid (e.g., DNA or RNA) sample, sequencing said enriched polynucleotide sequences, enumerating sequence reads from said sequencing step, and determining the presence or absence of fetal aneuploidy based on said enumerating.

The selectively enriching step can comprise amplifying nucleic acids. Amplification can comprise performing a polymerase chain reaction (PCR) on a sample of nucleic acids. PCR techniques that can be used include, for example, digital PCR (dPCR), quantitative PCR (qPCR) or real-time PCR (e.g., TaqMan PCR; Applied Biosystems), reverse-transcription PCR (RT-PCR), allele-specific PCR, amplified fragment length polymorphism PCR (AFLP PCR), colony PCR, Hot Start PCR, in situ PCR (ISH PCR), inverse PCR (IPCR), long PCR, multiplex PCR, or nested PCR. Amplification can be linear amplification, wherein the number of copies of a nucleic acid increases at a linear rate in a reaction.

The selectively enriching step can comprise a hybridization step. The hybridization can occur on a solid support.

Selecting Sequences Based on "Hotspots"

Sequencing data can be analyzed to identify polynucleotide sequences to be selectively enriched. Some polynucleotide sequences from a sample comprising nucleic acids (e.g., genomic DNA) can be sequenced at a higher frequency than other polynucleotide sequences. These sequences may be more likely to be enriched by, for example, amplification methods. Identifying and enriching these polynucleotide sequences can reduce the number of nucleic acids that need to be analyzed to determine the presence or absence of fetal aneuploidy. This enrichment can reduce the cost of aneuploidy determination.

In one embodiment, the non-random polynucleotide sequences that are selectively enriched can comprise sequences that are sequenced at a frequency of greater than at least 2-, 3-, 4-, 5-, 6-, 7-, 8-, 9-, 10-, 15-, 20-, 25-, 30-, 40-, 50-, 60-, 70-, 80-, 90-, or 100-fold than other sequences on the same chromosome in a database of sequence information. The polynucleotide sequences that are sequenced at a higher frequency can be referred to as "hot-spots." The non-random polynucleotides that are selectively enriched can be selected from regions of a chromosome known to have a role in a disease, for example, Down syndrome. The sequencing rate data can be derived from a database of enumerated polynucleotide sequences, and the database of enumerated polynucleotide sequences can be generated from one or more samples comprising non-maternal samples, maternal samples, or samples from subjects that are pregnant, have been pregnant, or are suspected of being pregnant. The samples can be cell-free nucleic acid (e.g., DNA or RNA) samples. The subjects can be mammals, e.g., human, mouse, horse, cow, dog, or cat. The samples can contain maternal polynucleotide sequences and/or fetal polynucleotide sequences. The enumerated sequences can be derived from random, massively parallel sequencing of samples, e.g., as described in U.S. Patent Application Publication Nos. 20090029377 and 20090087847, or Fan H C et al. (2008) *PNAS* 105:16266-71, which are herein incorporated by reference in their entireties. Techniques for massively parallel sequencing of samples are described below.

Figure 22A:
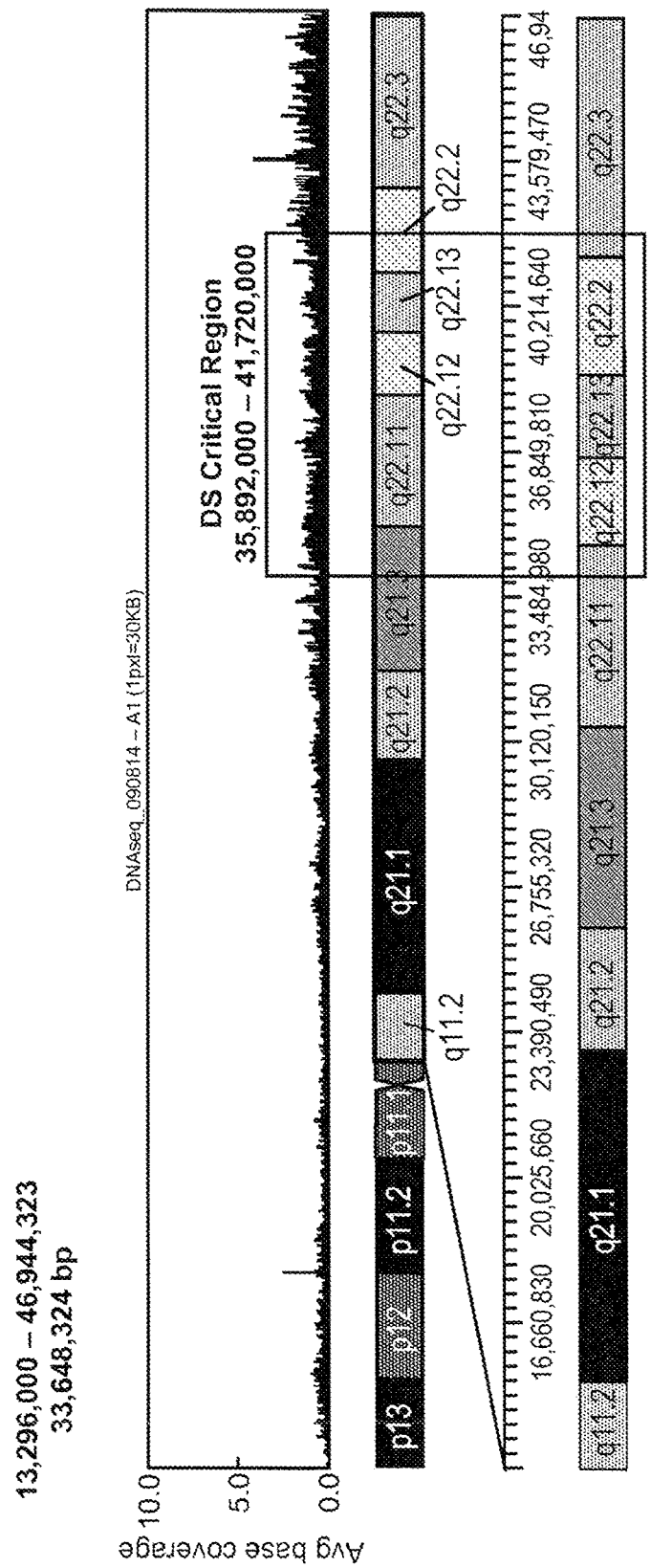
FIGS. 22A-C highlight a Down syndrome critical region on a schematic of sequence reads that map to chromosome 21.
Figure 22B:
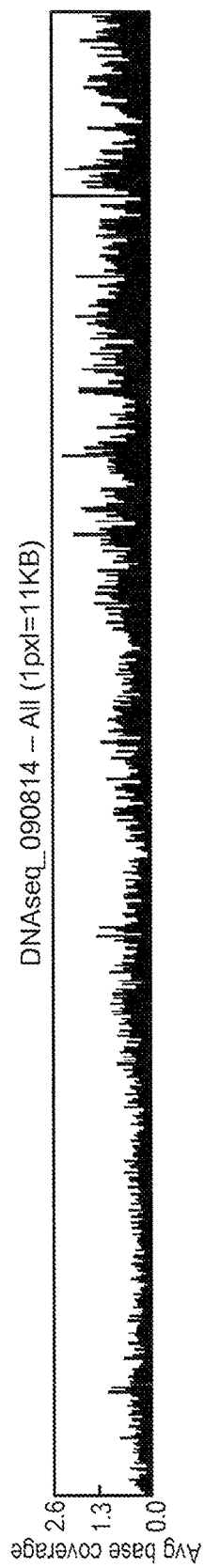
Figure 22C:
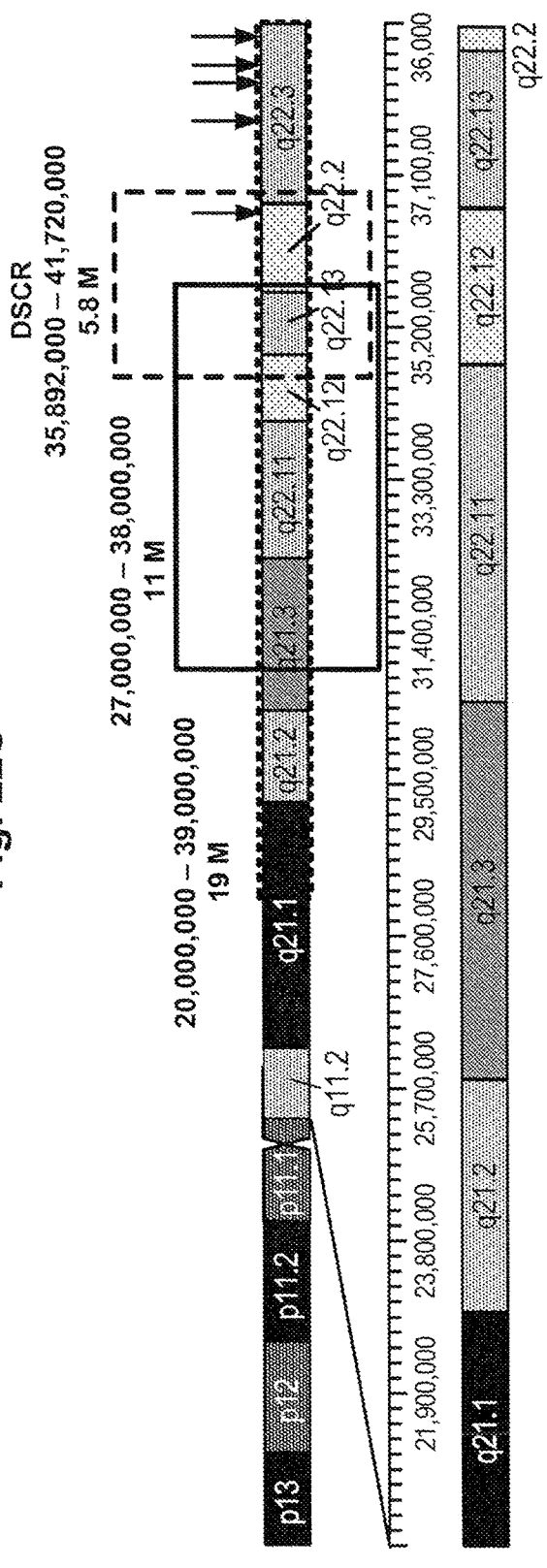
Figure 23:
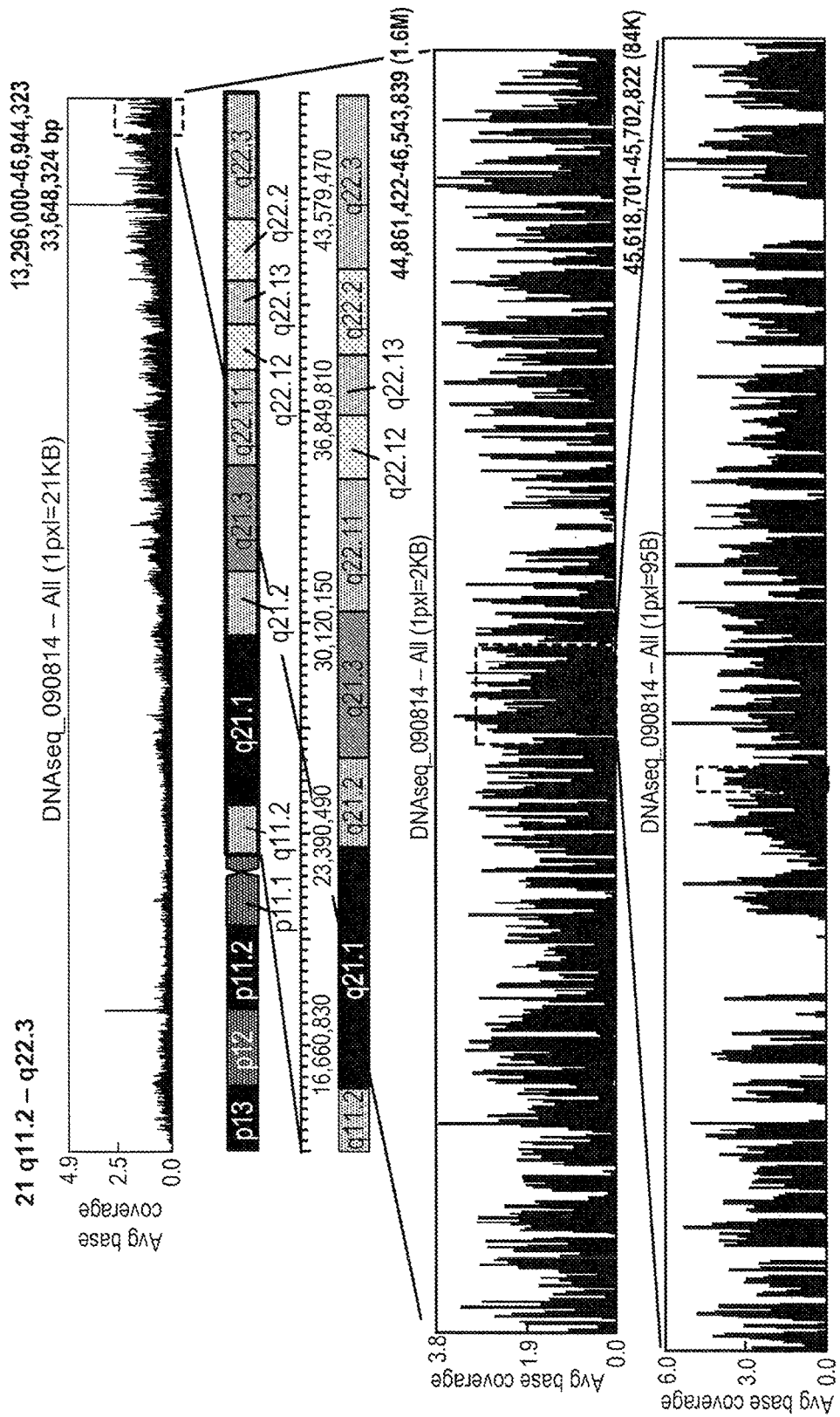
FIG. 23 magnifies regions of sequence read coverage on a schematic of chromosome 21.
Figure 24:
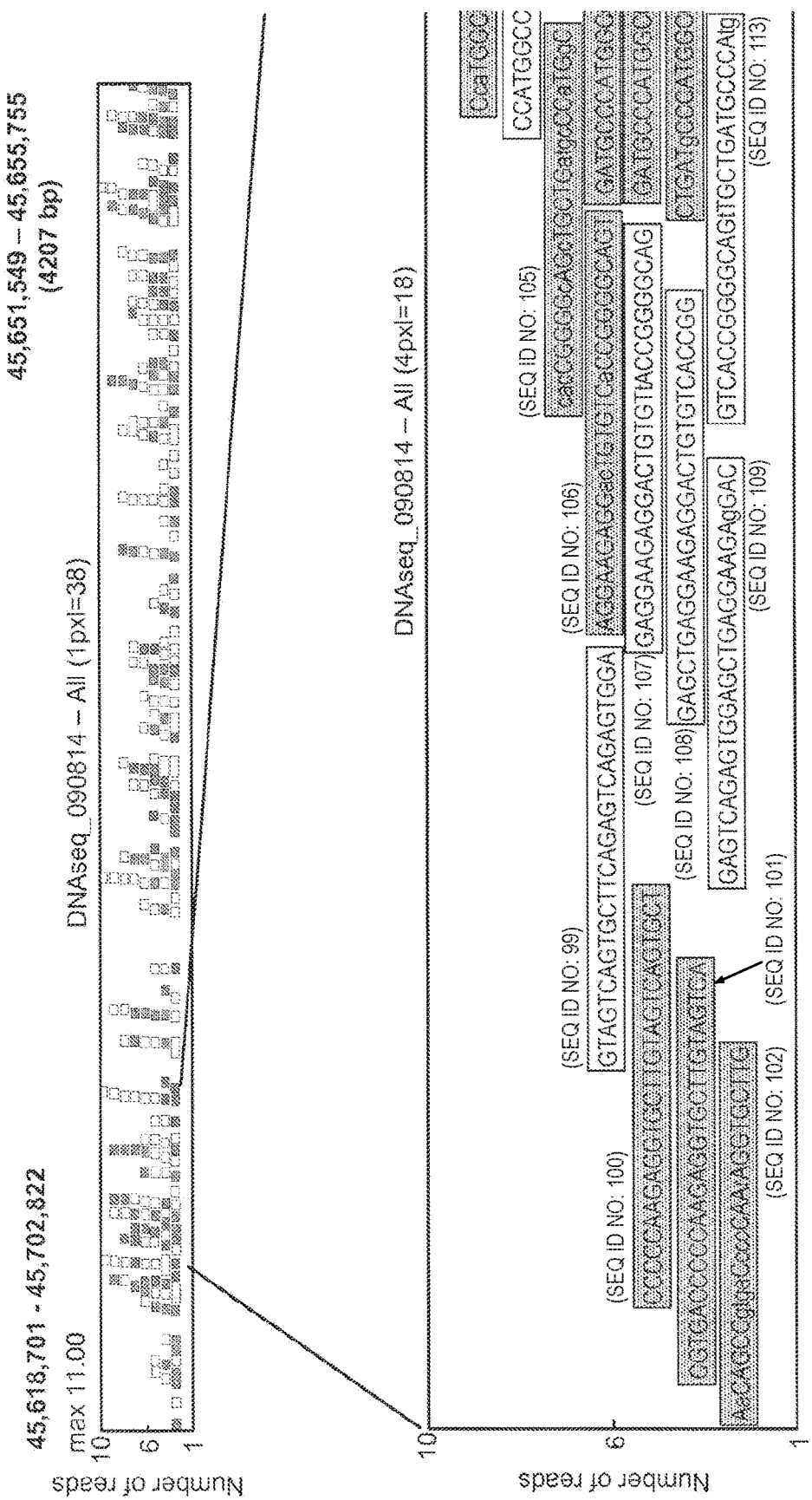
FIG. 24 illustrates sequences reads mapped on chromosome 21 (SEQ ID NOS 99-132, respectively, in order of appearance).

The database can comprise sequence information from samples from at least 1, 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100, 200, 300, 400, 500, 600, 700, 800, 900, 1000, 2000, 3000, 5000, 7500, 10,000, 100,000, or 1,000,000 different subjects. The data can be processed to indicate the overlap of individual polynucleotide sequences from the samples from the subjects (FIGS. 22-24). The database can indicate the frequency with which one or more nucleotides at a specific chromosome position is sequenced among the samples. The length of the sequence that can overlap can be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 125, 150, 175, 200, 225, 250, 275, or 300 bases. The frequency of sequencing of one or more nucleotides at a first position of a chromosome can be compared to the frequency of sequencing of one or more other nucleotides at a second position on the chromosome to determine the fold frequency at which the first position was sequenced relative to the second position. The sequence (polynucleotide sequence or base) that is sequenced at a higher frequency can be sequenced at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 200, 300, 400, 500, 600, 700, 800, 900, 1000, 2000, 3000, 5000, 7500, 10,000, 100,000, or 1,000,000 times in one or more samples in the database.

In one embodiment, a method for identifying polynucleotide sequences for enrichment in a polynucleotide template is provided comprising sequencing a plurality of polynucleotide sequences from the polynucleotide template, enumerating sequenced polynucleotide sequences, and identifying one or more sequenced polynucleotide sequences that are sequenced or that have a coverage rate at least 5-fold greater than a second set of polynucleotide sequences.

In another aspect, one or more unique isolated genomic DNA sequences are provided, wherein said genomic DNA sequences comprise regions that are sequenced at a rate greater than 5-fold than other regions of genomic DNA. The isolated genomic sequences can comprise at least 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 different sequences. Each isolated genomic sequence can be a single amplicon.

In another aspect, a set of one or more oligonucleotides that selectively hybridize to the isolated sequences is provided. The oligonucleotides can hybridize to the sequences under mild hybridization conditions. The oligonucleotides can have similar thermal profiles.

In one embodiment, the non-random sequences to be selectively enriched are identified based on the number of times they are sequenced in a database of sequence information, independent of the rate of sequencing of a second set of sequences. For example, the sequences to be selectively enriched can be those that are sequenced at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 200, 300, 400, 500, 600, 700, 800, 900, 1000, 2000, 3000, 5000, 7500, 10,000, 100,000, or 1,000,000 times in one or more samples in the database.

The number of non-random polynucleotide sequences that can be selectively enriched in a sample can be at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 150, 200, 250, 300, 400, 500, 600, 700, 750, 800, 900, or 1000. The size of the non-random polynucleotide sequences to be selectively enriched can comprise about 10-1000, 10-500, 10-260, 10-260, 10-200, 50-150, or 50-100 bases or bp, or at least 10, 15, 20, 25, 30, 35, 40, 45, 50, 55, 60, 66, 70, 75, 80, 85, 90, 95, 100, 110, 120, 130, 140, 150, 160, 170, 180, 190, 200, 210, 220, 230, 240, 250, 260, 270, 280, 290, 300, 400, 500, 600, 700, 800, 900, or 1000 bases or bp.

The selective enrichment step can comprise designing oligonucleotides (primers) that hybridize specifically to polynucleotide sequences that are sequenced at a higher frequency than other sequences on a chromosome or are sequenced a certain number of times. A program, for example, Basic Local Alignment Search Tool (BLAST), can be used to design oligonucleotides that hybridize to sequence specific to one chromosome or region. The oligonucleotide primers can be manually designed by a user, e.g., using known genome or chromosome sequence template as a guide. A computer can be used to design the oligonucleotides. The oligonucleotides can be designed to avoid hybridizing to sequence with one or more polymorphisms, e.g., single nucleotide polymorphisms (SNPs).

One or more oligonucleotide pairs can be generated to hybridize specifically to one or more polynucleotide sequences; the oligonucleotide pairs can be used in amplification reactions, e.g., a PCR technique described above, to selectively enrich sequences. In one embodiment, the oligonucleotides or oligonucleotide pairs can be provided in a kit. A set of oligonucleotides can be generated wherein each oligonucleotide has a similar thermal profile (e.g., $T_m$). A set of oligonucleotides can comprise at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 oligonucleotide pairs. An oligonucleotide pair can be a pair of oligonucleotides that can hybridize to and amplify a sequence in a PCR. Each of the pairs of oligonucleotides can comprise sequence identical to sequence in all the other oligonucleotide pairs and sequence unique to that individual oligonucleotide pair.

In another aspect, a kit comprising a set of oligonucleotides that selectively hybridize and/or used to amplify one or more regions of a chromosome is provided, wherein each of said regions is sequenced at a rate of greater than 5-fold than other regions of the chromosome. The oligonucleotides can have the properties of the oligonucleotides described above.

Selecting Sequences Based on "Chromosome Walk"

In another embodiment, the selective enriching of non-random polynucleotide sequences can comprise identifying for enrichment and/or enriching at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 polynucleotide sequences from one or more regions of a first chromosome. The length of a region can be at least, or up to, 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000, or 10,000 kb. The number of regions from which sequences can be enriched can be at least 1, 2, 3, 4, 5, 6, 7, 8, 9, or 10. The selection of polynucleotide sequences to be enriched can be independent of the rate at which polynucleotides are sequenced in other samples. The polynucleotide sequences to be enriched can be clustered in a region, wherein the cluster can comprise about 1000-8000 bp, 1000-7000 bp, 1000-6000 bp, 1000-5000 bp, 1000-4000 bp, 1000-3000 bp, 1000-2000 bp, 4000-8000 bp, 5000-8000 bp, 6000-8000 bp, or 7000-8000 bp. There can be at least 1, 2, 3, 4, 5, 6, 7, 8, 9, or 10 clusters per region (e.g., per 50 kb region). The regions can be selected based on knowledge of a role for the region in a disease, for example, Down syndrome. Some polynucleotide sequences selected using this technique can be enriched (e.g., amplified) in practice, whereas some of the polynucleotide sequences selected using this technique may not be enriched (e.g., amplified) in practice. The polynucleotide sequences that are enriched using this identification technique can be used for subsequent enumeration and aneuploidy detection.

Oligonucleotide (primers) can be designed that hybridize specifically to polynucleotide sequences within a region (e.g., 50 kb). The oligonucleotide (primer) design can be automated to select sequences within a region (e.g., 50 kb) for enrichment using assembled chromosome sequence as a template for design. No prior knowledge of the level of sequenced polynucleotide sequences in other samples (e.g., in a database sequence information) is necessary to select the sequences for enrichment. PRIMER-BLAST (from NCBI open/public software) can be used to design oligonucleotides that specifically hybridize to sequences on one chromosome. The oligonucleotides can be designed to avoid hybridizing with sequences that contains one or more polymorphisms, e.g., a single nucleotide polymorphism (SNP). One or more oligonucleotide pairs can be generated to hybridize specifically to one or more polynucleotide sequences; the oligonucleotide pairs can be used in amplification reactions, e.g., using a PCR technique described above. A set of oligonucleotides can be generated wherein each oligonucleotide has a similar thermal profile (e.g., $T_m$). The set of oligonucleotides can comprise at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 oligonucleotide pairs. In one embodiment, a kit is provided comprising oligonucleotide pairs that can hybridize to specific polynucleotide sequences within a region (e.g., 50 kb). Each of the pairs of oligonucleotides can comprises sequence identical to sequence in all the other oligonucleotide pairs and sequence unique to that individual oligonucleotide pair.

Samples

The sample from which the non-random polynucleotide sequences are to be selectively enriched can be a maternal sample. Maternal samples that can be used in the methods of the provided invention include, for example, whole blood, serum, plasma, sweat, tears, ear flow, sputum, lymph, bone marrow suspension, lymph, urine, saliva, semen, sweat, vaginal flow, feces, transcervical lavage, cerebrospinal fluid, brain fluid, ascites, milk, or secretions of the respiratory, intestinal and genitourinary tracts. A sample can be from a processed blood sample, for example, a buffy coat sample. A buffy coat sample is an anticoagulated blood sample that forms after density gradient centrifugation of whole blood. A buffy coat sample contains, e.g., maternal nucleated cells, e.g., peripheral blood mononuclear cells (PBMCs). In one embodiment, a sample comprises fetal cells (e.g., fetal nucleated red blood cells (fnRBCs) or trophoblasts) and maternal cells.

A cell-free nucleic acid (e.g., DNA or RNA) sample can be a maternal sample, for example, serum or plasma. Methods for generating serum or plasma and methods for extracting nucleic acids are known in the art. A cell-free sample can comprise fetal and maternal cell-free nucleic acid, for example, DNA or RNA. A cell-free DNA sample can be from a plurality of different subjects. Samples used for generation of a database of sequenced polynucleotides can be cell-free nucleic acid samples.

Sequencing Methods

Applicable nucleic acid sequencing methods that can be used in the methods of the provided invention include, e.g., multi-parallel sequencing, massively parallel sequencing, sequencing-by-synthesis, ultra-deep sequencing, shot-gun sequencing, and Sanger sequencing, e.g., using labeled terminators or primers and gel separation in slab or capillary. These sequencing methods have been described previously. For example, a description of shotgun sequencing can be found in Fan et al. (2008) *PNAS* 105:16266-16271. Sanger sequencing methods are described in Sambrook et al., (2001) Molecular Cloning, Third Edition, Cold Spring Harbor Laboratory Press. Other DNA sequencing techniques can include sequencing-by-synthesis using reversibly terminated labeled nucleotides, pyrosequencing, 454 sequencing, allele specific hybridization to a library of labeled oligonucleotide probes, sequencing by synthesis using allele specific hybridization to a library of labeled clones followed by ligation, real time monitoring of the incorporation of labeled nucleotides during a polymerization step, polony sequencing, and SOLiD sequencing.

Sequencing methods are described in more detail below. A sequencing technology that can be used in the methods of the provided invention is SOLEXA sequencing (Illumina). SOLEXA sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another sequencing technique that can be used in the methods of the provided invention includes, for example, Helicos True Single Molecule Sequencing (tSMS) (Harris T. D. et al. (2008) *Science* 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step.

Another example of a DNA sequencing technique that can be used in the methods of the provided invention is 454 sequencing (Roche; Margulies, M. et al. (2005) *Nature* 437:376-380). 454 sequencing involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated.

Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide.

The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a sequencing technology that can be used in the methods of the provided invention includes the single molecule, real-time (SMRT™) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni G V and Meller A. (2007) *Clin Chem* 53:1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (e.g., as described in U.S. Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

The sequencing technique used in the methods of the provided invention can generate at least 1000 reads per run, at least 10,000 reads per run, at least 100,000 reads per run, at least 500,000 reads per run, or at least 1,000,000 reads per run.

The sequencing technique used in the methods of the provided invention can generate about 30 bp, about 40 bp, about 50 bp, about 60 bp, about 70 bp, about 80 bp, about 90 bp, about 100 bp, about 110, about 120 bp per read, about 150 bp, about 200 bp, about 250 bp, about 300 bp, about 350 bp, about 400 bp, about 450 bp, about 500 bp, about 550 bp, or about 600 bp per read.

The sequencing technique used in the methods of the provided invention can generate at least 30, 40, 50, 60, 70, 80, 90, 100, 110, 120, 150, 200, 250, 300, 350, 400, 450, 500, 550, or 600 bp per read.

In another aspect, a method for sequencing cell-free DNA from a maternal sample is provided comprising obtaining a maternal sample comprising cell-free DNA, enriching sequences that are representative of one or more 50 kb regions of a chromosome, or enriching sequences that are sequenced at a rate of at least 2-fold greater than other sequences, using an Illumina sequencer (e.g., Illumina Genome Analyzer IIx) and sequencing said enriched sequences of cell-free DNA.

Aneuploidy

The non-random sequences to be selectively enriched can include those on a chromosome suspected of being aneuploid in a fetus and/or on a chromosome suspected of being euploid in a fetus. Polynucleotide sequences from chromosome 1, 2, 3, 4, 5, 6, 7, 8, 9, 10, 11, 12, 13, 14, 15, 16, 17, 18, 19, 20, 21, 22, X, or Y can be selectively enriched. Chromosomes suspected of being aneuploid in a fetus can include chromosome 1, 2, 3, 4, 5, 6, 7, 8, 9, 10, 11, 12, 13, 14, 15, 16, 17, 18, 19, 20, 21, 22, X, or Y. Chromosomes suspected of being euploid in a fetus can include chromosome 1, 2, 3, 4, 5, 6, 7, 8, 9, 10, 11, 12, 13, 14, 15, 16, 17, 18, 19, 20, 21, 22, X, or Y.

The methods of the provided invention can be used to detect aneuploidy. Aneuploidy is a state where there is an abnormal number of chromosome(s), or parts of a chromosome. Aneuploidy can include, for example, monosomy, partial monosomy, trisomy, partial trisomy, tetrasomy, and pentasomy. Examples of aneuploidy that can be detected include Angelman syndrome (15q11.2-q13), cri-du-chat syndrome (5p-), DiGeorge syndrome and Velo-cardiofacial syndrome (22q11.2), Miller-Dieker syndrome (17 p13.3), Prader-Willi syndrome (15q11.2-q13), retinoblastoma (13q14), Smith-Magenis syndrome (17 p11.2), trisomy 13 (Patau syndrome), trisomy 16, trisomy 18 (Edward syndrome), trisomy 21 (Down syndrome), triploidy, Williams syndrome (7q 11.23), and Wolf-Hirschhom syndrome (4p-). Examples of sex chromosome abnormalities that can be detected by methods described herein include, but are not limited to, Kallman syndrome (Xp22.3), steroid sulfate deficiency (STS) (Xp22.3), X-linked ichthyosis (Xp22.3), Klinefelter syndrome (XXY), fragile X syndrome, Turner syndrome, metafemales or trisomy X (XXX syndrome, 47,XXX aneuploidy), and monosomy X.

In addition, the enrichment methods can also be used to detect locus- and allele-specific sequences of interest, for example, autosomal and sex chromosomal point mutations, deletions, insertions, and translocations, which can be associated disease. Examples of translocations associated with disease include, for example, t(9;22)(q34;q11)—Philadelphia chromosome, CML, ALL; t(2;5)(p23;q35) (anaplastic large cell lymphoma); t(8;14)—Burkitt's lymphoma (c-myc); t(8;21)(q22;q22)—acute myeloblastic leukemia with maturation (AML1-ETO); t(12;21)(p12;q22)—ALL (TEL-AML1); t(12;15)(p13;q25)—(TEL-TrkC); t(9;12) (p24;p13)—CML, ALL (TEL-JAK2); acute myeloid leukemia, congenital fibrosarcoma, secretory breast carcinoma; t(11;14)—Mantle cell lymphoma (cyclin D1); t(11;22)(q24; q11.2-12)—Ewing's sarcoma; t(14;18)(q32;q21)—Follicular lymphoma (Bcl-2); t(15;17)—Acute promyelocytic leukemia; t(1;12)(q21;p13)—Acute myelogenous leukemia; t(17;22)—DFSP; and t(X;18)(p11.2;q11.2)—Synovial sarcoma.

Methods for determining fetal aneuploidy using random sequencing techniques are described, for example, in U.S. Patent Application Publication Nos. 20090029377 and 20090087847, Fan H C et al. (2008) *PNAS* 105:16266-71, and U.S. Provisional Patent Application Nos. 61/296,358 and 61/296,464, which are herein incorporated by reference in their entireties. The methods of fetal aneuploidy determination can be based on the fraction of fetal DNA in a sample. Such methods are described, for example, in U.S. Provisional Patent Application No. 61/296,358.

Aneuploidy can be suspected or determined when the number of enumerated sequences is greater than a predetermined amount. The predetermined amount can be based on estimated amount of DNA in a cell-free DNA sample. The predetermined amount can be based on the amount of enumerated sequences from a control region.

Library Formation

In another aspect, a method is provided for generating a library of selectively enriched non-random polynucleotide sequences comprising a) amplifying one or more polynucleotide sequences with a first set of oligonucleotide pairs, b) amplifying the product of a) with a second set of oligonucleotides pairs; and c) amplifying the product of b) with a third set of oligonucleotide pairs.

The polynucleotide sequences can be those enriched by the methods of the provided invention. The first set of oligonucleotide pairs can comprise sequence that distinguishes polynucleotides in one sample from polynucleotides in another sample. The first set of oligonucleotide pairs can comprise sequence that distinguishes polynucleotides in one sample from polynucleotides in another sample and sequence that extends the length of the product. Bridge amplification in Illumina (SOLEXA) sequencing can be most effective when the sequences are 100-500 bp. Fetal nucleic acid sequences are often less than 250 bp, and sequences of less than 100 bp can be amplified from cell-free samples. Thus, the sequence that extends the length of the product can facilitate SOLEXA sequencing. The polynucleotide sequences can be sequences enriched using the methods described herein.

In another aspect, a method for labeling enriched polynucleotides in two or more samples that allows identification of which sample the polynucleotide originated is provided, comprising: a) amplifying one or more polynucleotide sequences in two or more samples with a first set of oligonucleotide pairs, wherein the first set of oligonucleotide pairs comprises sequence that distinguishes polynucleotides from one sample from polynucleotides in another sample, b) amplifying the product of a) with a second set of oligonucleotides pairs; and c) amplifying the product of b) with a third set of oligonucleotide pairs.

In another aspect, a kit is provided comprising a) a first set of oligonucleotide primer pairs comprising: sequence that selectively hybridizes to a first set of genomic DNA sequences and sequence in-common amongst each of the first set of oligonucleotide primer pairs, b) a second set of oligonucleotide primer pairs with sequence that selectively hybridizes to the common sequence of the first set of oligonucleotide primer pairs and sequence common to the second set of oligonucleotide pairs, and c) a third set of oligonucleotide primer pairs with sequence that selectively hybridizes to the common sequence of the second set of oligonucleotide pairs.

The first set of primers can comprise sequence that distinguishes polynucleotides in one sample from polynucleotides in another sample.

The common region in the first set of primers can comprise sequence that distinguishes polynucleotides in one sample from polynucleotides in another sample and that extends the length of the product.

In another aspect, a kit is provided comprising: a first set of primer pairs that selectively amplifies a set of genomic sequences to create a first set of amplification products, a second set of primer pair that selectively amplifies the first set of amplification products, and a third set of primer pairs that selectively amplifies the second set of amplification products.

EXAMPLES

Example 1: "Hot Spot" Amplification Strategy

FIG. 1 illustrates a strategy for selecting sequences from chromosome 21 for enrichment. In step 100, sequence run data was combined. Total chromosome 21 sequence reads were used (102). These samples can include reads from samples that contain trisomy 21. "Hot" and "cold" regions of sequence coverage were mapped on chromosome 21 (104). For example, the region examined can be within a 5.8 Mb Down syndrome critical region (DSCR). PCR primers are designed, which can anneal to intergenic DNA or intragenic DNA (106). The primers were designed to anneal specifically with chromosome 21. The regions to be amplified can be a hot spot region, or region to which a number of sequence reads map (108). The PCR fragments generated can be approximately 200 bp in length. Next, sequencing analysis is performed using BioAnalyzer analysis and/or PCR/probe analysis (110).

Figure 2:
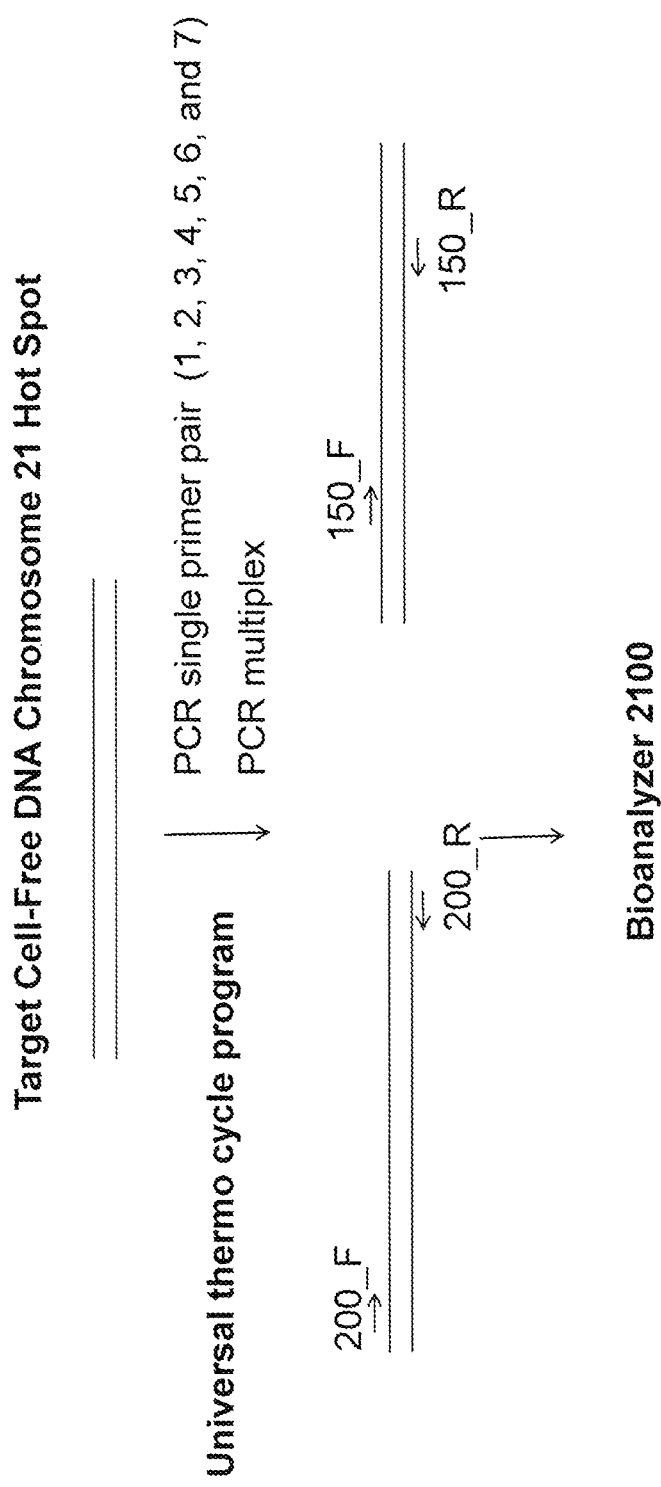
FIG. 2 illustrates a PCR scheme for "hot spot" enrichment.
Figure 4A:
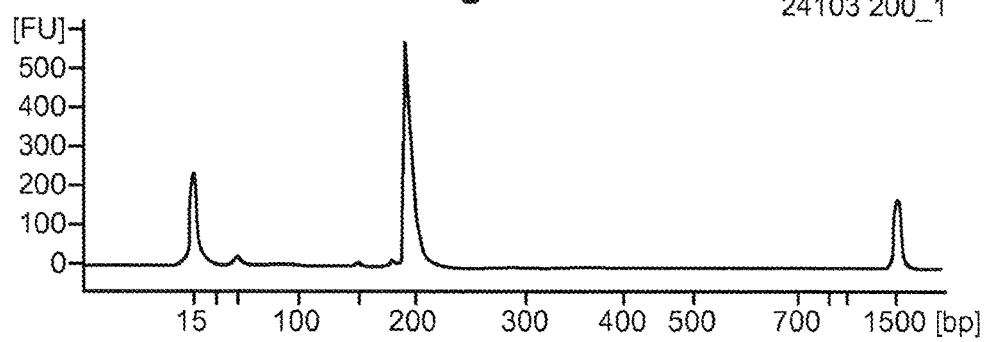
Figure 4B:
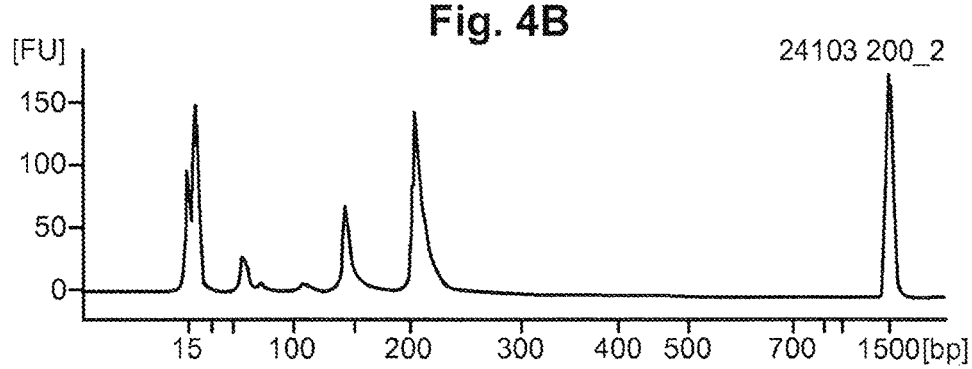
Figure 4C:
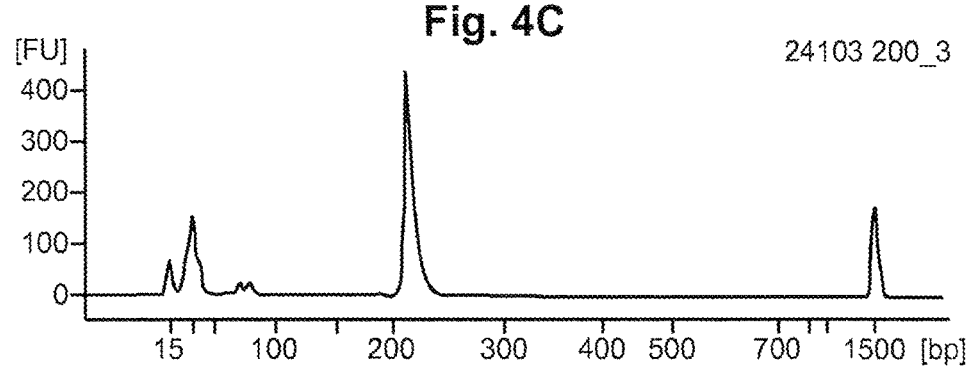
Figure 4D:
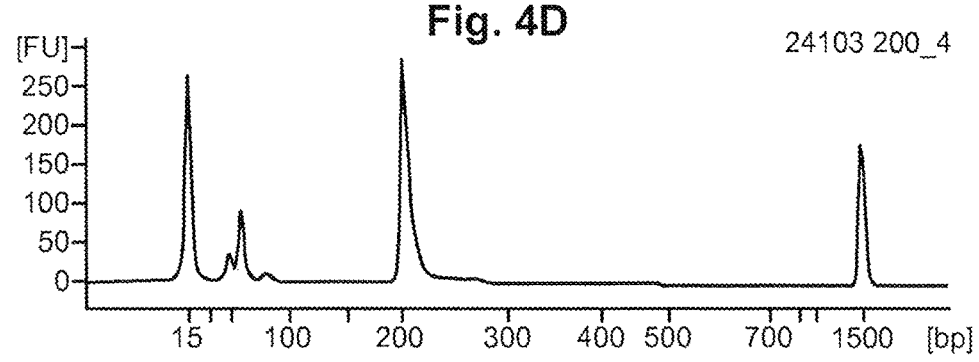
Figure 4E:
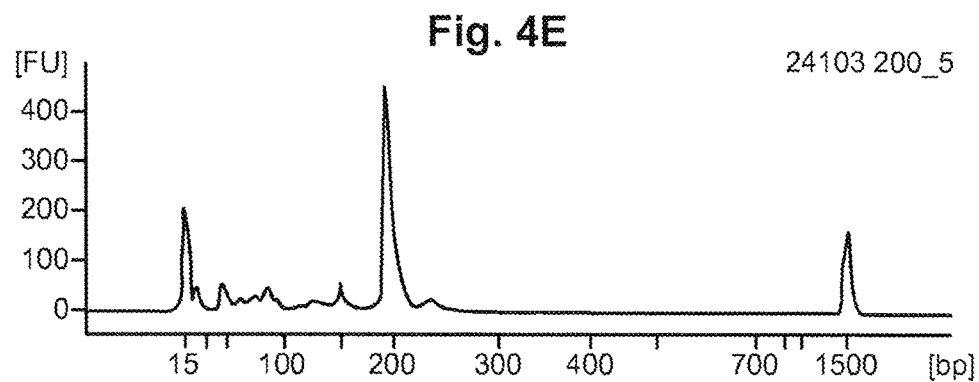
Figure 4F:
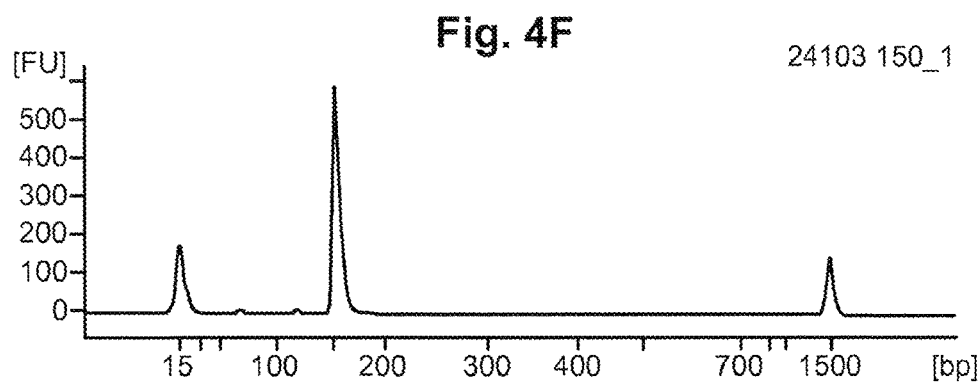
Figure 4G:
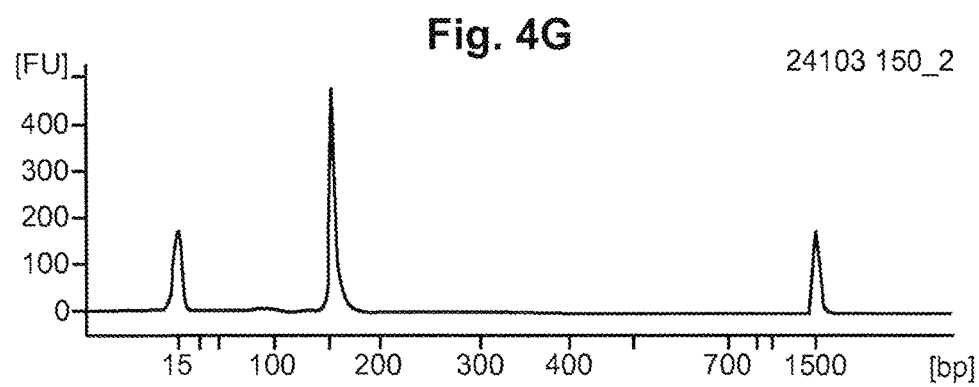
Figure 4H:
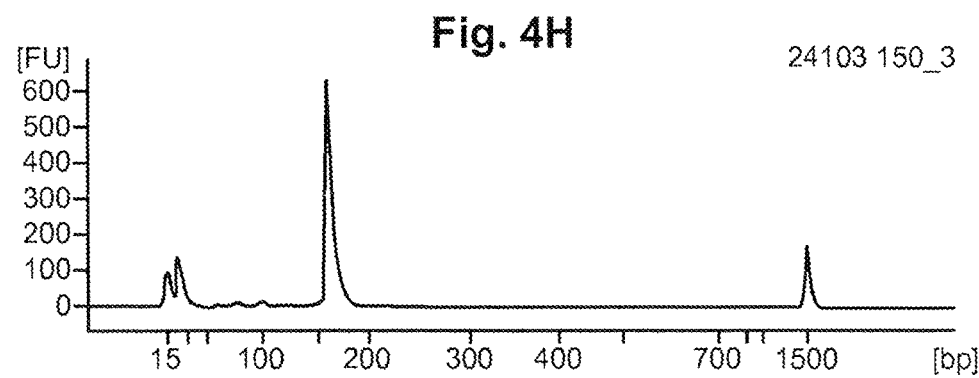
Figure 4I:
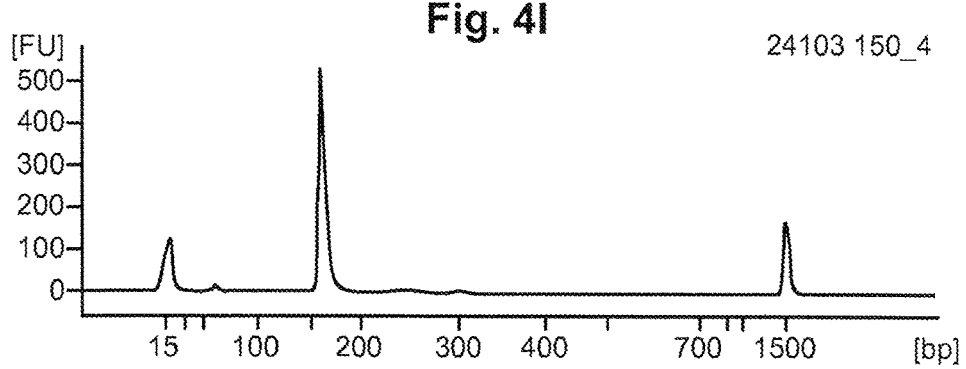
Figure 4J:
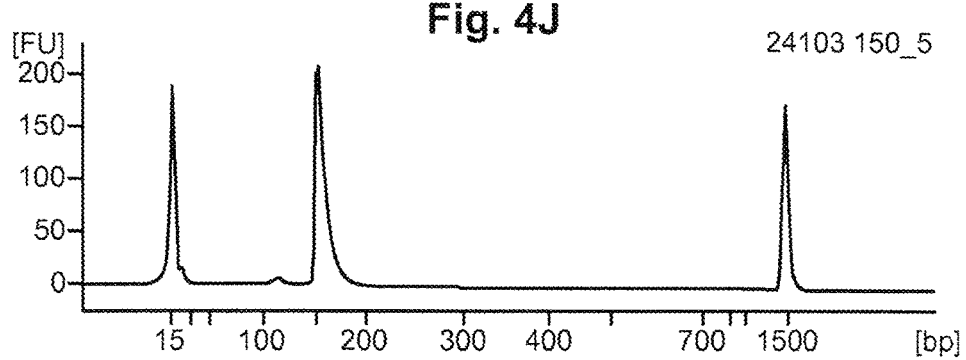
Figure 4K:
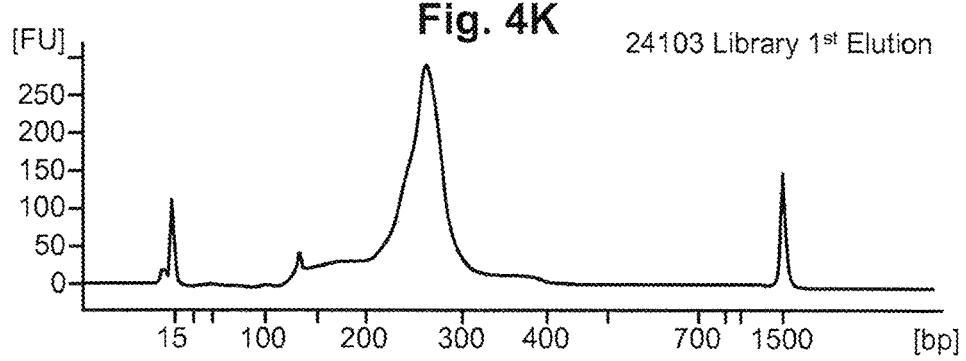
Figure 4L:
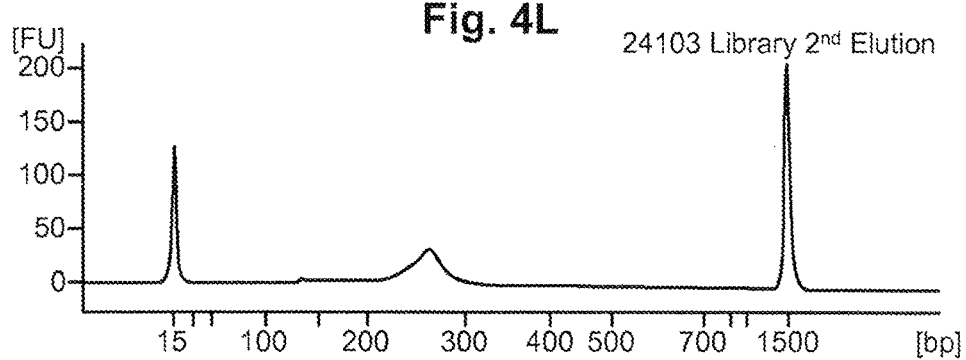
Figure 6I:
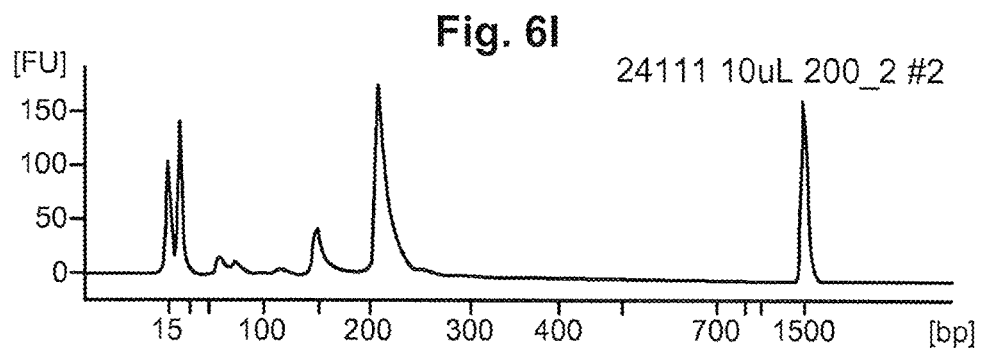
Figure 6J:
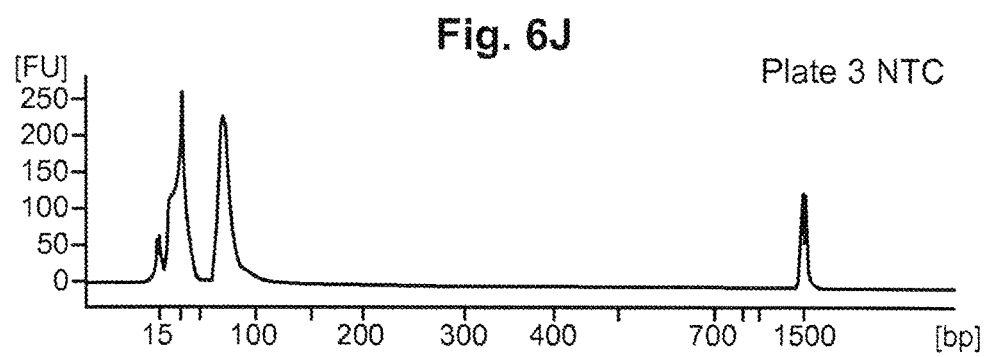
Figure 6K:
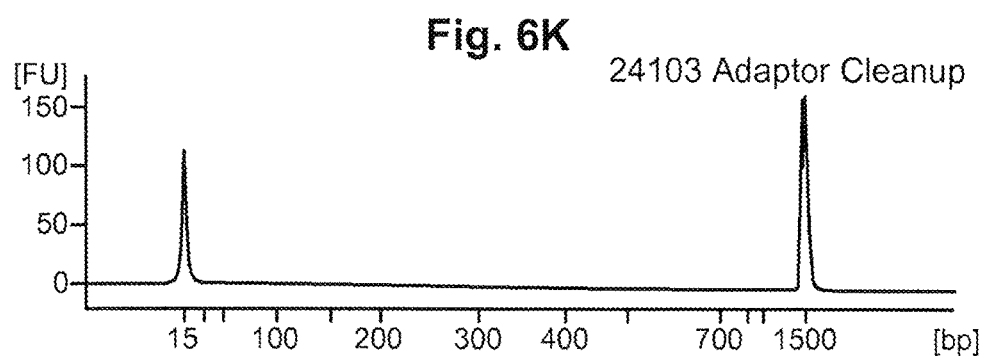
Figure 6L:
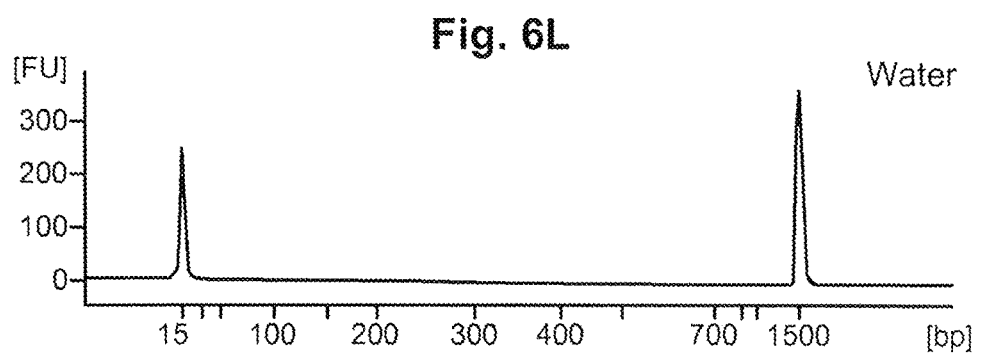

PCR primers were designed to generate amplicons of approximately 200 bp and 150 bp from cell-free DNA template, as depicted is shown in FIG. 2. PCR amplification was performed using both simplex and multiplex reactions. The size of the amplicons was analyzed by Agilent 2100 Bioanalyzer and DNA 1000 kit. Sequences for primer pairs 1_150, 2_150, 3_150, 4_150, 5_150, 6_150, and 7_150 regions amplification, used in generating the data in FIGS. 2, 3, 4, and 5, are shown in Table 1.

Primer sequences for 1_200, 2_200, 3_200, 4_200, 5_200, and 6_200 regions amplification, for FIGS. 2, 4, and 6, are illustrated in Table 2.

TABLE 1

Sequences for primer pairs 1_150, 2_150, 3_150, 4_150, 5_150, 6_150, and 7_150 (SEQ ID NOS 1-14, respectively, in order of appearance).

| Chromosome Location | Primer Name | Primer Sequence | PCR Size (bp) |
| --- | --- | --- | --- |
| (1) Chr21: 45, 651, 908-45, 652, 158 | 1_150_45652158_F<br>1_150_45652158_R | CCCCAAGAGGTGCTTGTAGT<br>GCCATGGTGGAGTGTAGGAG | 155 |
| (2) Chr21: 46, 153, 568-46, 153, 825 | 2_150_46153825_F<br>2_150_46153825_R | CTGAAGTGCTGCCAACACAC<br>TGATCTTGGAGCCTCCTTTG | 153 |
| (3) Ch21: 46, 048, 091-46, 048, 339 | 3_150_46, 048, 339_F<br>3_150_46, 048, 339_R | AGCTTCTCCAGGACCCAGAT<br>CATTCATGGGAAGGGACTCA | 151 |
| (4) Chr21: 46, 013, 033-46, 013, 258 | 4_150_46, 013, 258_F<br>4_150_46, 013, 258_R | CCATTGCACTGGTGTGCTT<br>GAGACGAGGGGACGATAGC | 155 |
| (5) Chr21: 40, 372, 444-40, 372, 655 | 5_150_40, 372, 655_F<br>5_150_40, 372, 655_R | TGCCATCGTAGTTCAGCGTA<br>TTGGACCACAGCTCAGAGG | 152 |
| (6) Chr21: 41, 470, 712-41, 470, 747 | 6_41, 470, 712-150_F<br>6_41, 470, 712-150_R | AAAGTGTGCTTGCTCCAAGG<br>GGCAAAACACAGCCCAATAG | 152 |
| (7) Chr21 | Ch21_APP150_F<br>Ch21_APP150_R | CCTAGTGCGGGAAAAGACAC<br>TTCTCTCCCTTGCTCATTGC | 145 |

TABLE 2

Sequences for primer pairs 1_200, 2_200, 3_200, 4_200, 5_200, and 6_200 (SEQ ID NOS 15-26, respectively, in order of appearance).

| Chromosome Location | Primer Name | Primer Sequence | PCR Size (bp) |
| --- | --- | --- | --- |
| (1) Chr21: 45, 651, 908-45, 652, 158 | 1_45651908-45652158_F<br>1_45651908-45652158_R | GAGTCAGAGTGGAGCTGAGGA<br>GGAGGTCCTAGTGGTGAGCA | 199 |

TABLE 2-continued

Sequences for primer pairs 1_200, 2_200, 3_200, 4_200, 5_200, and 6_200
(SEQ ID NOS 15-26, respectively, in order of appearance).

| Chromosome Location | Primer Name | Primer Sequence | PCR Size (bp) |
| --- | --- | --- | --- |
| (2) Chr21: 46, 153, 568-46, 153, 825 | 2_46153568-46153825_F<br>2_46153568-46153825_R | TGTGGGAAGTCAGGACACAC<br>GATCTTGGAGCCTCCTTTGC | 205 |
| (3) Chr21: 46, 048, 091-46, 048, 339 | 3_46, 048, 091-46, 048, 339_F<br>3_46, 048, 091-46, 048, 339_R | GTGACAGCCTGGAACATGG<br>CAAGGCACCTGCACTAAGGT | 203 |
| (4) Chr21: 46, 013, 033-46, 013, 258 | 4_46, 013, 033-46, 013, 258_F<br>4_46, 013, 033-46, 013, 258_R | TGCCTCCTGCTACTTTTACCC<br>AGACGGAACAGGCAGAGGT | 204 |
| (5) Chr21: 40, 372, 444-40, 372, 655 | 5_40372444-40372655_F<br>5_40372444-40372655_R | CAAGACACAAGCAGGAGAGC<br>CAGTTTGGACCACAGCTCAG | 196 |
| (6) Chr21: 41, 470, 710-41, 471, 028 | 6_41470710_200F<br>6_41470710-200R | AAAGTGTGCTTGCTCCAAGG<br>TGGAACAAGCCTCCATTTTC | 194 |

TABLE 3

Figure 7:
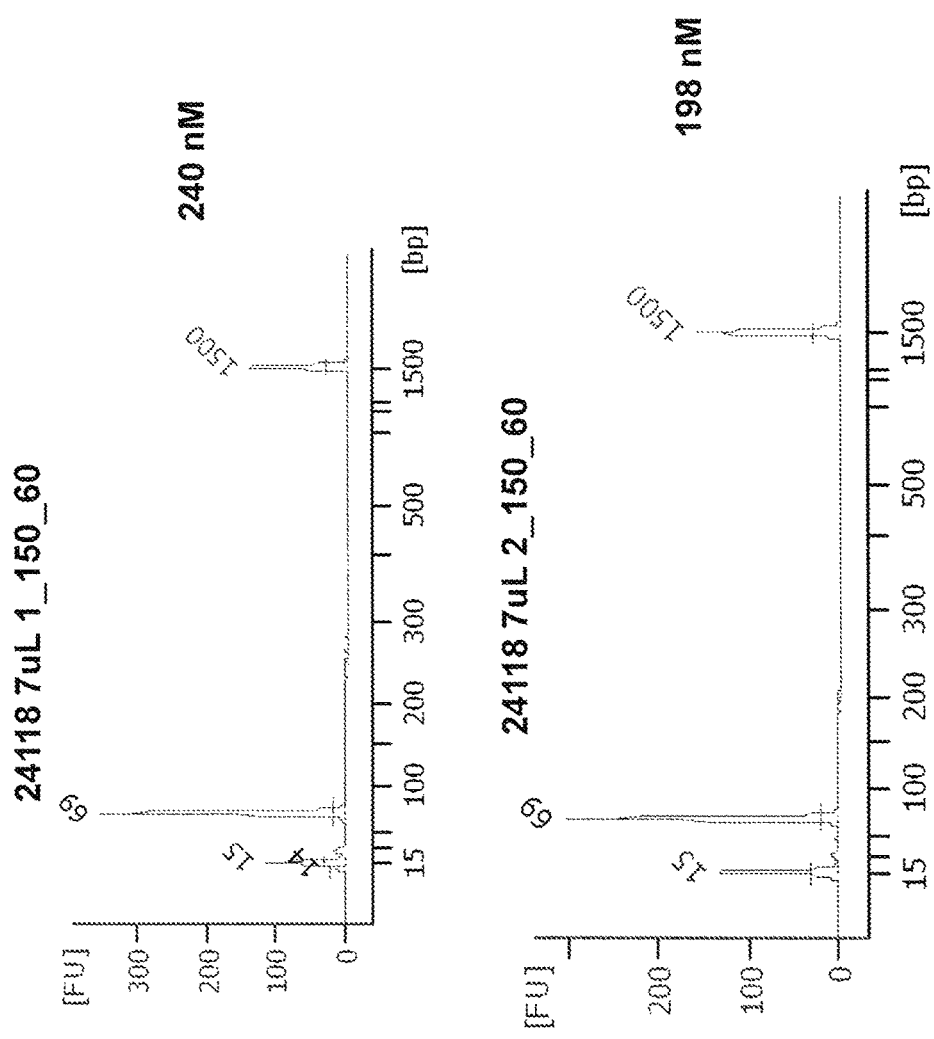
FIG. 7 illustrates PCR amplification of approximately 60 bp amplicons from chromosome 21.
Figure 8:
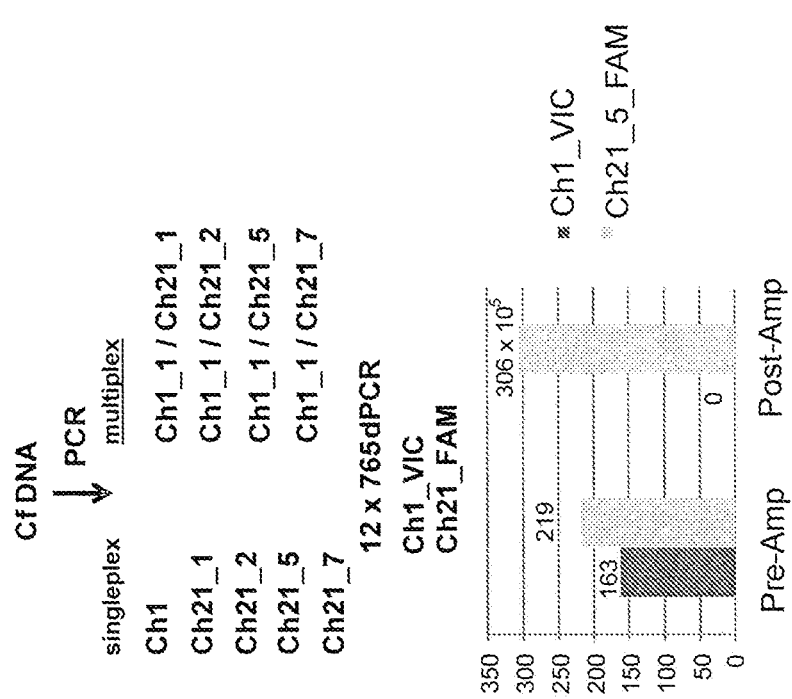
FIGS. 8A-8C illustrate Fluidigm digital PCR analysis evidence of chromosome 21 and 1 amplification.

Primer sequences for 1_150_60 and 2_150_60 region PCR amplification (FIG. 7);
same primer plus probe sequences for FIG. 8
(SEQ ID NOS 27-41, respectively, in order of appearance).

| Chromosome Location | Primer Name | Primer Sequence | PCR Size (bp) |
| --- | --- | --- | --- |
| (1) Chr21: 45, 651, 908-45, 652, 158 | 1_150_60_45652158_F<br>1_150_60_45652158_R<br>1_150_60_45652158_P | GAGGTGCTTGTAGTCAGTGCTTCA<br>CCCGGTGACACAGTCCTCTT<br>AGTCAGAGTGGAGCTGAG | 64 |
| (2) Chr21: 46, 153, 568-46, 153, 825 | 2_60_150_46153825_F<br>2_60_150_46153825_R<br>2_60_150_46153825_P | TGCTGCCAACACACGTGTCT<br>CAGGGCTGTTGCTCATGGA<br>TCCCCTAGGATATCATC | 60 |
| (5) Chr21: 40, 372, 444-40, 372, 655 | 5_60_150_40372655_F<br>5_60_150_40372655_R<br>5_60_150_40372655_P | CCCGCATCTGCAGCTCAT<br>TCTCTCCAAGTCCTACATCCTGTATG<br>CCAGGTGGCTTCC | 65 |
| Ch21 | 7_Amyloid_21_F<br>7_Amyloid_21_R<br>7_Amyloid_21_P | GGG AGC TGG TAC AGA AAT GAC TTC<br>TTG CTC ATT GCG CTG ACA A<br>AGC CAT CCT TCC CGG GCC TAG G | ref. 1 |
| Ch1 | ch1_1_F<br>ch1_1_R<br>ch1_1_P | GTTCGGCTTTCACCAGTCT<br>CTCCATAGCTCTCCCCACT<br>CGCCCTGCCATGTGGAA | ref. 1 |

Ref 1 in Table 3 refers to Fan H C et al. (2008) PNAS 105: 16266-16271, which is herein incorporated by reference in its entirety. FIG. 3 illustrates amounts of nucleic acids that were detected for different samples of cell-free plasma DNA using different primers. FIGS. 4A-M illustrate simplex PCR Amplification Bioanalyzer results, some of which correspond to the data in FIG. 3.

FIG. 5 illustrates results of PCR amplification of chromosome 21 in singleplex reactions. FIGS. 6A-M illustrate Bioanalyzer results for multiplex PCR amplifications of chromosome 21. FIG. 7 illustrates Bioanalyzer results for PCR amplifications of approximately 60 bp amplicons. Table 3. illustrates primer sequences for 1_150_60 and 2_150_60 region PCR amplification.

FIG. 8A illustrates enrichment of chromosome 1 and 21 sequence. Four different sequences from chromosome 21 were amplified, as well a region from chromosome 1. Numbers of molecules were counted by dPCR. The ratio of the different sequences of chromosome 21 to chromosome 1 sequences from samples that underwent enrichment was calculated. Also provided are the ratio of chromosome 21 to 1 sequences from non-enriched (cf plasma DNA) samples. Also, genomic DNA was extracted from a cultured T21 cell line (Down Syndrome in origin) as positive control to show that dPCR primer/probe can amplify the ch21. The T21 cell line was ordered from ATCC and cultured in the lab: ATCC number: CCL-54; Organism: Homo sapiens; Morphology: fibroblast; Disease: Down syndrome; Gender: male; Ethnicity: Caucasian.

Figure 8C:
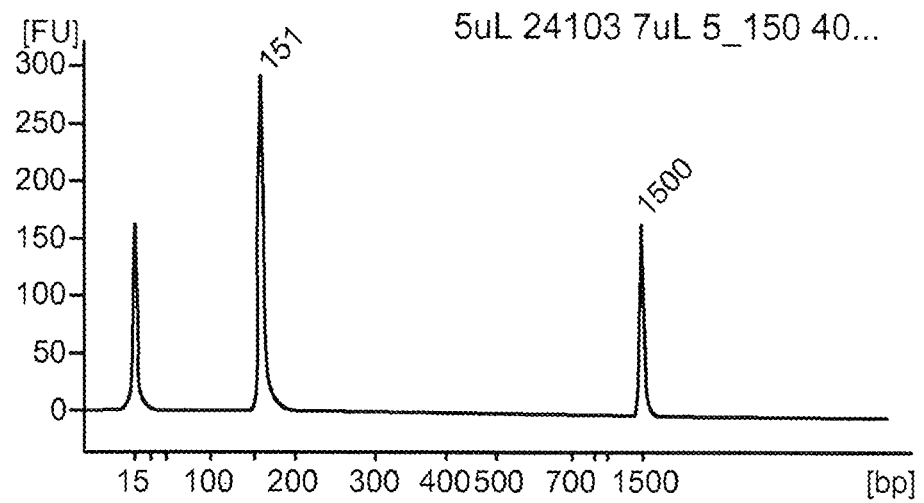

FIG. 8B illustrates a comparison of chromosome 1 and 21 counts pre-amplification (left side). Shown on the right side of the chart is the state following enrichment for ch21_5 using 560_150 primers (Table 3); amplified sequences were probed with chromosome 1-VIC and chromosome 21-FAM probes (Table 3). Only Ch21_5 sequence was amplified. FIG. 8C illustrates the size of an enriched fragment, ch21_5, using 560_150 primers (Table 3).

Figure 9:
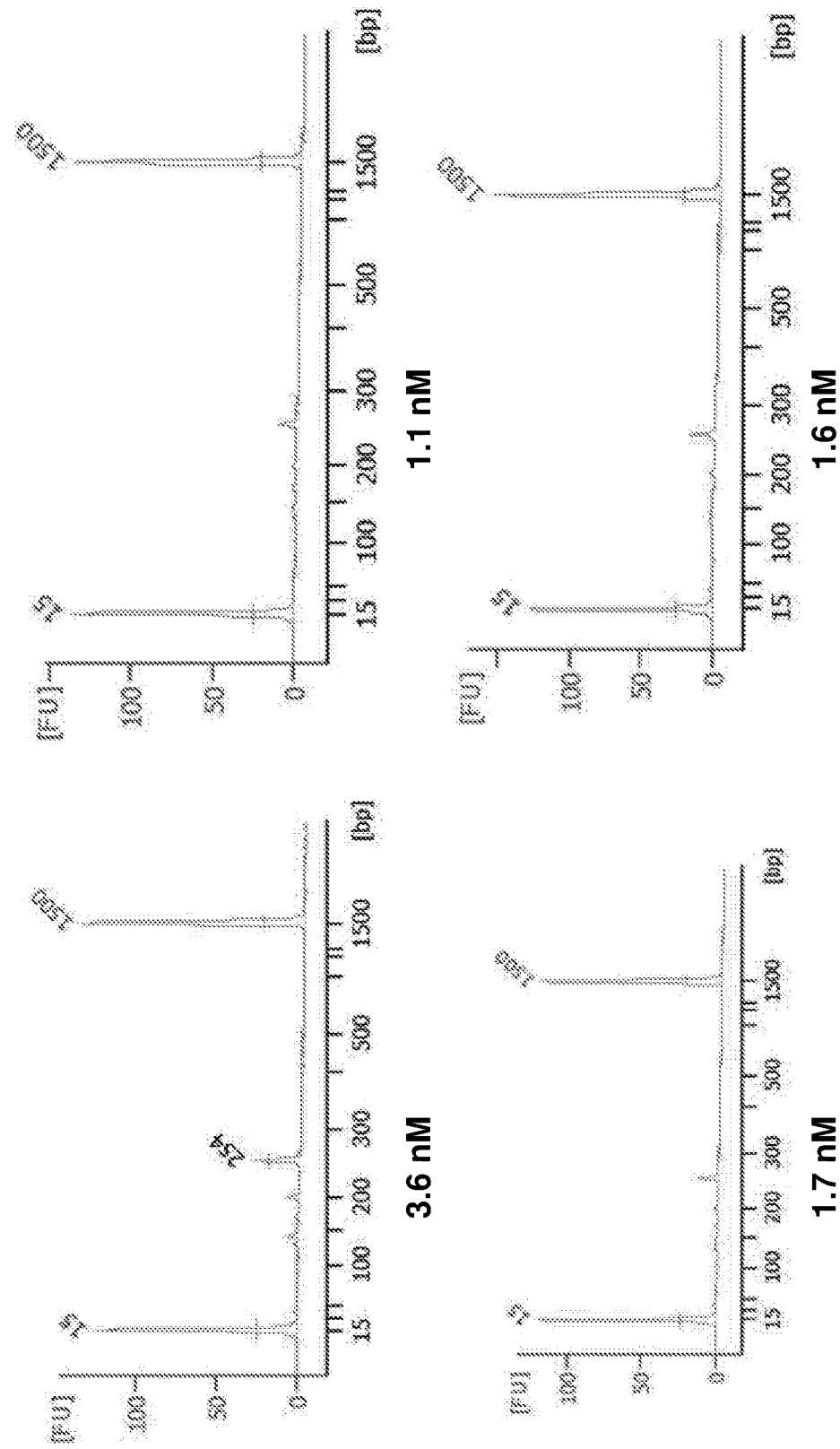
FIG. 9 illustrates size and concentration of DNA library construction conditions for PCR enrichment of chromosome 21 fragments in 4 different conditions.

A DNA library was generated with 24103_5_150 PCR fragment using Illumina ChIP-Seq Sample Preparation kit in 4 different conditions. The size and concentration of the generated DNA library was analyzed using Bioanalyzer shown in FIG. 9.

Figure 10:
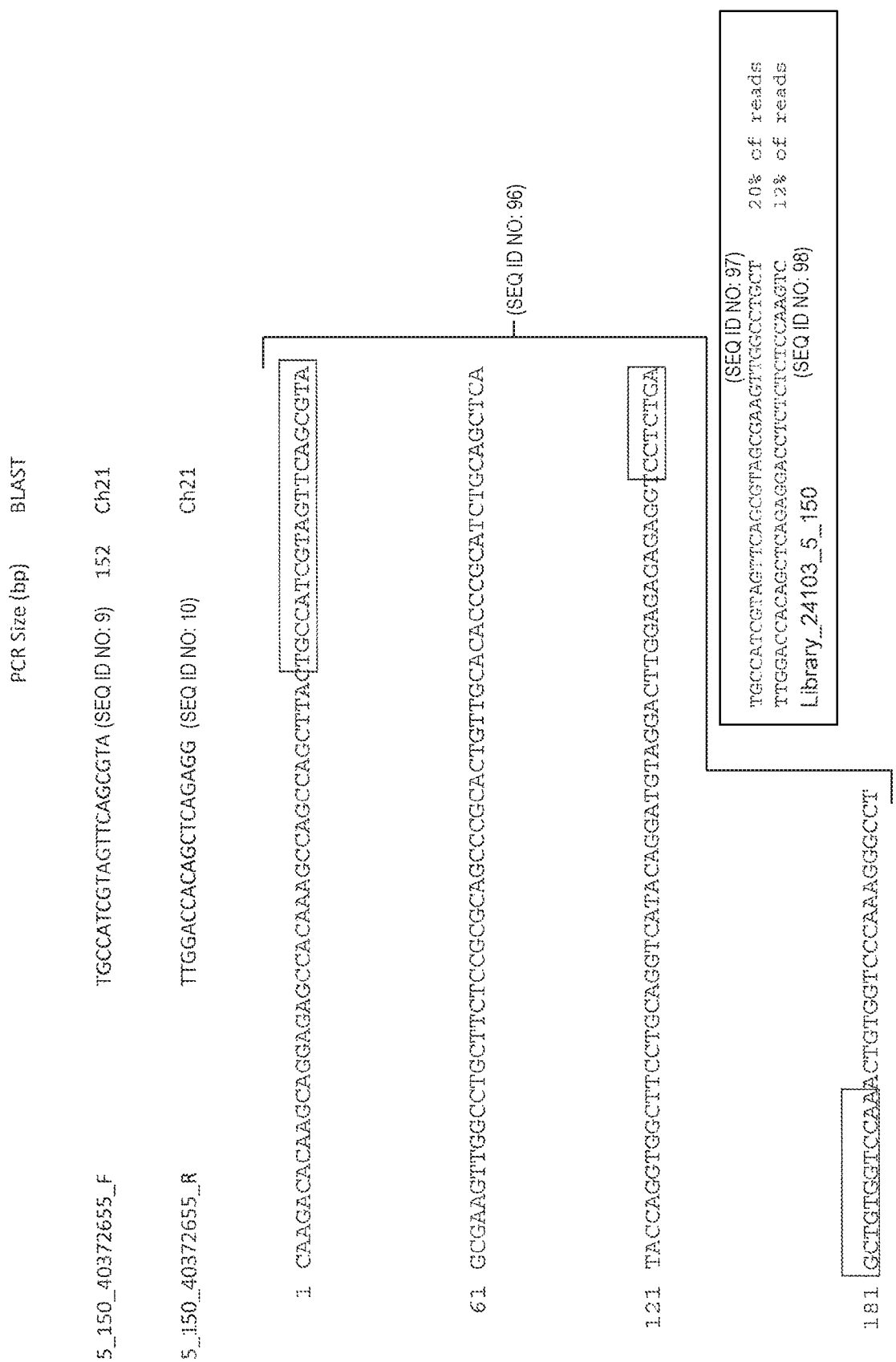
FIG. 10 illustrates Illumina GA sequencing analysis.

This DNA library was sequenced using an Illumina GA Sequencer and the sequences was analyzed with Illumina Pipeline software. The output sequencing reads were aligned to a human reference sequence. The correct and unique aligned sequences were then scored, of which 20% and 12% are exactly the same sequences of forward and reverse primer sequences and adjacent flanking sequences, respectively, as shown in the FIG. 10.

Example 2: Chromosome Walk Strategy for Sequence Enrichment

Figure 11:
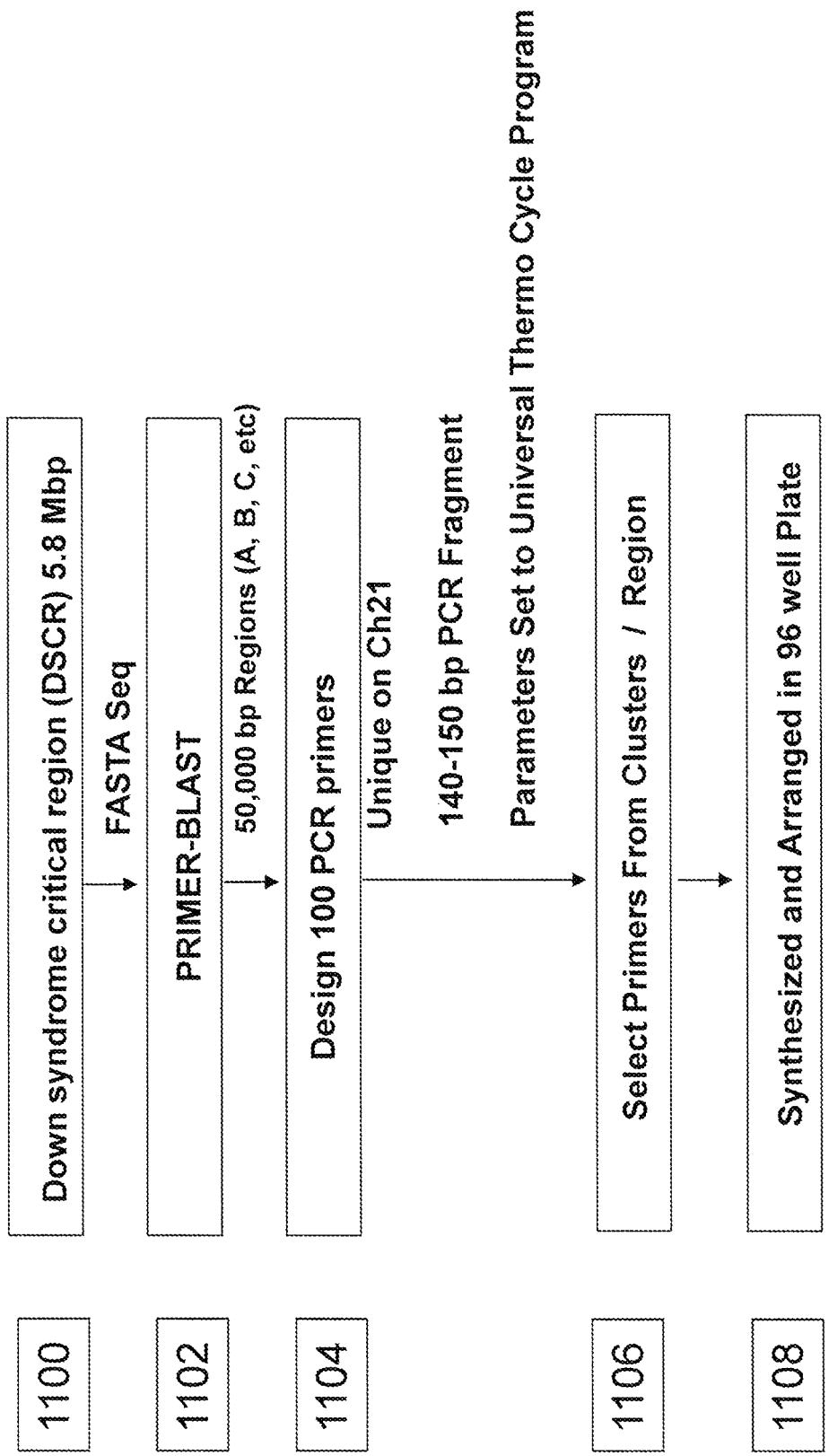
FIG. 11 illustrates strategy for design of PCR primers for the "chromosome walk" method of amplification.

FIG. 11 illustrates an overview of the chromosome walk strategy for sequence enrichment. A 5.8 Mbp Down syndrome critical region was selected (1100). PRIMER-BLAST (1102) was used to design 100 PCR primers (1104) in 50,000 bp regions. Unique sequences on chromosome 21 were sought to generate approximately 140-150 bp fragments. Primers were selected from different clusters in different regions on chromosome 21 (1106) and synthesized and arranged in 96 well plates (1108).

Figure 13:
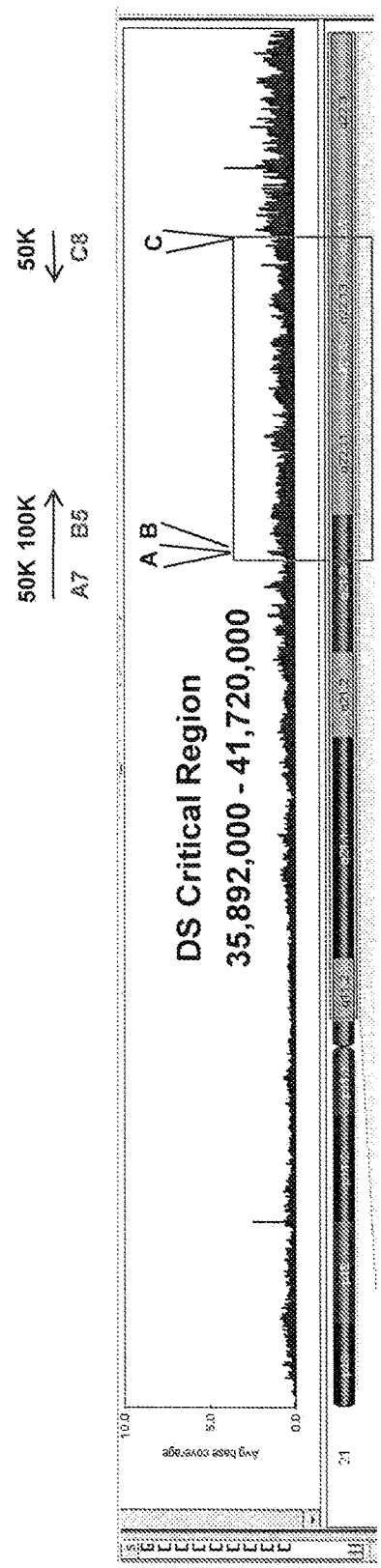
FIG. 13 illustrates relative position of regions A, B, C, and a Down syndrome critical region on a schematic of chromosome 21.
Figure 14A:
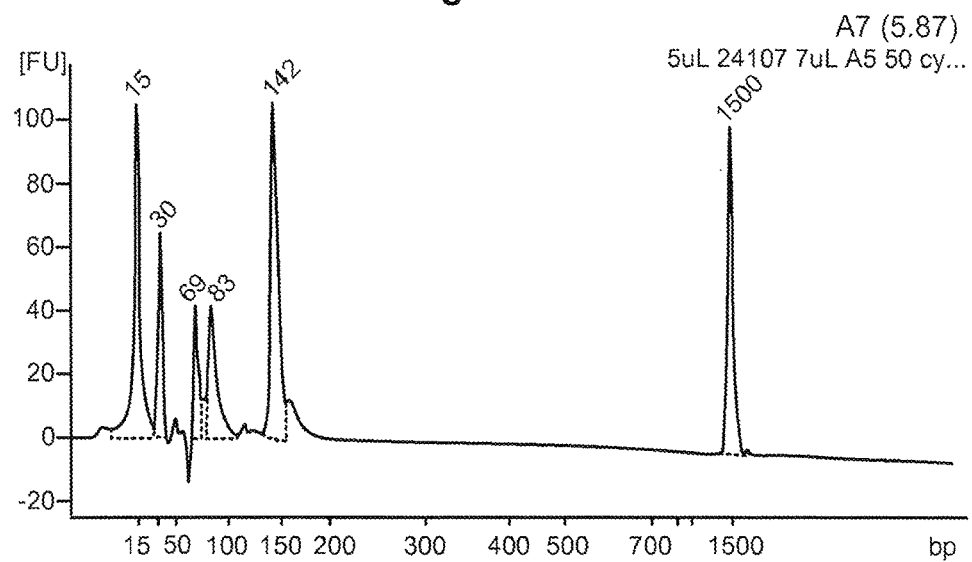
FIGS. 14A-D illustrate PCR amplification results using the "chromosome walk" method of sequence selection.
Figure 14B:
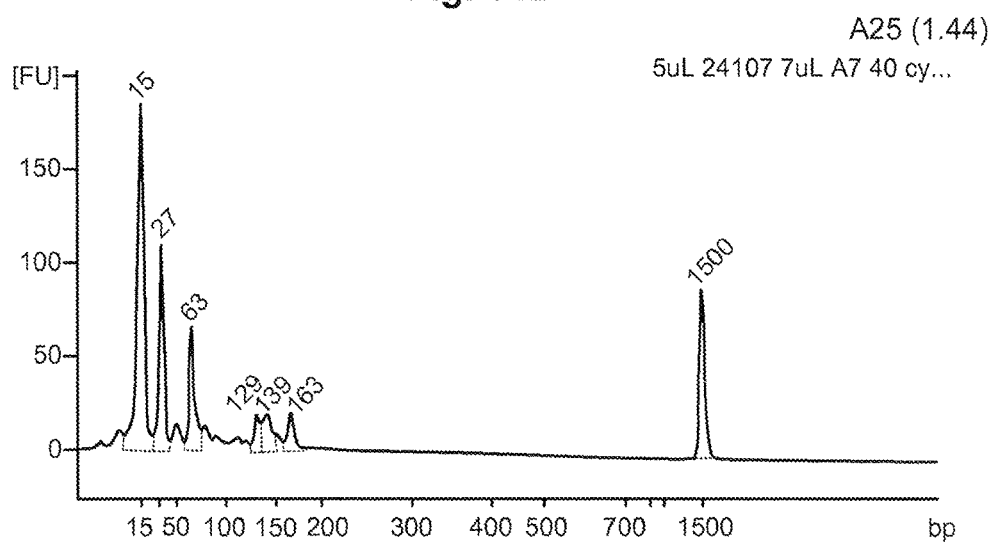
Figure 14C:
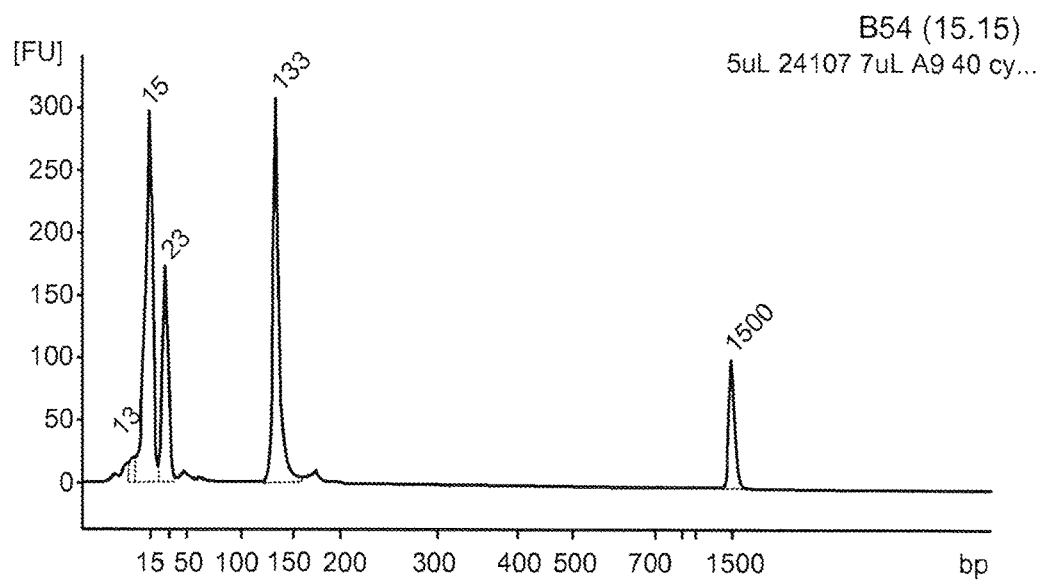
Figure 14D:
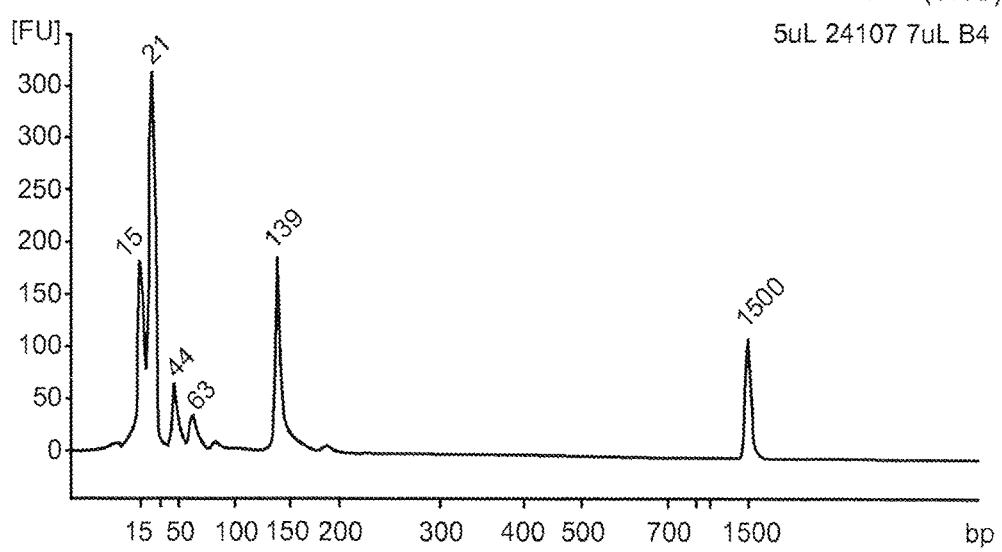
Figure 16A:
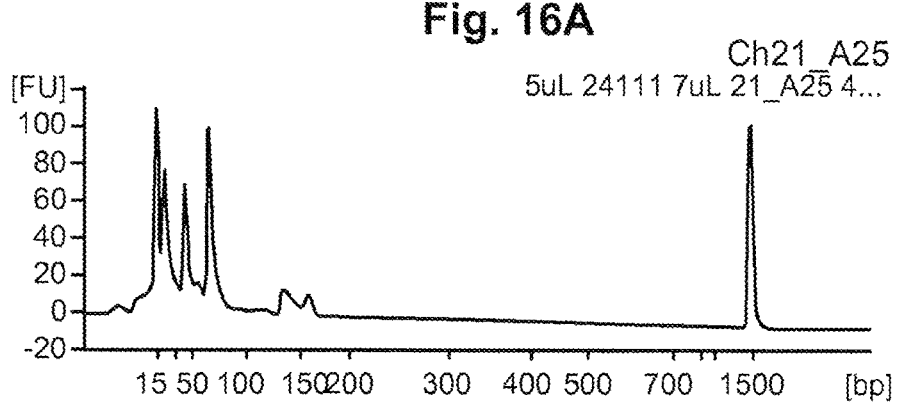
FIGS. 16A-M illustrate enrichment of chromosome 21 sequence and reference chromosome 1, 2, and 3 sequence.
Figure 16B:
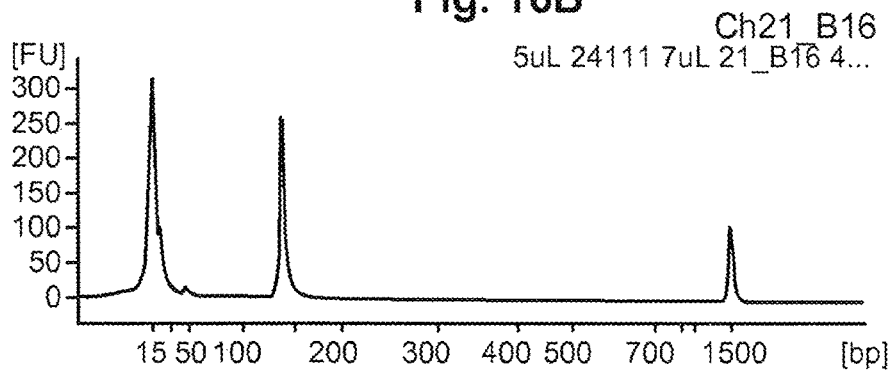
Figure 16C:
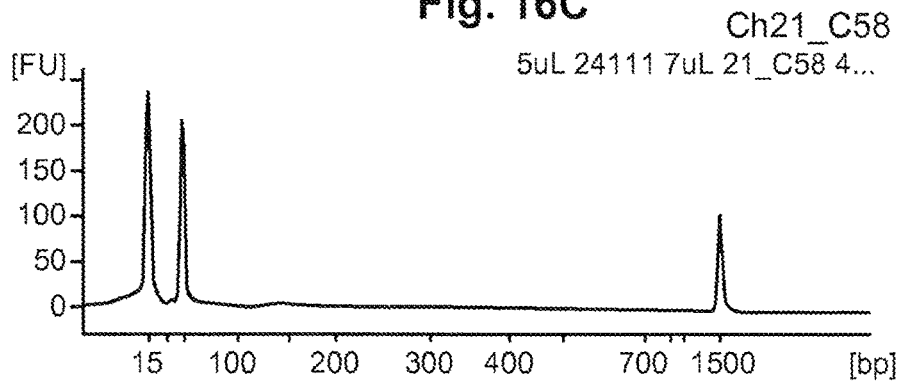
Figure 16D:
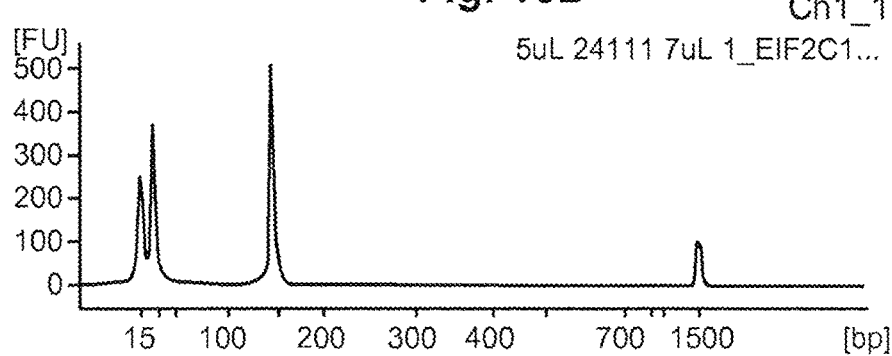
Figure 16E:
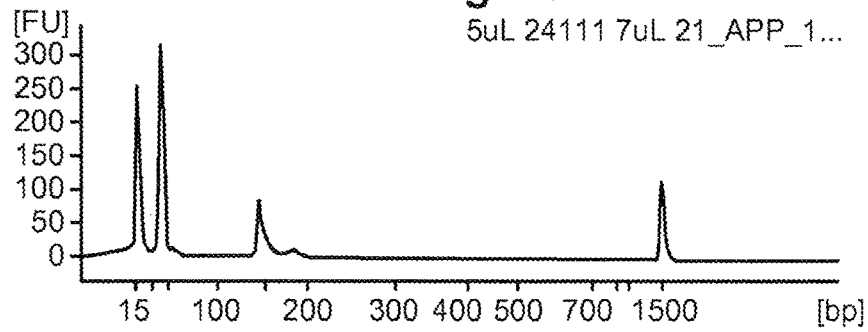
Figure 16F:
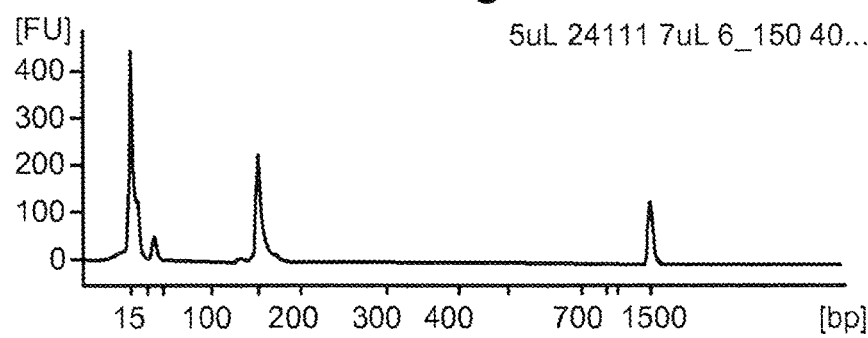
Figure 16G:
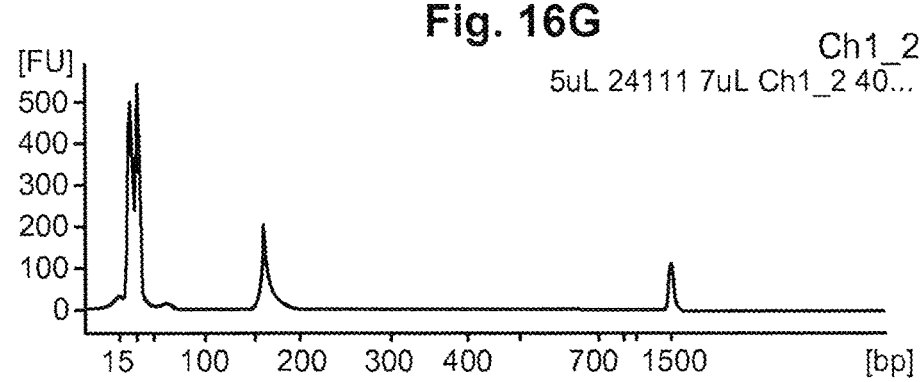
Figure 16H:
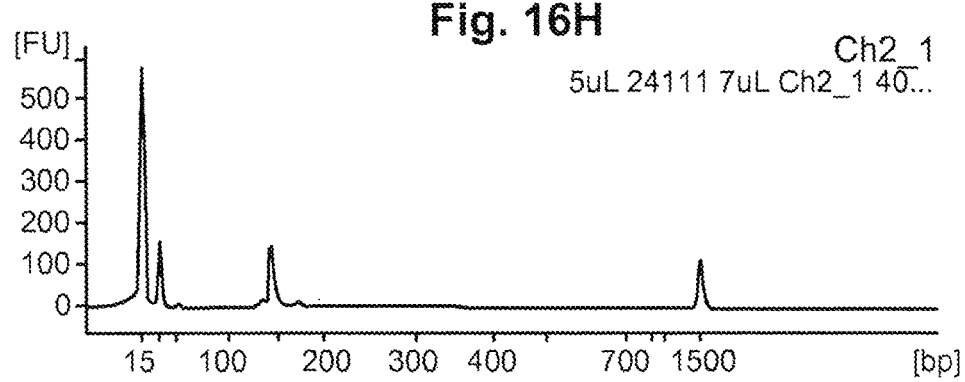
Figure 16I:
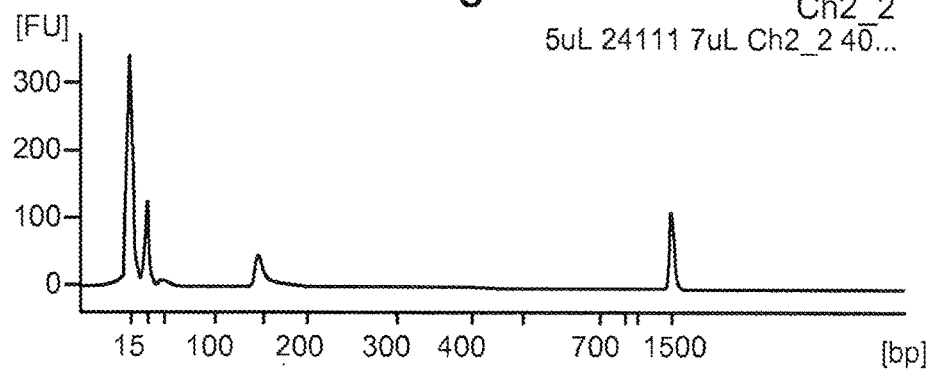
Figure 16J:
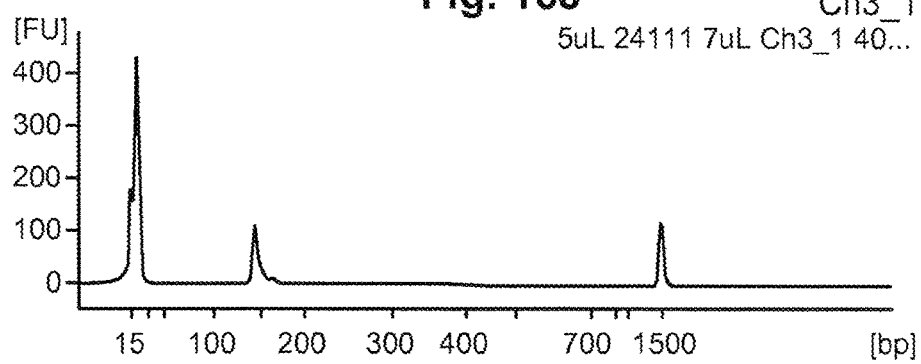
Figure 16K:
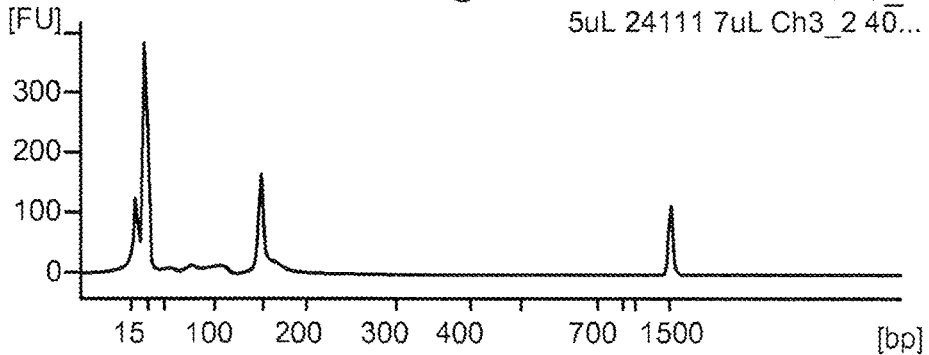
Figure 16L:
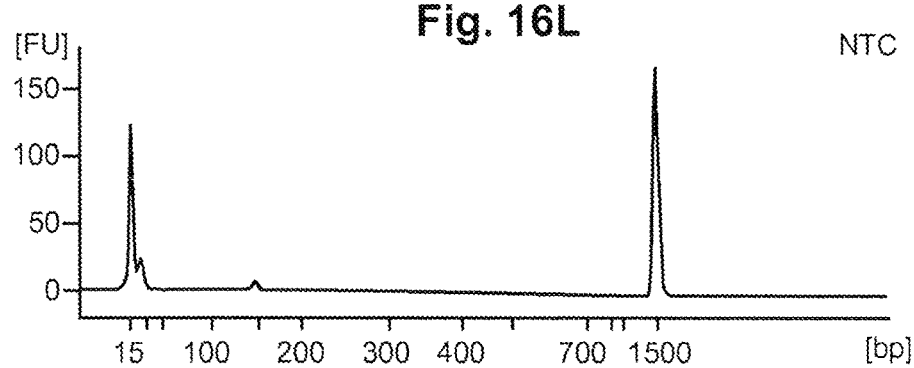
Figure 16M:
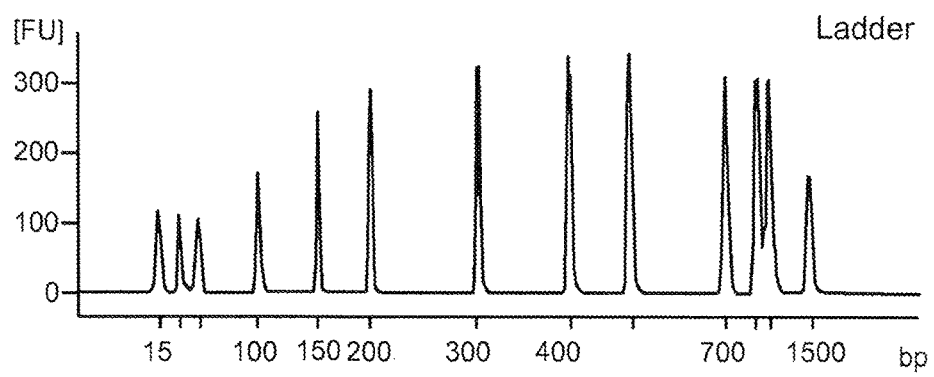

FIG. 12 illustrates a primer pair that was designed, indicating length, annealing position on chromosome 21, melting temperature ($T_m$), and percent GC content. FIG. 13 illustrates the positions of three 50 kbp regions in a Down syndrome critical region on chromosome 21. FIGS. 14A-D illustrate Bioanalyzer results of PCR amplification of different sequences from clusters A, B, and C in regions A, B, and C on chromosome 21. FIG. 15 illustrates amplification results from different clusters in regions A, B, and C of chromosome 21, one primer pair/cluster.

FIGS. 16A-M illustrate PCR amplification of chromosome 21 and reference chromosome 1 sequences. Ch21_A25, ch21_B16, and ch21_C58 are sequences selected using chromosome walk strategy. Ch1_1, ch1_2, ch2_1, ch2_2, ch3_1, ch3_2 are sequences selected using "hot spot" strategy. The sequences of primers used to generate data in FIGS. 15 and 16A-M is in Table 4.

TABLE 4

Primer sequences used to generate data in FIGS. 15, 16, and 17 (SEQ ID NOS 42-95, respectively, in order of appearance).

| | | |
|---|---|---|
| A18_F_22632000 | TGAAGCCCGGGAGGTTCCCT | |
| A18_R_22632000 | TCCAGGCTGTGTGCCCTCCC | |
| A2_F_22632000 | GCCAGGCTGCAGGAAGGAGG | |
| A2_R_22632000 | GTTAGGGGAGGGCACGCAGC | |
| A28_F_22632000 | CCAGCACCACACACCAGCCC | |
| A28_R_22632000 | GCAGAAAGCTCAGCCTGGCCC | |
| A72_F_22632000 | TCCAGTCCTGCACCCTCTCCC | |
| A72_R_22632000 | GGTGGCTCGGGGCTCCTCAT | |
| A7_F_22632000 | CAGTGTCCCCACGCACTCACG | |
| A7_R_22632000 | TCCAGCACCTCCAGCCTCCC | |
| A73_F_22632000 | CTGTGGTCAGCAGTCGCACGC | |
| A73_R_22632000 | TCCCCTTGGCCTGCCATCGT | |
| A25_F_22632000 | GGACCATGGCAACGGCCTCC | |
| A25_R_22632000 | TCCAACAGGCGGTGTCAAGCC | |
| B16_F_22681999 | GCCAAGCCTGCCTTGTGGGA | |
| B16_R_22681999 | GGTGCCCTCCCTCACGATGC | |
| B19_F_22681999 | GTGGGCACTTCAGAGCTGGGC | |
| B19_R_22681999 | GTGGGATGTGCCCTCGTGCC | |
| B54_F_22681999 | CCCGCCTTGTTGGGTACGAGC | |
| B54_R_22681999 | GAGCGGGGAGCAGGATGGGT | |
| B34_F_22681999 | TCCCAGAATGCCACGCCCTG | |
| B34_R_22681999 | GAGGTGTGTGCTGAGGGGCG | |
| B32_F_22681999 | ACTCTGTCCCGTGCCCTTGCT | |
| B32_R_22681999 | CAAGGCGCCCTTGACTGGCA | |
| B7_F_22681999 | ATGCCATGCCCAACGCCACT | |
| B7_R_22681999 | CTGTGGCCTCAGCTGCTCGG | |
| C1_F_28410001 | CTGTGGGCCGCTCTCCCTCT | |
| C1_R_28410001 | CCTCCGGTAGGGCCAAGGCT | |
| C58_F_28410001 | TGACCTGTGGGCCGCTCTCC | |
| C58_R_28410001 | CCTCCGGTAGGGCCAAGGCT | |
| C6_F_28410001 | CAGCCCTGTGAGGCATGGGC | |
| C6_R_28410001 | AGTGAGAGGAGCGGCTGCCA | |
| C74_F_28410001 | GGGGCTGGTGGAGCTGGTGA | |
| C74_R_28410001 | TGGAGCCCCACATCCTGCGT | |
| C19_F_28410001 | TGTTCCCCGTGCCTGGCTCT | |
| C19_R_28410001 | TGGGGCCCATCCTGGGGTTC | |
| C29_F_28410001 | TGATGGCACGTGTTGCCCCG | |
| C29_R_28410001 | ACCGTGGCTGACCCCTCCTC | |
| C72_F_28410001 | CGCCGGGACACAGGAAGCAC | |
| C72_R_28410001 | CCCTGGTGAGGAGCCGGGAG | |
| C55_F_28410001 | GCCAGGGAAGGACTGCGGTG | |
| C55_R_28410001 | CAGCCAGGGCAGGACTCGGA | |
| Ch1_1_150_F | GAGGTCTGGTTCGGCTTTC | ref. 1 |
| Ch1_1_150_R | CAGAGCTGGGAGGGATGAG | ref.1 |
| ch1_2_150_F | TGCAACAGCTTCGTTGGTAG | |
| ch1_2_150_R | TAGGTCCAGCAGGAAGTTGG | |
| ch2_1_150_F | GTCGGAGAAGATCCGTGAGA | |
| ch2_1_150_R | CCAGGCATCAATGTCATCAG | |
| ch2_2_150_F | TGTCAACCAGACGTTCCAAA | |
| ch2_2_150_R | TAACACAGCTGGTGCCTGAG | |
| ch3_1_150_F | ATTCCCCCTTAACCACTTGC | |
| ch3_1_150_R | GAGGGTGTCTCGCTTGGTC | |
| ch3_2_150_F | GCTGAGTAGGAAATGGGAGGT | |
| ch3_2_150_R | CTGCAGTCAGGGAGCAGAGT | |

FIG. 17 illustrates PCR amplification of reference chromosomes 1, 2, and 3. Primer sequences used to generate data are shown in Table 4.

FIG. 18 illustrates a comparison of amplification success rate using the "chromosome walk" method and the "hot spot" sequence selection method. 76% (16/21) amplifications of chromosome 21 were successful using the "chromosome walk" method to select sequences. 100% (7/7) sequences selected based on "hot spots" on chromosome 21 amplified. 100% (5/5) sequences selected based on "hot spots" on chromosomes 1, 2, and/or 3 amplified.

Example 3: Selection of Hotspot Region for Amplification

Figure 19:
FIG. 19 illustrates sequence coverage of chromosome 21.
Figure 20:
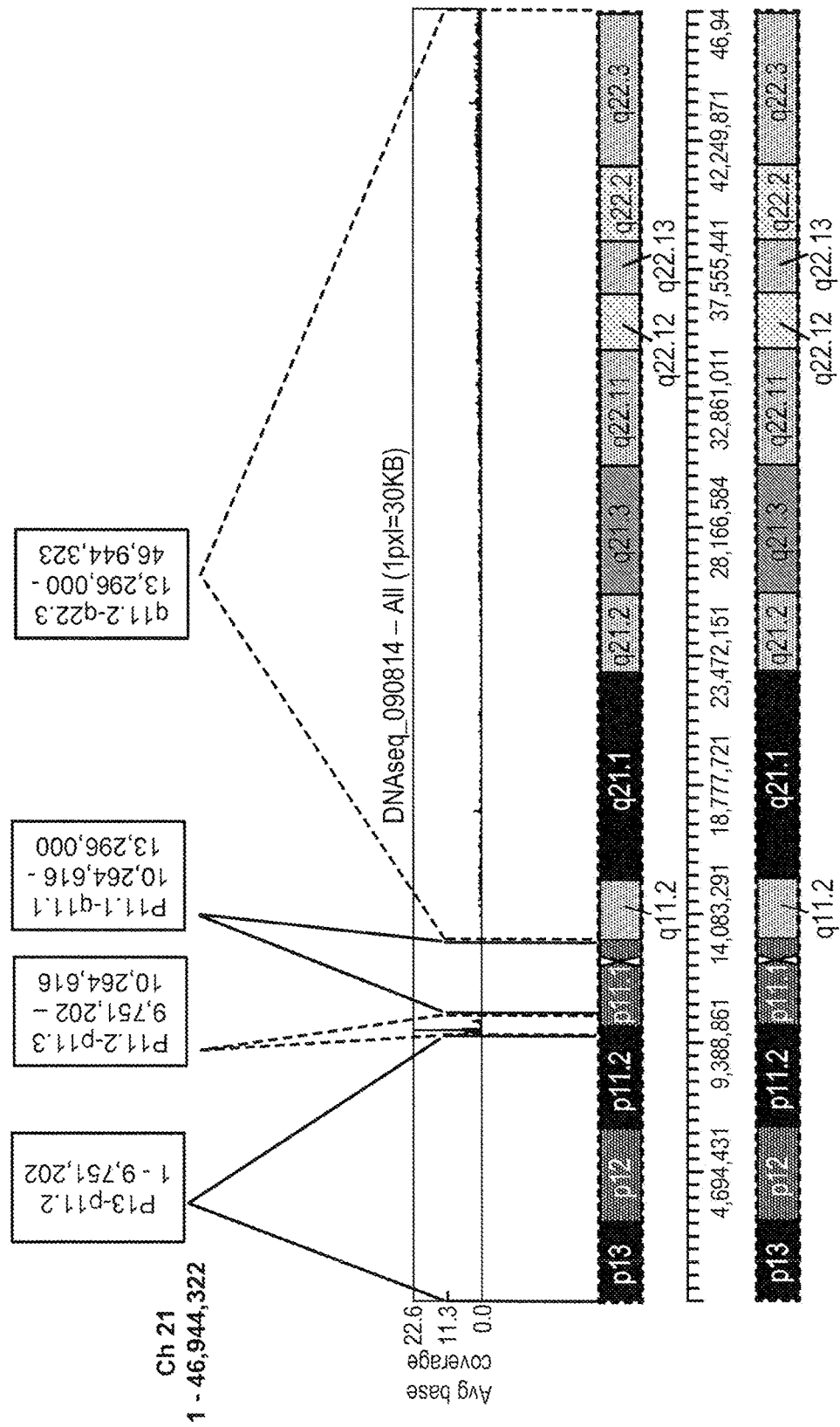
FIG. 20 highlights different regions of sequence coverage mapped to a schematic of chromosome 21.

Sequences for enrichment can be chosen on the basis of being in a "hotspot," a region of relatively high sequence coverage. FIG. 19 illustrates that sequence runs from multiple samples were combined to give 79% coverage of chromosome 21. The bottom chart illustrates Illumina pipeline output files containing multiple files and each given start and end chromosome positions; therefore the sequencing reads cover 37 M region (46,927,127 last position–9,757,475 1st position=~37 M). FIG. 20 shows a schematic of chromosome 21 to which sequence reads have been mapped. Some regions have more sequence coverage than other regions. FIG. 21 illustrates an example of a process that was used to select a specific region of 251 base pairs for amplification. Sequence within 13,296,000-46,944,323 (illustrated in FIG. 20) was selected for amplification. FIGS. 22A-C illustrate the relative position for a Down syndrome critical region (35,892,000-41,720,000) on chromosome 21. Magnified views of the sequence reads mapped to chromosome 21 are shown in FIG. 23. FIG. 24 illustrates sequence reads that map to a 4207 bp region on chromosome 21 and a 251 bp region within that 4207 bp region. The Y axis is the number of sequence reads at a chromosome position. FIG. 25 illustrates a primer pair that was designed to anneal to sequence with the 251 bp region.

Example 4: Nested PCR for DNA Library Construction

Figure 26:
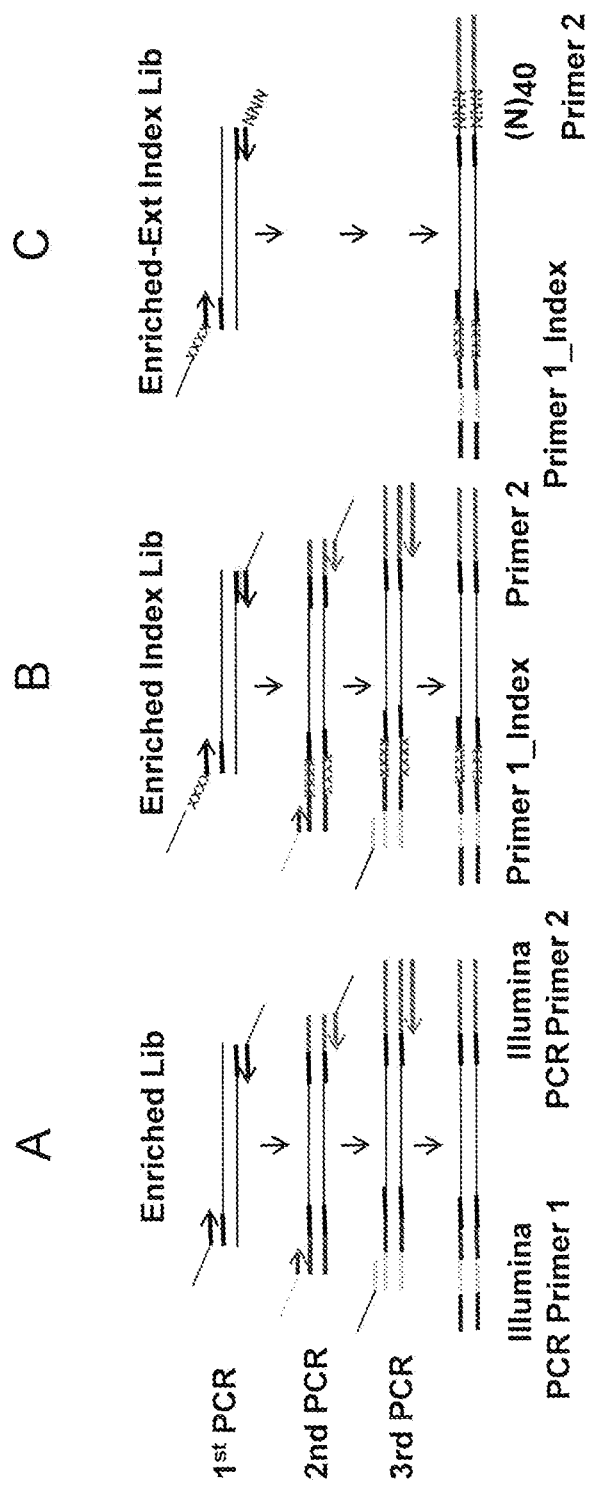
FIG. 26 illustrates a nested PCR strategy for DNA library construction.

FIG. 26 illustrates methods for generating library of enriched sequences. In the scheme shown in FIG. 26A, a three step PCR amplification process is used to generate a library of enriched nucleic acids where the fragments have sequence incorporated that can be used for annealing to primers for subsequent sequencing. A first pair of primers is used to amplify enriched sequences. These primers have sequence that anneals to a second set of primers that is used to amplify products of the first reaction. The second set of primers can have sequence that can anneal to sequencing primers. A third set of primers anneals to sequence from the first set of primers and is used further amplify the products. The third set of primers also introduces sequence onto the fragments that can anneal to sequencing primers.

The PCR scheme in FIG. 26B illustrates a means for indexing sequences. The enriched fragments from each sample (e.g., individual maternal cell-free samples) can have sequence incorporated that identifies the fragment as originating from that sample. This indexing allows multiple samples to be pooled without loss of information with respect to which sample a fragment originated. The three step PCR proceeds as shown in FIG. 26A with indexing sequence being incorporated in primers used in the first amplification step. The indexing sequence can be in primers used for the $1^{st}$, $2^{nd}$ or $3^{rd}$ amplification step.

The PCR scheme in FIG. 26C differs in that sequence is incorporated that serves to extend the length of enriched fragments. Fetal DNA in maternal cell-free samples is often less than 200 bp in size. Some amplifications enrich fragments that are, e.g., 60 bp in size. However, sequence reactions using, e.g., Illumina sequencing technology are more efficient when fragments are at least 100 bp in length. Thus, the PCR indexing scheme can be modified, e.g., as shown in FIG. 26C, to amplify fragments with sequence in the $1^{st}$, $2^{nd}$ or $3^{rd}$ step that serves to lengthen the fragments in the library.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for determining the presence or absence of fetal aneuploidy in a maternal blood sample, the method comprising:
   (a) obtaining a maternal blood sample comprising fetal and maternal cell-free DNA;
   (b) selectively enriching a plurality of non-random polynucleotide sequences of genomic DNA from cell-free DNA in a maternal blood sample to generate a library of enriched non-random polynucleotide sequences found in said fetal and maternal cell-free DNA, wherein said plurality of non-random polynucleotide sequences comprises at least 100 different non-random polynucleotide sequences selected from a chromosome tested for being aneuploid, said enriching comprising:
      (i) a first amplification step to generate a plurality of first reaction products, said amplification comprising at least 100 first primers configured to amplify at least 100 different non-random polynucleotide sequences;
      (ii) a second amplification step to generate a second reaction product, said amplification comprising a second set of primers comprising sequences contained in the first reaction products; and
      (iii) a third amplification step to generate a third reaction product comprising said library of enriched non-random polynucleotide sequences, said amplification comprising a third set of primers comprising sequences contained in the second reaction products;
      wherein at least one primer of at least one of the second and third sets of primers includes a sequence configured to be added to the different non-random polynucleotide sequences to permit the enriched non-random polynucleotide sequences of the library to anneal to a same sequencing primer for the enriched non-random polynucleotide sequences of the library; and
      wherein at least one primer of at least one of the second and third sets of primers includes a sequence configured to be added to the different non-random polynucleotide sequences to add an index to the enriched non-random polynucleotide sequences of the library, the index being indicative of the maternal blood sample from which the library was generated;
   (c) sequencing said enriched non-random polynucleotide sequences;
   (d) enumerating sequence reads from said sequencing step; and
   (e) determining the presence or absence of fetal aneuploidy based on said enumerating.

2. The method of claim 1, wherein at least one primer of the third set of primers includes a sequence configured to be added to the different non-random polynucleotide sequences to add an index to the enriched non-random polynucleotide sequences of the library, the index being indicative of the maternal blood sample from which the library was generated.

3. The method of claim 1, wherein primers of the second set of primers contain universal sequences such that nucleic acids of the second reaction product contain common universal sequences added to the different non-random polynucleotide sequences, and wherein the third set of primers are configured to hybridize at least in part to the common universal sequences.

4. The method of claim 3, wherein at least one primer of the third set of primers includes a sequence configured to be added to the different non-random polynucleotide sequences to add an index to the enriched non-random polynucleotide sequences of the library, the index being indicative of the maternal blood sample from which the library was generated.

5. The method of claim 1, wherein said plurality of non-random polynucleotide sequences comprises at least 300 different non-random polynucleotide sequences selected from the chromosome tested for being aneuploid.

6. The method of claim 1, wherein said plurality of non-random polynucleotide sequences comprises at least 500 different non-random polynucleotide sequences selected from the chromosome tested for being aneuploid.

7. The method of claim 1, wherein each of said plurality of non-random polynucleotide sequences is from 10 to 500 nucleotide bases in length.

8. The method of claim 1, wherein each of said plurality of non-random polynucleotide sequences is from 50 to 150 nucleotide bases in length.

9. The method of claim 1, wherein said selectively enriching comprises performing PCR.

10. The method of claim 1, wherein said selectively enriching comprises linear amplification.

11. The method of claim 1, wherein said non-random polynucleotide sequences comprise sequences that are sequenced at a rate of greater than 5-fold more than other sequences on the chromosome.

12. The method of claim 1, wherein said chromosome tested is selected from the group consisting of chromosome 13, chromosome 18, chromosome 21, chromosome X, and chromosome Y.

13. A method for determining the presence or absence of fetal aneuploidy in a maternal blood sample, the method comprising:
    (a) obtaining a maternal blood sample comprising fetal and maternal cell-free DNA;
    (b) selectively enriching a plurality of non-random polynucleotide sequences of genomic DNA from cell-free DNA in a maternal blood sample to generate a library of enriched non-random polynucleotide sequences found in said fetal and maternal cell-free DNA, wherein said plurality of non-random polynucleotide sequences comprises at least 100 different non-random polynucleotide sequences selected from a chromosome tested for being aneuploid, wherein said selectively enriching comprises:
        (i) amplifying said plurality of non-random polynucleotide sequences from said maternal and fetal genomic DNA using a first pair of primers to form a first product, wherein said plurality of non-random polynucleotide sequences comprises at least 100 different non-random polynucleotide sequences selected from a chromosome tested for being aneuploid;
        (ii) amplifying the first product of (i) with a second set of primers comprising sequences contained in the first product of (i) to form a second product; and
        (iii) amplifying the second product of (ii) with a third set of primers comprising sequences contained in the second product of (ii);
            wherein one of said second or third sets of primers includes an indexing sequence;
    (c) sequencing said enriched non-random polynucleotide sequences;
    (d) enumerating sequence reads from said sequencing step; and
    (e) determining the presence or absence of fetal aneuploidy based on said enumerating.

14. The method of claim 13, wherein said third set of primers includes the indexing sequence.

15. The method of claim 13, wherein said indexing sequence distinguishes polynucleotides in the maternal blood sample from polynucleotides in a different maternal blood sample.

16. The method of claim 13, wherein said cell-free DNA is from a plurality of maternal blood samples from a plurality of different individuals, and wherein said indexing sequence identifies a maternal blood sample from each of said plurality of different individuals.

17. The method of claim 13, wherein said plurality of non-random polynucleotide sequences comprises at least 300 different non-random polynucleotide sequences selected from the chromosome tested for being aneuploid.

18. The method of claim 13, wherein said plurality of non-random polynucleotide sequences comprises at least 500 different non-random polynucleotide sequences selected from the chromosome tested for being aneuploid.

19. The method of claim 13, wherein each of said plurality of non-random polynucleotide sequences is from 10 to 500 nucleotide bases in length.

20. The method of claim 13, wherein each of said plurality of non-random polynucleotide sequences is from 50 to 150 nucleotide bases in length.

21. The method of claim 13, wherein said selectively enriching comprises performing a polymerase chain reaction (PCR).

22. The method of claim 13, wherein said selectively enriching comprises linear amplification.

23. The method of claim 13, wherein said chromosome tested is selected from the group consisting of chromosome 13, chromosome 18, chromosome 21, chromosome X, and chromosome Y.

* * * * *

SEQUENCE LISTING

```
<160> NUMBER OF SEQ ID NOS: 133

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccccaagagg tgcttgtagt                                              20

<210> SEQ ID NO 2
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 2
gccatggtgg agtgtaggag                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctgaagtgct gccaacacac                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgatcttgga gcctcctttg                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agcttctcca ggacccagat                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cattcatggg aagggactca                                                 20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccattgcact ggtgtgctt                                                  19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 8
gagacgaggg gacgatagc                                           19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgccatcgta gttcagcgta                                          20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttggaccaca gctcagagg                                           19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaagtgtgct tgctccaagg                                          20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcaaaacac agcccaatag                                          20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cctagtgcgg gaaaagacac                                          20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 14
ttctctccct tgctcattgc                                                     20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gagtcagagt ggagctgagg a                                                   21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggaggtccta gtggtgagca                                                     20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgtgggaagt caggacacac                                                     20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gatcttggag cctcctttgc                                                     20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtgacagcct ggaacatgg                                                      19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 20
caaggcacct gcactaaggt                                           20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgcctcctgc tacttttacc c                                         21

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agacggaaca ggcagaggt                                            19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caagacacaa gcaggagagc                                           20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cagtttggac cacagctcag                                           20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aaagtgtgct tgctccaagg                                           20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tggaacaagc ctccattttc                                                   20

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaggtgcttg tagtcagtgc ttca                                              24

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cccggtgaca cagtcctctt                                                   20

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
agtcagagtg gagctgag                                                     18

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgctgccaac acacgtgtct                                                   20

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cagggctgtt gctcatgga                                                    19

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32 tccccctagga tatcatc                                                    17

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cccgcatctg cagctcat                                                    18

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tctctccaag tcctacatcc tgtatg                                           26

<210> SEQ ID NO 35
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
ccaggtggct tcc                                                         13

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gggagctggt acagaaatga cttc                                             24

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttgctcattg cgctgacaa                                                   19

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
agccatcctt cccgggccta gg                                               22

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gttcggcttt caccagtct                                                19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ctccatagct ctccccact                                                19

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
cgccctgcca tgtggaa                                                  17

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tgaagcccgg gaggttccct                                               20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tccaggctgt gtgccctccc                                               20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gccaggctgc aggaaggagg                                               20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
gttaggggag ggcacgcagc                                           20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
ccagcaccac acaccagccc                                           20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
gcagaaagct cagcctggcc c                                         21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
tccagtcctg caccctctcc c                                         21

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
ggtggctcgg ggctcctcat                                           20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
cagtgtcccc acgcactcac g                                         21

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
tccagcacct ccagcctccc                                                    20

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
ctgtggtcag cagtcgcacg c                                                  21

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
tccccttggc ctgccatcgt                                                    20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
ggaccatggc aacggcctcc                                                    20

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
tccaacaggc ggtgtcaagc c                                                  21

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
gccaagcctg ccttgtggga                                                    20

<210> SEQ ID NO 57

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ggtgccctcc ctcacgatgc                                              20

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gtgggcactt cagagctggg c                                            21

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtgggatgtg ccctcgtgcc                                              20

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cccgccttgt tgggtacgag c                                            21

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gagcggggag caggatgggt                                              20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tcccagaatg ccacgccctg                                              20

<210> SEQ ID NO 63
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gaggtgtgtg ctgaggggcg                                                    20

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
actctgtccc gtgcccttgc t                                                  21

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
caaggcgccc ttgactggca                                                    20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
atgccatgcc caacgccact                                                    20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ctgtggcctc agctgctcgg                                                    20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ctgtgggccg ctctccctct                                                    20

<210> SEQ ID NO 69
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 69
cctccggtag ggccaaggct                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tgacctgtgg gccgctctcc                                              20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cctccggtag ggccaaggct                                              20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cagccctgtg aggcatgggc                                              20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
agtgagagga gcggctgcca                                              20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ggggctggtg gagctggtga                                              20

<210> SEQ ID NO 75
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 75
tggagcccca catcctgcgt                                                    20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tgttccccgt gcctggctct                                                    20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tggggcccat cctggggttc                                                    20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tgatggcacg tgttgccccg                                                    20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
accgtggctg accctcctc                                                     20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cgccgggaca caggaagcac                                                    20

<210> SEQ ID NO 81
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 81
ccctggtgag gagccgggag                                                    20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gccagggaag gactgcggtg                                                    20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cagccagggc aggactcgga                                                    20

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gaggtctggt tcggctttc                                                     19

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cagagctggg agggatgag                                                     19

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tgcaacagct tcgttggtag                                                    20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 87
taggtccagc aggaagttgg                                           20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gtcggagaag atccgtgaga                                           20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ccaggcatca atgtcatcag                                           20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tgtcaaccag acgttccaaa                                           20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
taacacagct ggtgcctgag                                           20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
attccccctt aaccacttgc                                           20

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gagggtgtct cgcttggtc                                           19

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gctgagtagg aaatgggagg t                                        21

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ctgcagtcag ggagcagagt                                          20

<210> SEQ ID NO 96
<211> LENGTH: 212
<212> TYPE: DNA
<213> ORGANISM: Homo sapiens

<400> SEQUENCE: 96
caagacacaa gcaggagagc cacaaagcca gccagcttac tgccatcgta gttcagcgta      60
gcgaagttgg cctgcttctc cgcgcagccc gcactgttgc acacccgcat ctgcagctca     120
taccaggtgg cttcctgcag gtcatacagg atgtaggact tggagagaga ggtcctctga     180
gctgtggtcc aaactgtggt cccaagggc ct                                    212

<210> SEQ ID NO 97
<211> LENGTH: 36
<212> TYPE: DNA
<213> ORGANISM: Homo sapiens

<400> SEQUENCE: 97
tgccatcgta gttcagcgta gcgaagttgg cctgct                        36

<210> SEQ ID NO 98
<211> LENGTH: 36
<212> TYPE: DNA
<213> ORGANISM: Homo sapiens

<400> SEQUENCE: 98
ttggaccaca gctcagagga cctctctctc caagtc                        36

<210> SEQ ID NO 99
<211> LENGTH: 28
<212> TYPE: DNA
<213> ORGANISM: Homo sapiens

<400> SEQUENCE: 99
gtagtcagtg cttcagagtc agagtgga                                 28

<210> SEQ ID NO 100

```
<211> LENGTH: 28
<212> TYPE: DNA
<213> ORGANISM: Homo sapiens

<400> SEQUENCE: 100
cccccaagag gtgcttgtag tcagtgct                                              28

<210> SEQ ID NO 101
<211> LENGTH: 28
<212> TYPE: DNA
<213> ORGANISM: Homo sapiens

<400> SEQUENCE: 101 cgtgacccccc aagaggtgct tgtagtca                                             28

<210> SEQ ID NO 102
<211> LENGTH: 28
<212> TYPE: DNA
<213> ORGANISM: Homo sapiens

<400> SEQUENCE: 102
aacagccgtg acccccaara ggtgcttg                                              28

<210> SEQ ID NO 103
<211> LENGTH: 28
<212> TYPE: DNA
<213> ORGANISM: Homo sapiens

<400> SEQUENCE: 103
ccatggccac gccaggagcc tggtctca                                              28

<210> SEQ ID NO 104
<211> LENGTH: 28
<212> TYPE: DNA
<213> ORGANISM: Homo sapiens

<400> SEQUENCE: 104
ccatggccac gccaggagcc tggtctca                                              28

<210> SEQ ID NO 105
<211> LENGTH: 28
<212> TYPE: DNA
<213> ORGANISM: Homo sapiens

<400> SEQUENCE: 105
caccggggca gctgctgatg cccatggc                                              28

<210> SEQ ID NO 106
<211> LENGTH: 28
<212> TYPE: DNA
<213> ORGANISM: Homo sapiens

<400> SEQUENCE: 106
aggaagagga ctgtgtcacc ggggcagt                                              28

<210> SEQ ID NO 107
<211> LENGTH: 28
<212> TYPE: DNA
<213> ORGANISM: Homo sapiens

<400> SEQUENCE: 107
gaggaagagg actgtgttac cggggcag                                              28
```

```
<210> SEQ ID NO 108
<211> LENGTH: 28
<212> TYPE: DNA
<213> ORGANISM: Homo sapiens

<400> SEQUENCE: 108
gagctgagga agaggactgt gtcaccgg                                          28

<210> SEQ ID NO 109
<211> LENGTH: 28
<212> TYPE: DNA
<213> ORGANISM: Homo sapiens

<400> SEQUENCE: 109
gagtcagagt ggagctgagg aagaggac                                          28

<210> SEQ ID NO 110
<211> LENGTH: 28
<212> TYPE: DNA
<213> ORGANISM: Homo sapiens

<400> SEQUENCE: 110
gatgcccatg gccacgccag gagcctgg                                          28

<210> SEQ ID NO 111
<211> LENGTH: 28
<212> TYPE: DNA
<213> ORGANISM: Homo sapiens

<400> SEQUENCE: 111
gatgcccatg gccacgccag gagcctgg                                          28

<210> SEQ ID NO 112
<211> LENGTH: 28
<212> TYPE: DNA
<213> ORGANISM: Homo sapiens

<400> SEQUENCE: 112
ctgatgccca tggccacgcc aggagcct                                          28

<210> SEQ ID NO 113
<211> LENGTH: 28
<212> TYPE: DNA
<213> ORGANISM: Homo sapiens

<400> SEQUENCE: 113
gtcaccgggg cagttgctga tgcccatg                                          28

<210> SEQ ID NO 114
<211> LENGTH: 28
<212> TYPE: DNA
<213> ORGANISM: Homo sapiens

<400> SEQUENCE: 114
gccaggagcc tggtctcatg agtctcct                                          28

<210> SEQ ID NO 115
<211> LENGTH: 28
<212> TYPE: DNA
<213> ORGANISM: Homo sapiens

<400> SEQUENCE: 115
caccatggca tcaagctcta cccctgcc                                          28
```

```
<210> SEQ ID NO 116
<211> LENGTH: 28
<212> TYPE: DNA
<213> ORGANISM: Homo sapiens

<400> SEQUENCE: 116
caccatggca tcaagctcta cccctgcc                                28

<210> SEQ ID NO 117
<211> LENGTH: 28
<212> TYPE: DNA
<213> ORGANISM: Homo sapiens

<400> SEQUENCE: 117
ccaccatggc atcaagctct acccctgc                                28

<210> SEQ ID NO 118
<211> LENGTH: 28
<212> TYPE: DNA
<213> ORGANISM: Homo sapiens

<400> SEQUENCE: 118
cactccacca tggcatcaag ctctaccc                                28

<210> SEQ ID NO 119
<211> LENGTH: 28
<212> TYPE: DNA
<213> ORGANISM: Homo sapiens

<400> SEQUENCE: 119
cctacactcc accatggcat caagctct                                28

<210> SEQ ID NO 120
<211> LENGTH: 28
<212> TYPE: DNA
<213> ORGANISM: Homo sapiens

<400> SEQUENCE: 120
cctacactcc accatggcat caagctct                                28

<210> SEQ ID NO 121
<211> LENGTH: 28
<212> TYPE: DNA
<213> ORGANISM: Homo sapiens

<400> SEQUENCE: 121
agtctccttg tctctgagcc tctcctac                                28

<210> SEQ ID NO 122
<211> LENGTH: 28
<212> TYPE: DNA
<213> ORGANISM: Homo sapiens

<400> SEQUENCE: 122
tccaccatgg catcaagctc taccctg                                 28

<210> SEQ ID NO 123
<211> LENGTH: 28
<212> TYPE: DNA
<213> ORGANISM: Homo sapiens

<400> SEQUENCE: 123
tctcctacac tccaccatgg catcaagc                                28
```

<210> SEQ ID NO 124
<211> LENGTH: 22
<212> TYPE: DNA
<213> ORGANISM: Homo sapiens

<400> SEQUENCE: 124
ccactaggac ctcctcctgt ct                                          22

<210> SEQ ID NO 125
<211> LENGTH: 26
<212> TYPE: DNA
<213> ORGANISM: Homo sapiens

<400> SEQUENCE: 125
ctcaccacta ggacctcctc ctgtct                                      26

<210> SEQ ID NO 126
<211> LENGTH: 28
<212> TYPE: DNA
<213> ORGANISM: Homo sapiens

<400> SEQUENCE: 126
cctgcccctg ctcaccacta ggacctcc                                    28

<210> SEQ ID NO 127
<211> LENGTH: 28
<212> TYPE: DNA
<213> ORGANISM: Homo sapiens

<400> SEQUENCE: 127
tctgcccctg ctcaccacta ggacctcc                                    28

<210> SEQ ID NO 128
<211> LENGTH: 28
<212> TYPE: DNA
<213> ORGANISM: Homo sapiens

<400> SEQUENCE: 128
atgcatgtcc tgcccctgct caccacta                                    28

<210> SEQ ID NO 129
<211> LENGTH: 10
<212> TYPE: DNA
<213> ORGANISM: Homo sapiens

<400> SEQUENCE: 129
cctcctgtct                                                        10

<210> SEQ ID NO 130
<211> LENGTH: 28
<212> TYPE: DNA
<213> ORGANISM: Homo sapiens

<400> SEQUENCE: 130
cagcccccag aagatgcatg tcctgccc                                    28

<210> SEQ ID NO 131
<211> LENGTH: 26
<212> TYPE: DNA
<213> ORGANISM: Homo sapiens

<400> SEQUENCE: 131

```
ctcaccacta ggacctcctc ctgtct                                              26

<210> SEQ ID NO 132
<211> LENGTH: 28
<212> TYPE: DNA
<213> ORGANISM: Homo sapiens

<400> SEQUENCE: 132
aacagccgtg accccaaga ggtgcttg                                             28

<210> SEQ ID NO 133
<211> LENGTH: 251
<212> TYPE: DNA
<213> ORGANISM: Homo sapiens

<400> SEQUENCE: 133
aacagccgtg accccaaga ggtgcttgta gtcagtgctt cagagtcaga gtggagctga         60
ggaagaggac tgtgtcaccg gggcagttgc tgatgcccat ggccacgcca ggagcctggt       120
ctcatgagtc tccttgtctc tgagcctctc ctacactcca ccatggcatc aagctctacc       180
cctgcctccc tgcagccccc agaagatgca tgtcctgccc ctgctcacca ctaggacctc       240
ctcctgtctg g                                                            251
```